United States Patent [19]

Fujii et al.

[11] Patent Number: 5,047,521
[45] Date of Patent: Sep. 10, 1991

[54] 5-FLUOROURACIL DERIVATIVES

[75] Inventors: Setsuro Fujii, Kyoto; Mitsuru Hirohashi, Otsu; Yoshihito Yamamoto, Otsu; Yutaka Kojima, Otsu, all of Japan

[73] Assignee: Otsuka Pharmaceutical Co., Ltd., Tokyo, Japan

[21] Appl. No.: 150,407

[22] PCT Filed: Apr. 30, 1987

[86] PCT No.: PCT/JP87/00275

§ 371 Date: Feb. 9, 1988

§ 102(e) Date: Feb. 9, 1988

[30] Foreign Application Priority Data

Apr. 30, 1986 [JP] Japan .................. 61-101285
Feb. 27, 1987 [JP] Japan .................. 62-45754

[51] Int. Cl.$^5$ ............................. C07H 19/00
[52] U.S. Cl. ............................. 536/23; 536/26
[58] Field of Search ...................... 536/23, 24

[56] References Cited

U.S. PATENT DOCUMENTS

| 4,124,765 | 11/1978 | Kurono et al. | 536/23 |
| 4,340,728 | 7/1982 | Endo et al. | 536/23 |
| 4,515,618 | 5/1985 | Loh | 536/18.1 |
| 4,599,404 | 7/1986 | Fujii et al. | 536/23 |
| 4,757,139 | 7/1988 | Kawaguchi et al. | 536/23 |
| 4,946,951 | 8/1990 | Tada et al. | 536/23 |
| 4,992,534 | 2/1991 | Fujii et al. | 536/23 |

FOREIGN PATENT DOCUMENTS

| 009882 | 4/1980 | European Pat. Off. |
| 0129984 | 1/1985 | European Pat. Off. |
| 2658672 | 6/1978 | Fed. Rep. of Germany |
| 2428052 | 1/1980 | France |
| 59-29699 | 2/1984 | Japan |
| 2187484 | 2/1986 | Japan .................. 536/23 |
| 2072164 | 4/1980 | United Kingdom |
| 2066812 | 7/1981 | United Kingdom |

OTHER PUBLICATIONS

Chemical Abstracts, vol. 101, 1984, p. 657, Abstract 55478 y published in Columbus, Ohio, U.S.A., on Feb. 16, 1984.

Primary Examiner—Johnnie R. Brown
Assistant Examiner—James O. Wilson
Attorney, Agent, or Firm—Armstrong, Nikaido, Marmelstein, Kubovcik & Murray

[57] ABSTRACT

This invention relates to a novel 5-fluorouracil derivative represented by the formula

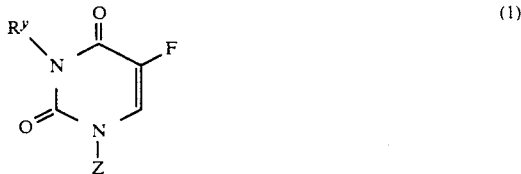

wherein $R^y$ is a hydrogen atom or a specific acyl group, Z is a phenyl-lower alkoxy-lower alkyl group, thienyl-lower alkyl group optionally substituted with halogen atom on the thienyl ring, or a group

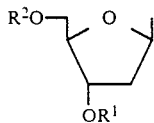

wherein $R^1$ and $R^2$ are each a hydrogen atom, a specific acyl group, phenyl-lower alkyl group having a group $R^xOCO$— on the phenyl ring, or a group —$(A)_nB$, $R^x$ being a specific organic group, A being a lower alkylene group, n being 0 or 1, and B being a 5- or 6-membered unsaturated heterocyclic group having 1 to 4 hetero-atoms selected from N, O and S and optionally having a benzene ring, naphthalene ring or pyridine ring condensed therewith, with the proviso that $R^1$ and $R^2$ are not hydrogen atoms or specific acyl groups at the same time; to a process for preparing the same; and to an anticancer composition comprising the same as an effective ingredient.

26 Claims, No Drawings

5-FLUOROURACIL DERIVATIVES

TECHNICAL FIELD

This invention relates to novel 5-fluorouracil derivatives.

BACKGROUND ART

The 5-fluorouracil derivatives of the present invention are novel compounds undisclosed in literature.

We carried out extensive research in an attempt to improve the antitumor action of known 5-fluorouracils and 2'-deoxy-5-fluorouridines and to render them less toxic, and succeeded in synthesizing a class of novel 2'-deoxy-5-fluorouridines which are substituted at the 3'- and/or 5'-position with a phenyl-lower alkyl group having a specific substituent, heterocyclic lower alkyl group optionally having a specific substituent or unsaturated heterocyclic group optionally having a specific substituent; and a class of novel 5-fluorouracils which are substituted at the 1-position with a lower alkyl group having a specific substituent and which have a specific acyl group introduced into the 3-position. We have found that these novel compounds are outstanding in anticancer action, absorption, long lasting effect and therapeutic index, low in toxicity, and therefore very useful as antitumor agents.

We have also successfully synthesized novel compounds which are usable as intermediates for synthesis of said novel compounds useful as antitumor agents.

DISCLOSURE OF INVENTION

The present invention provides a 5-fluorouracil derivative represented by the formula

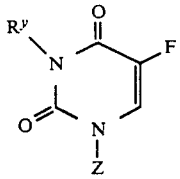

(1)

wherein $R^y$ is a hydrogen atom or acyl group, Z is a phenyl-lower alkoxy-lower alkyl group, thienyl-lower alkyl group optionally substituted with halogen atom on the thienyl ring, or a group

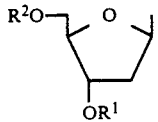

wherein $R^1$ and $R^2$ are each a hydrogen atom, acyl group, phenyl-lower alkyl group having a group $R^xOCO—$ on the phenyl ring, or a group $—(A)_nB$, the acyl group represented by $R^y$, $R^1$ and $R^2$ being lower alkanoyl group, benzoyl group optionally having 1 to 3 substituents selected from halogen atom, lower alkyl group and lower alkoxy group, phenoxycarbonyl group or a group $R^xOCOYCO—$, $R^x$ in the group $R^xOCO—$ and the group $R^xOCOYCO—$ being a pyridyl group optionally having 1 to 4 substituents selected from the group consisting of hydroxyl group, oxo group, halogen atom, amino group, carboxyl group, cyano group, nitro group, carbamoyl group, lower alkylcarbamoyl group, carboxy-lower alkylcarbamoyl group, lower alkoxycarbonyl-lower alkylcarbamoyl group, phenylcarbamoyl group optionally having on the phenyl ring 1 to 3 substituents selected from halogen atom, lower alkyl group and lower alkoxy group, lower alkyl group, lower alkenyl group, lower alkoxycarbonyl group, tetrahydrofuranyl group, tetrahydropyranyl group, lower alkoxy-lower alkyl group, phenyl-lower alkoxy-lower alkyl group, lower alkylthio-lower alkyl group, lower alkanoyloxy group, benzoyloxy group optionally having 1 to 3 substituents selected from halogen atom, lower alkyl group and lower alkoxy group, and phenoxycarbonyloxy group, Y in the group $R^xOCOYCO—$ being an arylene group, A in the group $—(A)_nB$ being a lower alkylene group, n in said group being 0 or 1 and B in said group being a 5- or 6-membered unsaturated heterocyclic group having 1 to 4 hetero-atoms selected from nitrogen, oxygen and sulfur and optionally having a benzene ring, naphthalene ring or pyridine ring condensed therewith, the heterocyclic ring optionally having 1 to 3 substituents attached thereon, the substituents being selected from the group consisting of hydroxyl group, cyano group, halogen atom, lower alkyl group, lower alkoxy group, phenyl group, lower alkoxy group having 1 or 2 phenyl groups optionally substituted with lower alkoxy group or halogen atom on the phenyl ring, phenoxy group optionally substituted with halogen atom or lower alkoxy group on the phenyl ring, nitro group, oxo group, benzoyloxy group, lower alkoxycarbonyl group, lower alkanoyloxy group, phenyl-lower alkylthio group and a group $R^xOCO—$ (wherein $R^x$ is as defined above), with the proviso that when $R^1$ is a hydrogen atom or acyl group, $R^2$ is not a hydrogen atom or acyl group and that when Z is a phenyl-lower alkoxy-lower alkyl group or thienyl-lower alkyl group optionally substituted with halogen atom on the thienyl ring, $R^y$ is an acyl group represented by the formula

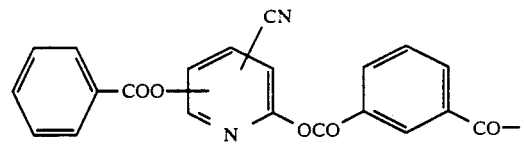

The 5-fluorouracil derivatives of the present invention represented by the formula (1) include compounds represented by the following formulas (1α) and (1β)

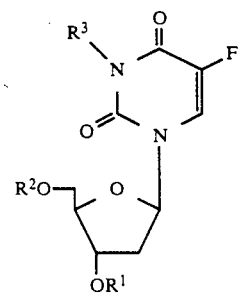

(1α)

wherein $R^1$ and $R^2$ are as defined above and R3 represents the same group as the group $R^y$,

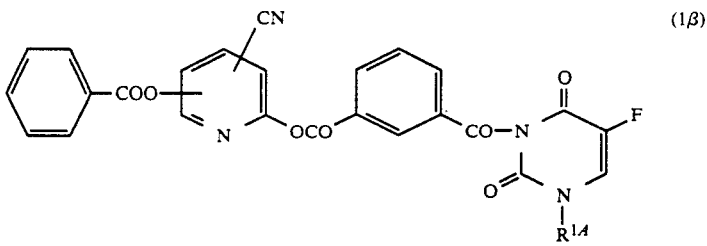

wherein $R^{14}$ is a phenyl-lower alkoxy-lower alkyl group, thienyl-lower alkyl group optionally substituted with halogen atom on the thienyl ring.

The compounds of the formulas (1α) and (1β) are generally high in anticancer action, absorption, long lasting effect and therapeutic index, low in toxicity and therefore very useful as antitumor agents.

Throughout the description, the term "halogen" used as it is or as contained in various groups is intended to include flourine, chlorine, bromine, iodine, etc. The term "lower alkyl" used as such or as contained in various groups is intended to include $C_1$-$C_6$ straight or branched chain alkyl group such as methyl, ethyl, propyl, isopropyl, butyl, tert-butyl, pentyl, hexyl, etc. Further thoughtout the description, the terms "lower alkoxy" in lower alkoxy group and in lower alkoxycarbonyl group used as such or as contained in various groups are intended to include $C_1$-$C_6$ straight or branched chain alkoxy groups, such as methoxy, ethoxy, propoxy, isopropoxy, butoxy, tert-butoxy, pentyloxy, hexyloxy, etc. Also throughout the description, the term "lower alkylene" used as such or as contained in various groups is meant to include $C_1$-$C_6$ straight or branched chain alkylene groups such as methylene, ethylene, trimethylene, 1-methylethylene, tetramethylene, 2-methyltrimethylene, pentamethylene, hexamethylene, etc.

In the description and claims, and particularly referring to the general formulas and reaction schemes, the term "acyl" is used to refer to lower alkanoyl, benzoyl optionally having 1 to 3 substituents selected from halogen atom, lower alkyl group and lower alkoxy group, phenoxycarbonyl, or a group $R^xOCOYCO$— wherein $R^x$ and Y are as defined above.

Examples of groups contained in the compound of the formula (1α) according to the present invention are described below.

Examples of the acyl groups are as follows.

(i) $C_1$-$C_6$ alkanoyl groups such as formyl, acetyl, propanoyl, butanoyl, isobutanoyl, pentanoyl, hexanoyl, etc.

(ii) benzoyl groups optionally substituted with 1 to 3 substituents selected from the group consisting of halogen atom, lower alkyl group and lower alkoxy group, such as benzoyl, 2-methylbenzoyl, 3-methylbenzoyl, 4-methylbenzoyl, 2,4-dimethylbenzoyl, 3,4,5-trimethylbenzoyl, 4-ethylbenzoyl, 2-methoxybenzoyl, 3-methoxybenzoyl, 4-methoxybenzoyl, 2,4-dimethoxybenzoyl, 3,4,5-trimethoxybenzoyl, 4-ethoxybenzoyl, 2-methoxy-4-ethoxybenzoyl, 2-propoxybenzoyl, 3-propoxybenzoyl, 4-propoxybenzoyl, 2,4-dipropoxybenzoyl, 3,4,5-tripropoxy benzoyl, 2-chlorobenzoyl, 3-chlorobenzoyl, 4-chlorobenzoyl, 2,3-dichlorobenzoyl, 2,4,6-trichlorobenzoyl, 2-bromobenzoyl, 4-fluorobenzoyl, etc.

(iii) phenoxycarbonyl group (iv) pyridyloxycarbonylarylenecarbonyl group represented by the formula

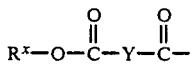  (Y)

wherein $R^x$ and Y are as defined above.

The substituents on the substituted pyridyl group represented by $R^x$ in the group of the formula (Y) are exemplified below.

(a) Examples of lower alkylcarbamoyl groups are alkylcarbamoyl groups having one or two $C_1$-$C_6$ alkyl groups such as N-methylcarbamoyl, N-ethylcarbamoyl, N-propylcarbamoyl, N-isopropylcarbamoyl, N-butylcarbamoyl, N-tert-butylcarbamoyl, N-pentylcarbamoyl, N-hexylcarbamoyl, N,N-dimethylcarbamoyl, N,N-diethylcarbamoyl, N,N-dipropylcarbamoyl, N-isopropyl-N-methylcarbamoyl, N-ethyl-N-methylcarbamoyl, N-methyl-N-pentyl-carbamoyl, N-propyl-N-pentylcarbamoyl, N,N-dipentylcarbamoyl, N-ethyl-N-hexylcarbamoyl, N-hexyl-N-pentylcarbamoyl, N,N-dihexylcarbamoyl and the like.

(b) Examples of carboxy-lower alkylcarbamoyl groups are carboxyalkylcarbamoyl groups in which the alkyl moiety has 1 to 6 carbon atoms, such as carboxymethylcarbamoyl, 2-carboxyethylcarbamoyl, 3-carboxypropylcarbamoyl, 4-carboxybutylcarbamoyl, 2-carboxy-1,1-dimethylethylcarbamoyl, 5-carboxypentylcarbamoyl, 6-carboxyhexylcarbamoyl and the like.

(c) Examples of lower alkoxycarbonyl-lower alkylcarbamoyl groups are carbamoyl groups substituted with one alkoxycarbonylalkyl group in which the alkoxy moiety and the alkyl moiety each have 1 to 6 carbon atoms, such as methoxycarbonylmethylcarbamoyl, 3-methoxycarbonylpropylcarbamoyl, ethoxycarbonylmethylcarbamoyl, propoxycarbonylmethylcarbamoyl, isopropoxycarbonylmethylcarbamoyl, butoxycarbonylmethylcarbamoyl, tert-butoxycarbonylmethylcarbamoyl, pentyloxycarbonylmethylcarbamoyl, hexyloxycarbonylmethylcarbamoyl, 2-methoxycarbonylethylcarbamoyl, 2-methoxycarbonyl-1-methyl-ethylcarbamoyl, 4-methoxycarbonylbutylcarbamoyl, 5-methoxycarbonylpentylcarbamoyl, 6-methoxycarbonylhexylcarbamoyl, 2-ethoxycarbonylethylcarbamoyl, 4-ethoxycarbonylbutylcarbamoyl, 6-propoxycarbonylhexylcarbamoyl, 5-isopropoxycarbonylpentylcarbamoyl, 1,1-dimethyl-2-butoxycarbonylethylcarbamoyl, 2-methyl-3-tert-butoxycarbonylpropylcarbamoyl, 2-pentyloxycarbonylethylcarbamoyl, hexyloxycarbonylethylcarbamoyl and the like.

(d) Examples of phenylcarbamoyl groups optionally having 1 to 3 substituents selected from the group consisting of halogen, lower alkyl and lower alkoxy on the phenyl ring are carbamoyl groups having one or two phenyl groups which may optionally have 1 to 3 substituents selected from the group consisting of halogen, $C_1$–$C_6$ alkoxy and $C_1$–$C_6$ alkyl on the phenyl ring such as N-(2-chlorophenyl)carbamoyl, N-(3,5-dichloro)phenylcarbamoyl, N-(3-methoxyphenyl)carbamoyl, N-(4-propoxyphenyl)carbamoyl, N-(2-methylphenyl)carbamoyl, N-(4-ethylphenyl)carbamoyl, N-(3-isopropylphenyl)carbamoyl, N-(4-hexylphenyl)carbamoyl, N-phenylcarbamoyl, N,N-diphenylcarbamoyl and the like.

(e) Examples of lower alkenyl groups are $C_2$–$C_6$ alkenyl groups such as vinyl, allyl, 2-butenyl, 3-butenyl, 1-methylallyl, 2-pentenyl, 2-hexenyl and the like.

(f) Examples of lower alkoxycarbonyl groups are carbonyl groups having $C_1$–$C_6$ alkoxy group such as methoxycarbonyl, ethoxycarbonyl, propoxycarbonyl, isopropoxycarbonyl, tert-butoxycarbonyl, butoxycarbonyl, pentyloxycarbonyl, hexyloxycarbonyl and the like.

(g) Examples of tetrahydrofuranyl groups are 2-tetrahydrofuranyl, 3-tetrahydrofuranyl and the like.

(h) Examples of tetrahydropyranyl groups are 2-tetrahydropyranyl, 3-tetrahydropyranyl, 4-tetrahydropyranyl and the like.

(i) Examples of lower alkoxy-lower alkyl groups are alkoxyalkyl groups in which the alkoxy moiety and alkyl moiety each have 1 to 6 carbon atoms, such as methoxymethyl, ethoxymethyl, propoxymethyl, 3-methoxypropyl, 4-ethoxybutyl, 6-propoxyhexyl, 5-isopropoxypentyl, 1,1-dimethyl-2-butoxyethyl, 2-methyl-3-tert-butoxypropyl, 2pentyloxyethyl, 2-hexyloxyethyl and the like.

(j) Examples of phenyl-lower alkoxy-lower alkyl groups are phenylalkoxyalkyl groups in which phenyl group is present and the alkoxy moiety and alkyl moiety each have 1 to 6 carbon atoms, such as benzyloxymethyl, 2-benzyloxyethyl, 5-(2-phenylpentyloxy)pentyl, 6-benzyloxyhexyl, 6-(4-phenylhexyloxy)hexyl, 2-phenylethoxymethyl, 2-(phenylmethoxy)ethyl, 2-(phenylmethoxy)propyl, 4-(phenylmethoxy)butyl, 5-(phenylmethoxy)pentyl, 6-(phenylmethoxy)hexyl, 2-(2-phenylethoxy)ethyl, 2-(4-phenylbutoxy)ethyl, 4-(4-phenylbutoxy)butyl, 6-phenylmethoxyhexyl and the like.

(k) Examples of lower alkylthio-lower alkyl groups are alkylthioalkyl groups in which each of alkyl moieties has 1 to 6 carbon atoms, such as methylthiomethyl, ethylthiomethyl, propylthiomethyl, butylthiomethyl, tert-butylthiomethyl, methylthiobutyl, ethylthiohexyl and the like.

(l) Examples of lower alkanoyloxy groups are those having alkanoyl exemplified in the foregoing item (i).

(m) Examples of benzoyloxy groups optionally having 1 to 3 substituents selected from halogen atom, lower alkyl and lower alkoxy are those having benzoyl or substituted benzoyl exemplified in the foregoing item (ii).

In the substituted pyridyl group represented by $R^x$, the pyridine ring is preferably substituted at any of the 2- to 6-positions with one to four of the substituents selected from the group consisting of the hydroxy, halogen, amino, carboxyl, cyano, nitro, oxo, lower alkyl, lower alkenyl, lower alkoxycarbonyl, carbamoyl, lower alkanoyloxy, benzoyloxy optionally having substituents, and phenoxycarbonyloxy among the substituents exemplified above, or preferably substituted at the 1-position with the carbamoyl, lower alkylcarbamoyl, carboxy lower alkylcarbamoyl, phenylcarbamoyl optionally having 1 to 3 substituents selected from the group consisting of halogen, lower alkoxy and lower alkyl on the phenyl ring, tetrahydrofuranyl, tetrahydropyranyl, phthalidyl, lower alkoxy-lower alkyl, lower alkylthio-lower alkyl, phenyllower alkoxy-lower alkyl or lower alkoxycarbonyl-lower alkylcarbamoyl group among the substituents exemplified above.

Examples of the pyridyl groups represented by $R^x$ and optionally having the above various substituents are as follows.

2-pyridyl, 3-pyridyl, 4-pyridyl,
2-hydroxy-3-pyridyl, 2-hydroxy-4-pyridyl,
2-hydroxy-5-pyridyl, 2-hydroxy-6-pyridyl,
2-hydroxy-5-chloro-3-pyridyl,
2-hydroxy-5-chloro-4-pyridyl,
4-hydroxy-5-chloro-2-pyridyl,
2-hydroxy-5-chloro-6-pyridyl,
2-hydroxy-5-fluoro-4-pyridyl,
4-hydroxy-5-fluoro-2-pyridyl,
2-hydroxy-5-fluoro-6-pyridyl,
2-hydroxy-5-bromo-4-pyridyl,
4-hydroxy-5-bromo-2-pyridyl,
2-hydroxy-5-bromo-6-pyridyl,
2-hydroxy-5-iodo-4-pyridyl,
4-hydroxy-5-iodo-2-pyridyl,
2-hydroxy-5-iodo-6-pyridyl,
2-hydroxy-3-bromo-4-pyridyl,
4-hydroxy-3-bromo-2-pyridyl,
2-hydroxy-3-chloro-4-pyridyl,
4-hydroxy-3-chloro-2-pyridyl,
2-hydroxy-3-chloro-6-pyridyl,
2-hydroxy-4-chloro-6-pyridyl,
1-(2-tetrahydrofuranyl)-1,2-dihydro-2-oxo-3-pyridyl,
1-(2-tetrahydrofuranyl)-1,2-dihydro-2-oxo-4-pyridyl,
1-(2-tetrahydrofuranyl)-1,2-dihydro-2-oxo-5-pyridyl,
1-(2-tetrahydrofuranyl)-1,2-dihydro-2-oxo-6-pyridyl,
1-(3-tetrahydrofuranyl)-1,2-dihydro-2-oxo-4-pyridyl,
1-(2-tetrahydrofuranyl)-1,2-dihydro-2-oxo-5-chloro-4-pyridyl,
1-(2-tetrahydrofuranyl)-1,2-dihydro-2-oxo-5-chloro-6-pyridyl,
1-(2-tetrahydrofuranyl)-1,2-dihydro-2-oxo-5-fluoro-4-pyridyl,
1-(2-tetrahydrofuranyl)-1,2-dihydro-2-oxo-5-bromo-4-pyridyl,
1-(2-tetrahydrofuranyl)-1,2-dihydro-2-oxo-5-iodo-4-pyridyl,
1-(3-tetrahydrofuranyl)-1,2-dihydro-2-oxo-5-chloro-4-pyridyl,
1-(2-tetrahydrofuranyl)-1,2-dihydro-2-oxo-3-chloro-4-pyridyl,
1-ethoxymethyl-1,2-dihydro-2-oxo-3-pyridyl,
1-ethoxymethyl-1,2-dihydro-2-oxo-4-pyridyl,
1-ethoxymethyl-1,2-dihydro-2-oxo-5-pyridyl,
1-ethoxymethyl-1,2-dihydro-2-oxo-6-pyridyl,
1-methoxymethyl-1,2-dihydro-2-oxo-4-pyridyl,
1-(2-methoxyethyl)-1,2-dihydro-2-oxo-4-pyridyl,
1-ethoxymethyl-1,2-dihydro-2-oxo-5-chloro-3-pyridyl,
1-ethoxymethyl-1,2-dihydro-2-oxo-5-chloro-4-pyridyl,
1-ethoxymethyl-1,2-dihydro-2-oxo-5-chloro-6-pyridyl,
1-ethoxymethyl-1,2-dihydro-2-oxo-5-fluoro-4-pyridyl,
1-ethoxymethyl-1,2-dihydro-2-oxo-5-bromo-4-pyridyl,
1-ethoxymethyl-1,2-dihydro-2-oxo-5-iodo-4-pyridyl,
1-methoxymethyl-1,2-dihydro-2-oxo-5-chloro-4-pyridyl,
1-(2-methoxyethyl)-1,2-dihydro-2-oxo-5-chloro-4-pyridyl,
1-(2-ethoxymethyl)-1,2-dihydro-2-oxo-3-chloro-4-pyridyl,
2-acetyloxy-5-chloro-4-pyridyl, 2-acetyloxy-5-fluoro-4-pyridyl,
2-acetyloxy-5-bromo-4-pyridyl,
2-acetyloxy-5-iodo-4-pyridyl,
2-acetyloxy-5-methyl-4-pyridyl,
2-acetyloxy-5-cyano-4-pyridyl,
2-acetyloxy-5-nitro-4-pyridyl,
2-acetyloxy-5-carboxy-4-pyridyl,
2-propanoyloxy-5-chloro-4-pyridyl,
2-butanoyloxy-5-chloro-4-pyridyl,
2-isobutanoyloxy-5-chloro-4-pyridyl,
2-pentanoyloxy-5-chloro-4-pyridyl,
2-hexanoyloxy-5-chloro-4-pyridyl,
3-acetyloxy-5-chloro-4-pyridyl,
2-acetyloxy-3-chloro-4-pyridyl,
4-acetyloxy-5-chloro-2-pyridyl,
4-acetyloxy-5-fluoro-2-pyridyl,
4-acetyloxy-5-bromo-2-pyridyl,
4-acetyloxy-5-iodo-2-pyridyl,
4-acetyloxy-5-methyl-2-pyridyl,
4-acetyloxy-5-cyano-2-pyridyl,
4-acetyloxy-5-nitro-2-pyridyl,
4-acetyloxy-5-carboxy-2-pyridyl,
6-acetyloxy-5-chloro-2-pyridyl,
4-propionyloxy-5-chloro-2-pyridyl,
4-butanoyloxy-5-chloro-2-pyridyl,
4-isobutanoyloxy-5-chloro-2-pyridyl,
4-pentanoyloxy-5-chloro-2-pyridyl,
4-hexanoyloxy-5-chloro-2-pyridyl,
4-acetyloxy-3-chloro-2-pyridyl,
3-acetyloxy-5-chloro-2-pyridyl,
2-acetyloxy-4-pyridyl, 2-propionyloxy-4-pyridyl,
2-hexanoyloxy-4-pyridyl, 4-acetyloxy-2-pyridyl,
4-propionyloxy-2-pyridyl, 4-hexanoyloxy-2-pyridyl,
2-benzoyloxy-4-pyridyl, 3-benzoyloxy-4-pyridyl,
4-benzoyloxy-2-pyridyl, 3-benzoyloxy-2-pyridyl,
2-(2-methylbenzoyl)oxy-4-pyridyl,
2(3-methylbenzoyl)oxy-4-pyridyl,
2-(4-methylbenzoyl)oxy-4-pyridyl,
2-(4-ethylbenzoyl)oxy-4-pyridyl,
2-(2-chlorobenzoyl)oxy-4-pyridyl,
2-(3-chlorobenzoyl)oxy-4-pyridyl,
2-(4-chlorobenzoyl)oxy-4-pyridyl,
2-(4-fluorobenzoyl)oxy-4-pyridyl,
2-(4-tert-butylbenzoyl)oxy-4-pyridyl,
2-(4-hexylbenzoyl)oxy-4-pyridyl,
4-(2-methylbenzoyl)oxy-2-pyridyl,
4-(4-ethylbenzoyl)oxy-2-pyridyl,
4-(3-chlorobenzoyl)oxy-2-pyridyl,
4-(4-fluorobenzoyl)oxy-2-pyridyl,
4-(4-tert-butylbenzoyl)oxy-2-pyridyl,
2-benzoyloxy-5-chloro-4-pyridyl,
2-benzoyloxy-5-fluoro-4-pyridyl,
2-benzoyloxy-5-bromo-4-pyridyl,
2-benzoyloxy-5-iodo-4-pyridyl,
2-benzoyloxy-5-methyl-4-pyridyl,
2-benzoyloxy-5-cyano-4-pyridyl,
2-benzoyloxy-5-nitro-4-pyridyl,
2-benzoyloxy-5-carboxy-4-pyridyl,
3-benzoyloxy-5-chloro-4-pyridyl,
2-benzoyloxy-3-chloro-4-pyridyl,
2-(2-methylbenzoyl)oxy-5-chloro-4-pyridyl,
2-(3-methylbenzoyl)oxy-5-chloro-4-pyridyl,
2-(4-methylbenzoyl)oxy-5-chloro-4-pyridyl,
2-(3,4,5-trimethylbenzoyl)oxy-5-chloro-4-pyridyl,
2-(4-ethylbenzoyl)oxy-5-chloro-4-pyridyl,
2-(4-tert-butylbenzoyl)oxy-5-fluoro-4-pyridyl,
2-(4-hexylbenzoyl)oxy-5-bromo-4-pyridyl,
2-(2-chlorobenzoyl)oxy-5-chloro-4-pyridyl,
2-(3-chlorobenzoyl)oxy-5-chloro-4-pyridyl,
2-(4-chlorobenzoyl)oxy-5-chloro-4-pyridyl,
2-(4-fluorobenzoyl)oxy-5-chloro-4-pyridyl,
2-(2,4-dichlorobenzoyl)oxy-5-chloro-4-pyridyl,
2-(3,4,5-trichlorobenzoyl)oxy-5-chloro-4-pyridyl,
2-(2-methoxybenzoyl)oxy-5-chloro-4-pyridyl,
2-(3-methoxybenzoyl)oxy-5-chloro-4-pyridyl,
2-(4-methoxybenzoyl)oxy-5-chloro-4-pyridyl,
2-(3,4,5-trimethoxybenzoyl)oxy-5-chloro-4-pyridyl,
4-benzoyloxy-5-chloro-2-pyridyl,
4-benzoyloxy-5-fluoro-2-pyridyl,
4-benzoyloxy-5-bromo-2-pyridyl,
4-benzoyloxy-5-iodo-2-pyridyl,
4-benzoyloxy-5-methyl-2-pyridyl,
4-benzoyloxy-5-cyano-2-pyridyl,
4-benzoyloxy-5-nitro-2-pyridyl,
4-benzoyloxy-5-carboxy-2-pyridyl,
3-benzoyloxy-5-chloro-2-pyridyl,
6-benzoyloxy-5-chloro-2-pyridyl,
4-(4-methylbenzoyl)oxy-5-chloro-2-pyridyl,
4-(2,4-dimethylbenzoyl)oxy-5-chloro-2-pyridyl,
4-(3,4,5-trimethylbenzoyl)oxy-5-chloro-2-pyridyl,
4-(2-chlorobenzoyl)oxy-5-chloro-2-pyridyl,
4-(2,4-dichlorobenzoyl)oxy-5-chloro-2-pyridyl,
4-(4-methoxybenzoyl)oxy-5-chloro-2-pyridyl,
1-phthalidyl-1,2-dihydro-2-oxo-3-pyridyl,
1-phthalidyl-1,2-dihydro-2-oxo-4-pyridyl,
1-phthalidyl-1,2-dihydro-2-oxo-5-pyridyl,
1-phthalidyl-1,2-dihydro-2-oxo-6-pyridyl,
1-carbomethoxymethylcarbamoyl-1,2-dihydro-2-oxo-3-pyridyl,
1-carbomethoxymethylcarbamoyl-1,2-dihydro-2-oxo-4-pyridyl,
1-carbomethoxymethylcarbamoyl-1,2-dihydro-2-oxo-5-pyridyl,
1-carbomethoxymethylcarbamoyl-1,2-dihydro-2-oxo-6-pyridyl,
1-carboethoxymethylcarbamoyl-1,2-dihydro-2-oxo-4-pyridyl,
2-hydroxy-5-methyl-3-pyridyl,
2-hydroxy-5-methyl-4-pyridyl,
2-hydroxy-5-methyl-6-pyridyl,
2-hydroxy-5-ethyl-4-pyridyl,
2-hydroxy-3-methyl-4-pyridyl,
2-hydroxy-3-cyano-4-pyridyl,
2-hydroxy-3-cyano-5-pyridyl,
2-hydroxy-3-cyano-6-pyridyl,
2-hydroxy-3-nitro-4-pyridyl,
2-hydroxy-3-nitro-5-pyridyl,
2-hydroxy-5-nitro-6-pyridyl,
2-hydroxy-4-nitro-6-pyridyl,
2-hydroxy-5-carboxy-3-pyridyl,
2-hydroxy-5-carboxy-4-pyridyl,
2-hydroxy-5-carboxy-6-pyridyl,
2-hydroxy-3-carboxy-4-pyridyl,
2-hydroxy-5-ethoxycarbonyl-3-pyridyl,
2-hydroxy-5-ethoxycarbonyl-4-pyridyl,
2-hydroxy-5-ethoxycarbonyl-6-pyridyl,
2-hydroxy-3-ethoxycarbonyl-4-pyridyl,
2-hydroxy-3,5-dichloro-4-pyridyl,
2-hydroxy-3,5-dichloro-6-pyridyl,
2-hydroxy-3,5-dibromo-4-pyridyl,
2-hydroxy-3,5-dibromo-6-pyridyl,
2-hydroxy-3-am[no-4-pyridyl,
2-hydroxy-3-amino-5-pyridyl,
2-hydroxy-3-amino-6-pyridyl,
2-hydroxy-3-carbamoyl-4-pyridyl,
2-hydroxy-3-carbamoyl-5-pyridyl, 2-hydroxy-3-carbamoyl-6-pyridyl,
2,4-dihydroxy-6-pyridyl,
2,6-dihydroxy-4-pyridyl,
1-(benzyloxymethyl)-5-chloro-1,2-dihydro-2-oxo-4-pyridyl,
1-(benzyloxymethyl)-5-fluoro-1,2-dihydro-2-oxo-6-pyridyl,
1-(β-phenethyloxymethyl)-5-bromo-1,2-dihydro-2-oxo-4-pyridyl,
1-(2-benzyloxyethyl)-5-chloro-1,2-dihydro-2-oxo-4-pyridyl,
5-fluoro-4-hexanoyloxy-2-pyridyl,
5-chloro-4-hexanoyloxy-2-pyridyl,
5-bromo-4-hexanoyloxy-2-pyridyl,
5-iodo-4-hexanoyloxy-2-pyridyl,
6-benzoyloxy-3-cyano-2-pyridyl,
2-(2-chlorobenzoyloxy)-3-cyano-2-pyridyl,
6-(3-chlorobenzoyloxy)-3-cyano-2-pyridyl,
6-(4-chlorobenzoyloxy)-3-cyano-2-pyridyl,
6-(2-methylbenzoyloxy)-3-cyano-2-pyridyl,
6-(3-methylbenzoyloxy)-3-cyano-2-pyridyl,
6-(4-methylbenzoyloxy)-3-cyano-2-pyridyl,
6-hydroxy-3-cyano-2-pyridyl,
2-hydroxy-3-chloro-6-pyridyl,
6-hydroxy-3-chloro-2-pyridyl,
2-hydroxy-3-fluoro-6-pyridyl,
6-hydroxy-3-fluoro-2-pyridyl and the like.

Arylene groups represented by Y in the pyridyloxycarbonyl arylene carbonyl group of the formula (Y) include divalent groups formed from aromatic hydrocarbons or 5- or 6- membered aromatic heterocyclic ring containing one or two heteroatoms which are the same or different and which is or are selected from the group consisting of nitrogen and oxygen by removing two hydrogen atoms each bonded to the two different carbon atoms. Examples of such arylene groups are phenylene groups such as 1,2-phenylene, 1,3-phenylene, 1,4-phenylene and the like; naphthylene groups such as 1,2-naphthylene, 1,3-naphthylene, 1,4-naphthylene, 1,5-naphthylene, 1,6-naphthylene, 1,7-naphthylene, 1,8-naphthylene and the like; pyridinediyl groups such as 2,3-pyridinediyl, 2,4-pyridinediyl, 2,5-pyridinediyl, 2,6-pyridinediyl, 3,4-pyridinediyl, 3,5-pyridinediyl and the like; pyrazinediyl groups such as 2,3-pyrazinediyl, 2,6-pyrazinediyl, 2,5-pyrazinediyl, and the like; furandiyl groups such as 2,3-furandiyl, 3,4-furandiyl, 2,5-furandiyl, and the like; 4-pyridon-1-lower alkyl-diyl groups such as 4-pyridon-1-methyl-2,3-diyl, 4-pyridon-1-methyl-2,5-diyl, 4-pyridon-1-methyl-2,6-diyl and the like.

Preferable examples of the group of the formula (Y) are those represented by the formula

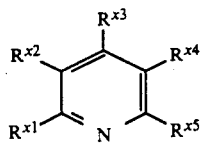
(Y-a)

wherein $R^{x1}$ is hydroxy or acyloxy; $R^{x2}$ and $R^{x4}$ are each hydrogen, halogen, amino, carboxyl, carbamoyl, cyano, nitro, lower alkyl, lower alkenyl or lower alkoxycarbonyl; $R^{x3}$ and $R^{x5}$ are each hydrogen, hydroxy or acyloxy; when at least one of $R^{x1}$, $R^{x3}$ and $R^{x5}$ is free hydroxy, the structure of 1-position on the pyridine ring can be

due to the keto-enol tautomerism, the hydrogen attached to nitrogen being optionally substituted with a substituent selected from the group consisting of lower alkyl, tetrahydrofuranyl, tetrahydropyranyl, lower alkoxy-lower alkyl, phthalidyl, carbamoyl, lower alkoxycarbonyl-lower alkylcarbamoyl, phenyl-lower alkoxy-lower alkyl, phenylcarbamoyl which may have 1 to 3 substituents selected from the group consisting of halogen, lower alkoxy and lower alkyl on the phenyl ring, lower alkylcarbamoyl, carboxy-lower alkylcarbamoyl, lower alkylthiolower alkyl and lower alkenyl, provided that at least one of $R^{x1}$, $R^{x3}$ and $R^{x5}$ represents hydroxy group and that the hydrogen of one hydroxyl group represented by $R^{x1}$, $R^{x3}$ or $R^{x5}$ is substituted with a group

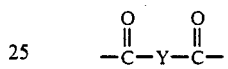

wherein Y is as defined above.

More preferable groups of the formula (Y) are those represented by the formula (Y-a) wherein $R^{x4}$ is halogen, amino, carboxyl, carbamoyl, cyano, nitro, lower alkyl, lower alkenyl or lower alkoxycarbonyl.

The most preferable of the formula (Y) are those represented by the formula (Y-a) wherein $R^{x4}$ is halogen or cyano.

With respect to the phenyl-lower alkyl group having a group $R^xOCO$— on the phenyl ring, examples of the pyridyl group represented by $R^x$ and optionally having the substituents are the same as exemplified above concerning $R^x$ in the pyridyloxycarbonyl arylenecarbonyl group of the formula (Y).

Examples of the phenyl-lower alkyl group having the group $R^xOCO$— on the phenyl ring are as follows.

4-{[(6-benzoyloxy-3-cyano-2-pyridyl)oxy]carbonyl}-benzyl, 4-{[(6-benzoyloxy-3-cyano-2-pyridyl)oxy]carbonyl}-benzyl, 3-{[(6-benzoyloxy-3-cyano-2-pyridyl)oxy]carbonyl}-benzyl, 2-{[(6-benzoyloxy-3-cyano-2-pyridyl)oxy]carbonyl}-benzyl, 2-{4-{[(6-benzoyloxy-3-cyano-2-pyridyl)oxy]carbonyl}phenyl} ethyl, 2-{3-{[(6-benzoyloxy-3-cyano-2-pyridyl)oxy]carbonyl}phenyl} ethyl, 2-{2-{[(6-benzoyloxy-3-cyano-2-pyridyl)oxy]carbonyl}phenyl} ethyl, 1-{4-{[(6-benzoyloxy-3-cyano-2-pyridyl)oxy]carbonyl}phenyl} ethyl, 1-{3-{[(6-benzoyloxy-3-cyano-2-pyridyl)oxy]carbonyl}phenyl} ethyl, 1-{2-{[(6-benzoyloxy-3-cyano-2-pyridyl)oxy]carbonyl}phenyl} ethyl, 3-{4-{[(6-benzoyloxy-3-cyano-2-pyridyl)oxy]carbonyl}phenyl} propyl, 4-{4-{[(6-benzoyloxy-3-cyano-2-pyridyl)oxy]carbonyl} phenyl} butyl, 1,1-dimethyl-2-{4-{[(6-benzoyloxy-3-cyano-2-pyridyl)oxy]carbonyl}-phenyl} ethyl, 5-{4-{[(6-benzoyloxy-3-cyano-2-pyridyl)oxy]carbonyl}phenyl} pentyl, 6-{4-{[(6-benzoyloxy-3-cyano-2-pyridyl)oxy]carbonyl}phenyl} hexyl and the like.

The compounds of the present invention having the group of formula (Y) or the group $R^xOCO$— include ketopenol tautomers. This invention include these tautomers.

Examples of lower alkylene groups represented by A in the group —(A)$_n$B are straight- or branched-chain alkylene groups having 1 to 6 carbon atoms such as methylene, ethylene, trimethylene, 1-methylethylene, tetramethylene, 2-methyltrimethylene, pentamethylene, hexamethylene and the like.

Examples of unsaturated heterocyclic rings in the 5- or 6- membered unsaturated heterocyclic groups represented by B which have 1 to 4 hetero atoms selected from nitrogen, oxygen and sulfur, and which may have benzene ring group, naphthalene ring group or pyridine ring group condensed therewith are pyridine, pyrimidine, pyrazine, pyridazine, 1,3,5-triazine, tetrazole, 1,2,4-triazole, furan, thiophene, isoxazole, oxazole, 1,3,4-thiadiazole, 1,2,4-thiadiazole, 1,2,3-thiadiazole, thiazole, isothiazole, pyrrole, 1,4-dioxine, 1,3-dioxine, 1,2-dioxine, quinoline, isoquinoline, 1,5-naphthyridine, 1,6-naphthyridine, 1,7-naphthyridine, 1,8-naphthyridine, benzofuran, benzothiazole, quinoxaline, quinazoline, cinnoline, phthalazine, β-naphthoquinone, benzo[f]quinoline and the like.

Examples of the above unsaturated heterocyclic groups are 2-pyridyl, 3-pyridyl, 4-pyridyl, 2-pyrimidyl, 4-pyrimidyl, 5-pyrimidyl, 2-pyrazinyl, 3-pyridazinyl, 4-pyridazinyl, 1,3,5-triazine-2-yl, 1H-tetrazole-5-yl, 2H-tetrazole-5-yl, 4H-1,2,4-triazole-3-yl, furan-2-yl, furan3-yl, thiophene-2-yl, thiophene-3-yl, isoxazole-3-yl, isoxazole-4-yl, isoxazole-5-yl, oxazole-2-yl, oxazole-4-yl, oxazole-5-yl, 1,3,4-thiadiazole-2-yl, 1,2,4-thiadiazole-3-yl, 1,2,4-thiadiazole-5-yl, 1,2,3-thiadiazole-4-yl, 1,2,3-thiadiazole-5-yl, thiazole-2-yl, thiazole-4-yl, thiazole-5-yl, isothiazole-3-yl, isothiazole-4-yl, isothiazole-5-yl, pyrrole-2-yl, pyrrole-3-yl, 2H-pyrrole-3-yl, 2H-pyrrole-4-yl, 2H-pyrrole-5-yl, 3H-pyrrole-2-yl, 3H-pyrrole-4-yl, 3H-pyrrole-5-yl, 1,4-dioxine-2-yl, 1,3-dioxine-4-yl, 1,3-dioxine-5-yl, 1,3-dioxine-6-yl, 1,2-dioxine-3-yl, 1,2-dioxine-4-yl, quinoline-2-yl, quinoline-3-yl, quinoline-4-yl, quinoline5-yl, quinoline-6-yl, quinoline-7-yl, quinoline-8-yl, isoquinoline-1-yl, isoquinoline-2-yl, isoquinoline-3-yl, isoquinoline-4-yl, isoquinoline-5-yl, isoquinoline-6-yl, isoquinoline-7-yl, isoquinoline-8-yl, 1,5-naphthyridine-2yl, 1,5-naphthyridine-3-yl, 1,5-naphthyridine-4-yl, 1,6-naphthyridine-2-yl, 1,6-naphthyridine-3-yl, 1,7-naphthyridine-2-yl, 1,7-naphthyridine-5-yl, 1,8-naphthyridine-2-yl, 1,8-naphthyridine-3-yl, 1,8-naphthyridine-4-yl, benzofuran-2-yl, benzofuran-3-yl, benzofuran-4-yl, benzofuran-5-yl, benzofuran-6-yl, benzofuran-7-yl, benzofuran-8-yl, benzothiazole-2-yl, benzothiazole-4-yl, benzothiazole-5-yl, benzothiazole-6yl, benzothiazole-7-yl, quinoxaline-2-yl, quinazoline-2yl, quinazoline-4-yl, quinazoline-5-yl, quinazoline-6-yl, quinazoline-7-yl, quinazoline-8-yl, cinnoline-3-yl, cinnoline-4-yl, cinnoline-5-yl, cinnoline-6-yl, cinnoline7-yl, cinnoline-8-yl, phthalazine-1-yl, phthalazine-5-yl, phthalazine-6-yl, β-naphthoquinoline-1-yl, β-naphthoquinoline-2-yl, β-naphthoquinoline-3-yl, β-naphthoquinoline-5-yl, β-naphthoquinoline-6-yl, β-naphthoquinoline-7-yl, β-naphthoquinoline-8-yl, β-naphthoquinoline-9-yl, β-naphthoquinoline-10-yl, benzo[f]quinoline-2-yl, benzo[f]quinoline-3-yl, benzo[f]quinoline-4-yl, benzo[f]quinoline-5-yl, benzo[f]quinoline-6-yl, benzo[f]quinoline-7-yl, benzo[f]quinoline-8-yl, benzo[f]quinoline-9-yl, benzo[f]quinoline-10-yl and the like.

Examples of substituents which can be bonded to the heterocyclic group are as follows.

(a) Examples of lower alkoxy groups having 1 or 2 phenyl groups optionally substituted with halogen or lower alkoxy on the phenyl ring are $C_1$-$C_6$ alkoxy groups having 1 or 2 phenyl groups optionally substituted with halogen or $C_1$-$C_6$ alkoxy on the phenyl ring such as benzyloxy, α-phenethyloxy, β-phenethyloxy, 2-phenylpropoxy, 2-phenyl-2-methyl-propoxy, 4-phenylbutoxy, 3-phenylpentyloxy, 4-phenylhexyloxy, diphenylmethoxy, 1,2-diphenylbutoxy, 2,4-diphenylpentyloxy, 3,6-diphenylhexyloxy, 2-methoxybenzyloxy, 3-methoxybenzyloxy, 4-methoxybenzyloxy, 2,3-dimethoxybenzyloxy, 2,4-dimethoxybenzyloxy, 2,4,5-trimethoxybenzyloxy, α-(2-ethoxy)phenethyloxy, β-(3-propoxy)phenethyloxy, 3-(4-t-butoxy)phenylpropoxy, di-(2-methoxybenzyl)methoxy, 1,2-di-(2-methoxyphenyl)ethoxy, 4-chlorobenzyloxy, 4-fluorobenzyloxy, 4-bromobenzyloxy, 4-iodobenzyloxy, 3-chlorobenzyloxy, 2-chlorobenzyloxy, 2-bromobenzyloxy, 2,4-dichlorobenzyloxy, 3,4,5-trichlorobenzyloxy, α-(4-chlorophenyl)ethoxy, β-(4-chlorophenyl)-ethoxy, 3-(3-chlorophenyl)propoxy, [1,1-dimethyl-2-(4-chlorophenyl)} ethoxy, 4-(4-bromophenyl)butoxy, 6-(4-chlorophenyl)hexyloxy, di-(4-chlorobenzyl)methoxy, di-(2-chlorobenzyl)methoxy, 1,2-di-(4-chlorophenyl)ethoxy and the like. (b) Examples of phenoxy groups optionally substituted with halogen or lower alkoxy on the phenyl ring are phenoxy groups optionally substituted with 1 to 3 halogen atoms or $C_1$-$C_6$ lower alkoxy groups on the phenyl ring such as phenoxy, 2-fluorophenoxy, 3-fluorophenoxy, 4-fluorophenoxy, 2-chlorophenoxy, 3-chlorophenoxy, 4-chlorophenoxy, 3-bromophenoxy, 4-iodophenoxy, 2,3-dichlorophenoxy, 2,4-dichlorophenoxy, 3,5-difluorophenoxy, 3,4,5-trichlorophenoxy, 2,4,6-tribromophenoxy, 2-methoxyphenoxy, 3-methoxyphenoxy, 4-methoxyphenoxy, 2,4-dimethoxyphenoxy, 2,6-dimethoxyphenoxy, 3,4,5-trimethoxyphenoxy, 2,4,6-trimethoxyphenoxy, 3-ethoxyphenoxy, 4-tbutoxyphenoxy, 4-pentyloxyphenoxy, 4-hexyloxyphenoxy and like.

Examples of lower alkanoyl groups in lower alkanoyloxy groups are straight- or branched-chain alkanoyl groups having 1 to 6 carbon atoms such as formyl, acetyl, propanoyl, butanoyl, isobutanoyl, pentanoyl, hexanoyl and the like.

(d) Examples of phenyl-lower alkyl groups in phenyl-lower alkylthio groups are straight- or branched-chain phenyl-lower alkyl groups having 1 to 6 carbon atoms such as benzyl, 1-phenylethyl, 2-phenylethyl, 2-phenyl-1-methylethyl, 2-phenypropyl, 3-phenypropyl, 4-phenylbutyl, 2-phenyl-1,1-dimethylethyl, 5-phenylpentyl, 6-phenylhexyl and the like.

The heterocyclic groups having specific substituents, i.e. 1 to 3 substituents selected from the group consisting of hydroxy group, cyano group, halogen atom, lower alkyl group, lower alkoxy group, phenyl group, lower alkoxy group having 1 or 2 phenyl groups optionally substituted with halogen or lower alkoxy on the phenyl ring, phenoxy group optionally substituted with halogen or lower alkoxy on the phenyl ring, nitro group, oxo group, benzoyloxy group, lower alkoxycarbonyl group, lower alkanoyloxy group, phenyl-lower alkylthio group and the group $R^x$OCO-($R^x$ is as defined above.) are as follows.

6-benzyloxy-pyridine-2-yl, 5-benzyloxy-pyridine-2-yl, 4-benzyloxy-pyridine-2-yl, 3-benzyloxy-pyridine-2-yl, 6-benzyloxy-pyridine-3-yl,
6-(β-phenethyloxy)-pyridine-2-yl,
4-(α-phenethyloxy)-pyridine-2-yl,
4,6-di(benzyloxy)-pyridine-2-yl,
3,4,5-tri(benzyloxy)-pyridine-2-yl,
6-hydroxy-pyridine-2-yl, 5-hydroxy-pyridine-2-yl, 4-hydroxy-pyridine-2-yl, 3-hydroxy-pyridine-2-yl,
6-hydroxy-pyridine-3-yl, 6-hydroxy-pyridine-4-yl,
4,6-dihydroxy-pyridine-2-yl, 3,5-dihydroxy-pyridine-2-yl,
3,4,5-trihydroxy-pyridine-2-yl,
6-hydroxy-3-cyano-pyridine-2-yl,
6-hydroxy-4-cyano-pyridine-2-yl,
6-hydroxy-5-cyano-pyridine-2-yl,
2-hydroxy-3-cyano-pyridine-5-yl,
2-hydroxy-5-cyano-pyridine-3-yl,
2-chloro-pyridine-6-yl, 3-chloro-pyridine-6-yl,
4-chloro-pyridine-2-yl, 3-chloro-pyridine-2-yl,
2-chloro-pyridine-4-yl, 2-bromo-pyridine-6-yl,
2-bromo-pyridine-4-yl, 2-fluoro-pyridine-6-yl,
2-fluoro-pyridine-4-yl, 2-chloro-pyridine-5-yl,
2,5-dichloro-pyridine-4-yl, 2,6-dichloro-pyridine-4-yl,
3,5-dichloro-pyridine-4-yl,
2-chloro-5-bromo-pyridine-4-yl,
2,5-dibromo-pyridine-4-yl, 2,5-dichloro-pyridine-6-yl,
2,5,6-trichloro-pyridine-4-yl,
3,4,5-tribromo-pyridine-2-yl,
6-methoxy-pyridine-2-yl, 5-methoxy-pyridine-2-yl,
6-methoxy-pyridine-3-yl, 6-methoxy-pyridine-4-yl,
4-methoxy-pyridine-2-yl, 3-methoxy-pyridine-2-yl,
4-ethoxy-pyridine-2-yl, 5-ethoxy-pyridine-2-yl,
6-ethoxy-pyridine-2-yl, 4-t-butoxy-pyridine-2-yl,
6-t-butoxy-pyridine-2-yl, 6-pentyloxy-pyridine-2-yl,
4-pentyloxy-pyridine-2-yl, 3-pentyloxy-pyridine-2-yl,
4,6-dimethoxy-pyridine-2-yl, 3,6-dimethoxy-pyridine-2-yl,
4,6-diethoxy-pyridine-2-yl, 4,6-dipentyloxy-pyridine-2-yl,
3,4,5-trimethoxy-pyridine-2-yl,
4,5,6-trimethoxy-pyridine-2-yl,
3,4,5-triethoxy-pyridine-2-yl,
6-methyl-pyridine-2-yl, 6-methyl-pyridine-4-yl,
5-methyl-pyridine-2-yl, 4-methyl-pyridine-2-yl,
4-ethyl-pyridine-2-yl, 6-t-butyl-pyridine-2-yl,
4,6-dimethyl-pyridine-2-yl, 4,6-dimethyl-pyridine-3-yl,
3,4,5-trimethyl-pyridine-2-yl,
3,4,5-triethyl-pyridine-2-yl,
6-nitro-pyridine-2-yl, 5-nitro-pyridine-2-yl,
2-nitro-pyridine-4-yl, 4-nitro-pyridine-2-yl,
4,6-dinitro-pyridine-2-yl, 3,4,5-trinitro-pyridine-2-yl,
3-cyano-6-benzyloxy-pyridine-2-yl,
4-cyano-6-benzyloxy-pyridine-2-yl,
3-cyano-5-benzyloxy-pyridine-2-yl,
5-cyano-3-benzyloxy-pyridine-2-yl,
3-cyano-6-benzyloxy-pyridine-4-yl,
2-cyano-6-benzyloxy-pyridine-4-yl,
3-cyano-6-(α-phenethyloxy)-pyridine-2-yl,
3-cyano-6-(β-phenethyloxy)-pyridine-2-yl,
5-cyano-6-methoxy-pyridine-2-yl,
4-cyano-6-methoxy-pyridine-2-yl,
3-cyano-6-methoxy-pyridine-2-yl,
5-cyano-6-ethoxy-pyridine-2-yl,
4-cyano-6-ethoxy-pyridine-2-yl,
3-cyano-6-ethoxy-pyridine-2-yl,
5-cyano-6-ethoxy-pyridine-3-yl,
5-cyano-3-ethoxy-pyridine-2-yl,
3-cyano-6-benzoyloxy-pyridine-2-yl,
4-cyano-6-benzoyloxy-pyridine-2-yl,
5-cyano-6-benzoyloxy-pyridine-2-yl,
3-cyano-4-benzoyloxy-pyridine-3-yl,
6-cyano-4-benzoyloxy-pyridine-2-yl,
6-phenoxy-pyridine-2-yl, 2-phenoxy-pyridine-4-yl,
5-phenoxy-pyridine-2-yl, 5-phenoxy-pyridine-3-yl,
4-phenoxy-pyridine-2-yl, 4,6-diphenoxy-pyridine-2-yl,
2,6-diphenoxy-pyridine-4-yl,
3,4,5-triphenoxy-pyridine-2-yl,
6-(4-methoxyphenoxy)-pyridine-2-yl,
2-(4-methoxyphenoxy)-pyridine-4-yl,
6-(3-methoxyphenoxy)-pyridine-3-yl,
6-(2-methoxyphenoxy)-pyridine-2-yl,
6-(4-ethoxyphenoxy)-pyridine-2-yl,
6-(4-t-butoxyphenoxy)-pyridine-2-yl,
6-(3,5-dimethoxyphenoxy)-pyridine-2-yl,
4-(4-methoxyphenoxy)-pyridine-2-yl,
4,6-di-(4-methoxyphenoxy)-pyridine-2-yl,
6-benzyloxy-5-chloro-pyridine-2-yl,
4-benzyloxy-5-chloro-pyridine-2-yl,
3-benzyloxy-5-chloro-pyridine-2-yl,
6-benzyloxy-4-chloro-pyridine-2-yl,
6-benzyloxy-5-bromo-pyridine-2-yl,
6-benzyloxy-5-chloro-pyridine-3-yl,
6-(α-phenetyloxy)-5-chloro-pyridine-2-yl,
6-(β-phenetyloxy)-5-chloro-pyridine-2-yl,
6-(4-chloro-benzyloxy)-pyridine-2-yl,
6-(3-chloro-benzyloxy)-pyridine-2-yl,
6-(4-fluoro-benzyloxy)-pyridine-2-yl,
6-(4-bromo-benzyloxy)-pyridine-2-yl,
2-(4-chloro-benzyloxy)-pyridine-5-yl,
2-(4-chloro-benzyloxy)-pyridine-4-yl,
4-(4-chloro-benzyloxy)-pyridine-2-yl,
5-(4-chloro-benzyloxy)-pyridine-2-yl,
6-methoxy-5-chloro-pyridine-2-yl,
6-methoxy-4-chloro-pyridine-2-yl,
6-ethoxy-5-chloro-pyridine-2-yl,
6-ethoxy-4-bromo-pyridine-2-yl,
6-ethoxy-5-chloro-pyridine-3-yl,
6-chloro-5-ethoxy-pyridine-2-yl,
6-chloro-4-ethoxy-pyridine-2-yl,
6-methoxycarbonyl-pyridine-2-yl,
6-methoxycarbonyl-pyridine-4-yl,
6-ethoxycarbonyl-pyridine-2-yl,
6-(n-propoxycarbonyl)-pyridine-2-yl,
6-(t-butoxycarbonyl)-pyridine-2-yl,
5-ethoxycarbonyl-pyridine-2-yl,
4-methoxycarbonyl-pyridine-2-yl,
4-ethoxycarbonyl-pyridine-2-yl,
2-methoxycarbonyl-pyridine-4-yl,
6-benzhydryloxy-pyridine-2-yl,
6-benzhydryloxy-pyridine-4-yl,
5-benzhydryloxy-pyridine-2-yl,
4-benzhydryloxy-pyridine-2-yl,
3-benzhydryloxy-pyridine-2-yl,
6-trityloxy-pyridine-2-yl, 4-trityloxy-pyridine-2-yl,
6-(2,2-diphenyl)ethoxy-pyridine-2-yl,
6[(3,3,3-triphenyl)-n-propoxy]-pyridine-2-yl,
6-acetyloxy-pyridine-2-yl, 6-acetyloxy-pyridine-4-yl,
5-acetyloxy-pyridine-2-yl, 4-acetyloxy-pyridine-2-yl,
3-acetyloxy-pyridine-2-yl, 6-propionyloxy-pyridine-2-yl,
4-propionyloxy-pyridine-2-yl,
6-benzylthio-pyridine-2-yl, 5-benzylthio-pyridine-2-yl,
4-benzylthio
6-(β-phenethyl)thio-pyridine-2-yl,
5-(β-phenethyl)thio-pyridine-3-yl,
6-benzylthio-pyridine-4-yl,
6-isobutyryloxy-pyridine-2-yl,
5-isobutyryloxy-pyridine-2-yl,
6-valeryloxy-pyridine-2-yl,
6-(4-methoxy-benzyloxy)-pyridine-2-yl,
6-(2-methoxy-benzyloxy)-pyridine-2-yl,
6-(4-ethoxy-benzyloxy)-pyridine-2-yl,
6-(4-methoxy-benzyloxy)-pyridine-4-yl, 6-[4-(n-propoxy-benzyloxy)]-pyridine-2-yl,
5-(4-methoxy-benzyloxy)-pyridine-2-yl,
4-(4-methoxy-benzyloxy)-pyridine-2-yl,
4-methyl-1,2,4-triazole-5-yl, 4-ethyl-1,2,4-triazole-5-yl,
4-(n-propyl)-1,2,4-triazole-5-yl,
4-(t-butyl)-1,2,4-triazole-5-yl,
4-pentyl-1,2,4-triazole-5-yl, 4-hexyl-1,2,4-triazole-5-yl,
6-methoxy-pyridazine-3-yl, 6-ethoxy-pyridazine-3-yl,
6-(n-propoxy)-pyridazine-3-yl,
6-(n-butoxy)-pyridazine-3-yl,
6-(t-butoxy)-pyridazine-3-yl,
6-pentyloxy-pyridazine-3-yl, 6-hexyloxy-pyridazine-3-yl,
6-methoxy-pyridazine-4-yl, 6-methoxy-pyridazine-5-yl,
6-chloro-pyridazine-3-yl, 6-bromo-pyridazine-3-yl,
6-fluoro-pyridazine-3-yl, 6-iodo-pyridazine-3-yl,
6-chloro-pyridazine-4-yl, 6-chloro-pyridazine-5-yl,
4-methoxy-pyrimidine-6-yl, 2-ethoxy-pyrimidine-4-yl,
2,4-diethoxy-pyrimidine-6-yl,
2,4-[di-(n-propoxy)]-pyrimidine-6-yl,
2-methoxy-4-ethoxy-pyrimidine-6-yl,
4,6-dimethoxy-pyrimidine-2-yl,
1,3-dimethyluracil-6-yl, 1,3-diethyluracil-6-yl,
1-methyl-3-ethyluracil-6-yl,
2,4-dimethoxy-1,3,5-triazine-6-yl,
2,4-diethoxy-1,3,5-triazine-6-yl,
2,4-di(n-propoxy)-1,3,5-triazine-6-yl,
2-methoxy-4-ethoxy-1,3,5-triazine-6-yl, pyridine-N-oxide-2-yl, pyridine-N-oxide-3-yl, pyridine-N-oxide-4-yl,
2,4-dibenzyloxy-5-chloro-pyrimidine-6-yl,
2,4-dibenzyloxy-5-bromo-pyrimidine-6-yl,
2,4-dibenzyloxy-5-fluoro-pyrimidine-6-yl,
2,4-dibenzyloxy-5-iodo-pyrimidine-6-yl,
2,4-di(s-phenethyloxy)-5-chloro-pyrimidine-6-yl,
2-benzyloxy-4-(β-phenethyloxy)-5-chloro-pyrimidine-6-yl,
3-methoxy-quinoxaline-2-yl, 2-ethoxy-quinoxaline-3-yl,
2-(n-propoxy)-quinoxaline-3-yl,
2-(n-butoxy)-quinoxaline-3-yl,
2-(tert-butoxy)-quinoxaline-3-yl,
2-pentyloxy-quinoxaline-3-yl, 2-hexyloxy-quinoxaline-3-yl,
5-methoxy-quinoxaline-3-yl, 8-methoxy-quinoxaline-3-yl,
2-chloro-quinoxaline-3-yl, 2-bromo-quinoxaline-3-yl,
2-fluoro-quinoxaline-3-yl, 2-iodo-quinoxaline-3-yl,
5-chloro-quinoxaline-3-yl, 7-chloro-quinoxaline-3-yl,
1-phenyl-l(H)-tetrazole-5-yl,
3-chloro-isoquinoline-1-yl, 3-bromo-isoquinoline-1-yl,
3-fluoro-isoquinoline-1-yl, 3-iodo-isoquinoline-1-yl,
4-chloro-isoquinoline-1-yl, 5-chloro-isoquinoline-1-yl,
1-chloro-isoquinoline-4-yl,
4-chloro-quinoline-2-yl, 4-bromo-quinoline-2-yl,
4-fluoro-quinoline-2-yl, 4-iodo-quinoline-2-yl,
5-chloro-quinoline-2-yl, 7-chloro-quinoline-2-yl,
2-chloro-quinoline-4-yl, 4-methoxy-quinoline-2-yl,
5-methoxy-quinoline-2-yl, 8-methoxy-quinoline-2-yl,
4-ethoxy-quinoline-2-yl, 8-ethoxy-quinoline-2-yl,
4-(n-propoxy)-quinoline-2-yl, 4-(t-butoxy)-quinoline-2-yl,
2-methoxy-quinoline-4-yl, 2-ethoxy-quinoline-4-yl,
5-(6-benzoyloxy-3-cyano-2-pyridyloxycarbonyl)-furan-2-yl,
4-(6-benzoyloxy-3-cyano-2-pyridyloxycarbonyl)-furan-2-yl,
3-(6-benzoyloxy-3-cyano-2-pyridyloxycarbonyl)-furan-2-yl,
5-(2-pyridyloxymethyl)-furan-2-yl,
4-(2-pyridyloxymethyl)-furan-2-yl,
3-(2-pyridyloxymethyl)-furan-2-yl
5-(6-benzoyloxy-3-cyano-2-pyridyloxycarbonyl)thiophene-2-yl,
4-(6-benzoyloxy-3-cyano-2-pyridyloxycarbonyl)thiophene-2-yl,
3-(6-benzoyloxy-3-cyano-2-pyridyloxycarbonyl)-thiophene-2-yl,
5-(2-pyridyloxymethyl)-thiophene-2-yl,
4-(2-pyridyloxymethyl)-thiophene-2-yl,
3-(2-pyridyloxymethyl)-thiophene-2-yl,
2-chloro-5-thienylmethyl, 3-chloro-5-thienylmethyl,
4,5-dichloro-2-thienylmethyl,
3,5-dichloro-2-thienylmethyl,
3,4,5-trichloro-2-thienylmethyl,
2-bromo-5-thienylmethyl, 5-fluoro-2-thienylmethyl,
3-bromo-5-thienylmethyl, 3-fluoro-5-thienylmethyl,
2-methyl-5-thienylmethyl, 2-ethyl-5-thienylmethyl,
2-propyl-5-thienylmethyl, 2-butyl-5-thienylmethyl,
2-(t-butyl)-5-thienylmethyl, 2-pentyl-5-thienylmethyl,
2-hexyl-5-thienylmethyl, 3-methyl-5-thienylmethyl,
3-propyl-5-thienylmethyl, 3-hexyl-5-thienylmethyl,
2-carboxy-5-thienylmethyl, 3-carboxy-5-thienylmethyl,
2-pyridyl-methyl, 3-pyridyl-methyl, 4-pyridyl-methyl,
1-(4-pyridyl)-ethyl, 2-(4-pyridyl)-ethyl,
3-(4-pyridyl)-propyl, 4-(4-pyridyl)-butyl,
1,1-dimethyl-2-(4-pyridyl)-ethyl,
5-(4-pyridyl)-pentyl, 6-(4-pyridyl)-hexyl,
2-(3-pyridyl)-ethyl, 4-(3-pyridyl)-butyl,
6-(3-pyridyl)-hexyl, 2-furanyl-methyl,
3-furanyl-methyl, 2-(2-furanyl)-ethyl,
2-(3-furanyl)-ethyl, 3-(2-furanyl)-propyl,
1-methyl-2-(2-furanyl)-ethyl, 4-(2-furanyl)-butyl,
5-(2-furanyl)-pentyl, 6-(2-furanyl)-hexyl,
2-thienyl-methyl, 3-thienyl-methyl, 2-(2-thienyl)-ethyl,
3-(2-thienyl)-propyl, 1-methyl-2-(2-thienyl)-propyl
4-(2-thienyl)-butyl, 1,1-dimethyl-2-(2-thienyl)-ethyl,
5-(2-thienyl)-pentyl, 6-(2-thienyl)-hexyl,
3-(3-thienyl)-propyl, 6-(3-thienyl)-hexyl,
(6-chloro-3-pyridyl)methyl, (6-bromo-3-pyridyl)methyl,
(6-fluoro-3-pyridyl)methyl, (6-iodo-3-pyridyl)methyl,
(6-chloro-4-pyridyl)methyl, (2-chloro-3-pyridyl)methyl,
2-(6-chloro-3-pyridyl)ethyl, (2-bromo-3-pyridyl)methyl,
1,1-dimethyl-2-(6-chloro-3-pyridyl)ethyl,
4-(6-chloro-3-pyridyl)butyl, 5-(6-chloro-3-pyridyl)pentyl,
6-(6-chloro-3-pyridyl)hexyl, 2-(2-chloro-3-pyridyl)ethyl,
3-(2-chloro-3-pyridyl)propyl, 4-(2-chloro-3-pyridyl)butyl,
5-(2-chloro-3-pyridyl)pentyl, 6-(2-chloro-3-pyridyl)hexyl,
2-quinolyl-methyl, 3-quinolyl-methyl, 4-quinolyl-methyl,
5-quinolyl-methyl, 6-quinolyl-methyl, 7-quinolyl-methyl,
8-quinolyl-methyl, 2-(2-quinolyl)-ethyl,
3-(2-quinolyl)-propyl, 1,1-dimethyl-2-(2-quinolyl)-ethyl,
4-(2-quinolyl)-butyl, 5-(2-quinolyl)-pentyl,
6-(2-quinolyl)-hexyl, 2-benzofuranyl-methyl,
2-(2-benzofuranyl)-ethyl, 3-(2-benzofuranyl)-propyl,
1,1-dimethyl-2-(2-benzofuranyl)-ethyl,
4-(2-benzofuranyl)-butyl, 5-(2-benzofuranyl)-pentyl, 6-(2-benzofuranyl)-hexyl, 3-benzofuranyl-methyl, 2-(3-benzofuranyl)-ethyl, 3-(3-benzofuranyl)-propyl, 6-(3-benzofuranyl)-hexyl and the like.

Examples of groups contained in the compound of formula (1β) are described below.

Examples of phenyl lower alkoxy-lower alkyl groups are phenylalkoxyalkyl group in which the alkoxy moiety and alkyl moiety each have 1 to 6 carbon atoms, specific examples of the phenylalkoxyalkyl groups being the same as described above as the substituents in the substituted pyridyl groups represented by $R^x$.

Examples of thienyl-lower alkyl groups optionally substituted with halogen atom on the thienyl ring are thienyl-$C_1$-$C_6$ alkyl groups optionally substituted with one or two halogen atoms such as (2-thienyl)methyl, (3-thienyl)ethyl, (5-chloro-2-thienyl)methyl, (3-chloro-2-thienyl)methyl, (4-chloro-2-thienyl)methyl, (3,5-dichloro2-thienyl)methyl, (4,5-dichloro-2-thienyl)-methyl, (5-bromo-2-thienyl)methyl, (5-chloro-2-thienyl)methyl and the like.

The 5-fluorouracil derivatives of the present invention can be prepared by various processes.

The compounds of the formula (1α) according to the present invention can be prepared by the processes represented by the following reaction schemes (a) to (d).

Reaction scheme (a)

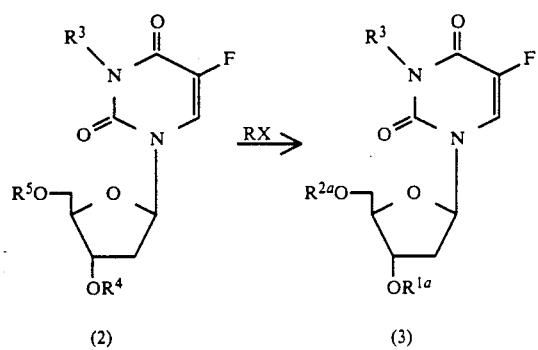

wherein $R^3$ is as defined above, one of $R^4$ and $R^5$ is a hydrogen atom and the other is a hydrogen atom, acyl group or protective group, R is the phenyl-lower alkyl group having a group $R^xOCO-$ ($R^x$ is as defined above) on the phenyl ring or the group $-(A)_nB$ (wherein A, B and n are as defined above), $R^{1a}$ and $R^{2a}$ are each a hydrogen atom, acyl group or the group R, with the proviso that when $R^{1a}$ is a hydrogen atom or acyl group, $R^{2a}$ is not a hydrogen atom nor acyl group, and X is a halogen atom.

The protective groups represented by $R^4$ or $R^5$ include the following groups.

(A) Triaryl-substituted methyl groups represented by the formula

wherein Ar is aryl. Examples of such group are methyl group substituted with three aryl groups such as phenyls which may have halogen atom, nitro, lower alkyl or lower alkoxy as the substituent.

(B) Cyclic ether residue groups represented by the formula

wherein R' is a lower alkyl, and n is 2 or 3. Examples of such groups are 2-tetrahydrofuranyl, 2-tetrahydropyranyl, etc.

(C) Lower alkoxymethyl groups such as methoxymethyl, ethoxymethyl and hexyloxymethyl.

(D) Tri(lower alkyl)silyl groups such as trimethylsilyl and t-butyldimethylsilyl.

(E) Benzyl group.

The present reaction is conducted by reacting a compound of the formula (2) (hereinafter referred to as "compound (2)") with a halide (RX) to substitute the desired group R for the hydrogen atom of the hydroxyl group at the 3'- or 5'-position of the compound (2), followed by a reaction for removing the protective group or acyl when required, to obtain a compound (3).

The reaction for introducing the group R is conducted under the usual reaction conditions for dehydrohalogenation. The dehydrohalogenation agent to be used can be any of various basic compounds which are generally used for such reactions. Examples of useful compounds are sodium hydroxide, potassium hydroxide, sodium carbonate, potassium carbonate, sodium hydrogencarbonate, potassium hydrogencarbonate, alkali metals such as sodium and potassium, alkali metal hydrides such as sodium hydride and potassium hydride, etc.

The reaction can be conducted in the presence of a solvent or in the absence thereof. Examples of useful solvents are usual inert solvents such as, ethers such as tetrahydrofuran (THF) and dioxane, aromatic hydrocarbons such as benzene, toluene, xylene and chlorobenzene, ketones such as acetone and methyl ethyl ketone, nitriles such as acetonitrile and propionitrile, dimethylsulfoxide, dimethylacetamide, dimethylformamide, etc.

While the ratio of the halide (RX) to the compound (2) is not limited specifically but is widely variable, usually at least about 1 mole, preferably about 1 to about 5 moles, of the former is used per mole of the latter. The reaction temperature is not limited specifically either but is widely variable. It is, however, usually 0 to 100° C., preferably room temperature to 80° C. The reaction is completed usually in about 30 minutes to about 64 hours, preferably about 1 to about 5 hours.

When the compound obtained by the above reaction has a protective group at the 3'- or 5'-position, the desired compound (3) can be obtained by subsequently subjecting the product to a reaction for removing the protective group. This reaction is carried out usually in a solvent, using a suitable amount of a catalyst which is commonly used for acid hydrolysis reactions. Examples of suitable catalysts are inorganic acids including hydrochloric acid, sulfuric acid and perchloric acid, and organic acids including lower alkanoic acids such as formic acid, acetic acid and propionic acid, benzoic acid, organosulfonic acids such as methanesulfonic acid, ethanesulfonic acid, benzenesulfonic acid and 4-methylbenzenesulfonic acid. Examples of useful solvents are usual inert solvents including water, lower alcohols such as methanol, ethanol and isopropanol, ketones such as acetone and methyl ethyl ketone, ethers such as diethyl ether, THF and dioxane, aromatic hydrocarbons such as benzene, toluene, xylene and chlorobenzene, lower alkanoic acids such as acetic acid and propionic acid, dimethylsulfoxide, dimethylacetamide, dimethylformamide and mixtures of such solvents. The reaction temperature is not limited specifically but is suitably determined over a wide range. Usually it is 0° to 100° C., preferably room temperature to about 80° C. The reaction takes about 3 minutes to about 20 hours. The acid is usually used in a catalytic amount to an excessive amount, preferably in an excessive amount. When the protective group is benzyl, the benzyl group can be removed by usual catalytic reduction. Examples of catalysts useful in such reduction are platinum oxide, palladium-carbon, palladium-black, palladium-barium sulfate, palladium-barium carbonate, raney-nickel, etc. The catalytic reduction is carried out by hydrogenation in the presence of such catalyst. The amount of catalyst to be used is not limited specifically, but usually about 5 to about 15 percent by weight based on the starting compound. Useful solvents are usual inert solvents, and include alcohols such as methanol, ethanol and propanol, ethers such as diethyl ether, tetrahydrofuran and dioxane, esters such as methyl acetate and ethyl acetate, and aprotic polar solvents such as dimethylformamide and dimethylactamide, and mixtures of such solvents.

When the compound (3) prepared by the process of the scheme (a) has acyl at at least one of the 3-, 3'- and 5'-positions, the compound is subjected to a hydrolysis reaction, whereby one or all of the acyl groups can be converted to hydrogen. The hydrolysis reaction is carried out under the usual conditions for acid or alkali hydrolysis. The catalyst to be used for the hydrolysis reaction can be any one of those which are commonly used for acid or alkali hydrolysis. Typical of these catalysts are basic compounds such as sodium hydroxide, potassium hydroxide and barium hydroxide, and inorganic acids such as hydrochloric acid, sulfuric acid and nitric acid. The amount of catalyst to be used is not limited specifically but is suitably variable over a wide range. Generally, the reaction proceeds advantageously in a solvent. A wide variety of usual inert solvents are usable for this purpose. Examples of useful solvents are water, lower alcohols such as ethanol, methanol and isopropanol, ketones such as acetone and methyl ethyl ketone, and mixtures of such solvents. The reaction temperature is not limited specifically but is suitably determined over a wide range. It is usually 0° to 100° C., preferably room temperature to about 80° C. The reaction takes about 30 minutes to about 10 hours.

Reaction scheme (b)

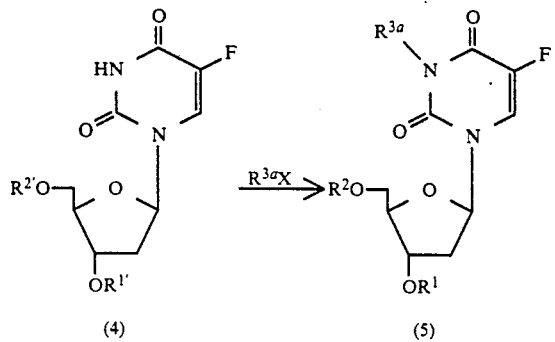

(4)    (5)

wherein one of $R^{1'}$ and $R^{2'}$ is the same as the group R defined above, the other is a hydrogen atom, acyl or a protective group, $R^{3a}$ is acyl, and $R^1$ and $R^2$ are as defined above.

The present reaction, wherein acyl is introduced into the 3-position of the pyrimidine moiety (acylation), can be conducted by a usual process, e.g., the acid chloride method. With the acid chloride method, an acyl halide ($R^{3a}X$) is caused to act on the compound (4) in a suitable solvent in the presence of a acid scavenger to give the desired compound (5). Examples of useful acid scavengers are sodium hydrogen carbonate, sodium carbonate, potassium carbonate, pyridine, triethylamine, etc. Examples of useful solvents are benzene, chloroform, methylene chloride, carbon tetrachloride, dioxane, tetrahydrofuran, etc. The acyl halide is used in an amount of at least about one mole, preferably about 1 to about 3 moles, per mole of the compound (4). The reaction temperature is usually $-30$ to 100° C., preferably room temperature to about 80° C. The reaction takes about 20 minutes to about 20 hours.

When the compound (4) to be reacted has a free hydroxyl group at its 3'- or 5'-position, acylation takes place also at such position simultaneously with acylation at the 3-position. Accordingly, it is desirable to protect the hydroxyl group at the 3'- or 5'-position before acylation and to remove the protective group after the acylation. The reaction for introducing the protective group will be described later. The reaction to remove the protective group can be carried out by the same method as already described for the reaction scheme (a).

Reaction scheme (c)

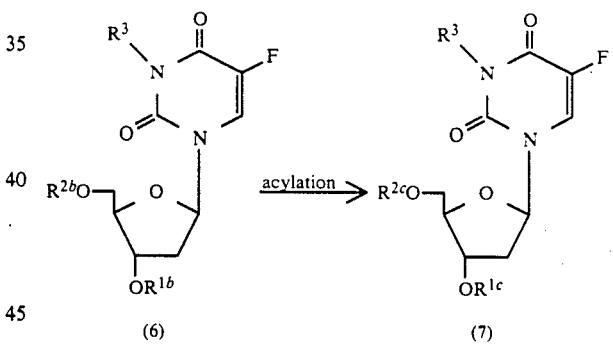

(6)    (7)

wherein one of $R^{1b}$ and $R^{2b}$ is a hydrogen atom, the other is the same as the group R defined above, one of $R^{1c}$ and $R^{2c}$ is acyl, the other is the same as the group R defined above, and $R^3$ is as defined above.

The free hydroxyl group at the 3'- or 5'position of the compound (6) is acylated to afford a compound (7) For the acylation reaction, any of usual acylation method are usable, such as the acid chloride method, acid anhydride method, mixed acid anhydride method, N,N'-dicyclohexylcarbodiimide method (DCC method), etc., among which the acid anhydride method and acid chloride method are advantageous.

The acid anhydride method is conducted by reacting the compound (6) with an acid anhydride in a suitable solvent. The acid anhydride to be used is the anhydride of an acid corresponding to the acyl group to be introduced into the 3'- or 5'-position. Examples of such anhydrides are acetic anhydride, propionic anhydride, butyric anhydride, benzoic anhydride, etc. These acid anhydrides are used in an amount of at least one mole, preferably about 1 to about 3 moles, per mole of the compound (6). Examples of useful solvents are various inert solvents including pyridine, hydrocarbon halides such as chloroform and dichloromethane, ethers such as dioxane and THF, aromatic hydrocarbons such as benzene and toluene, dimethylformamide (DMF), dimethyl sulfoxide (DMSO), acetonitrile, etc. The reaction temperature is usually about −30° C. to about 100° C., preferably room temperature to about 80° C. The reaction takes about 20 minutes to about 20 hours. The reaction can be carried out advantageously in the presence of a basic compound. Examples of useful basic compounds are organic bases such as pyridine, triethylamine, N,N-dimethylaniline and like tertiary amines, and inorganic basic compounds such as sodium hydrogen-carbonate, potassium carbonate and sodium acetate.

The acid chloride method is practiced by causing an acyl halide ($R^{3a}X$) to act on the compound (6) in a suitable solvent in the presence of an acid scavenger, in the same manner as described for the reaction scheme (b).

When the reagent, i.e., the acid halide is used in an amount of at least two moles per mole of the starting compound for the processes of the reaction schemes (b) and (c), the reactions may give an O- and N-diacylated compound wherein the 3′- or 5′-position and the 3-position are acylated respectively at the same time. The O- and N-diacylated compound can be easily separated from the O-acylated compound or N-acylated compound.

Reaction scheme (d)

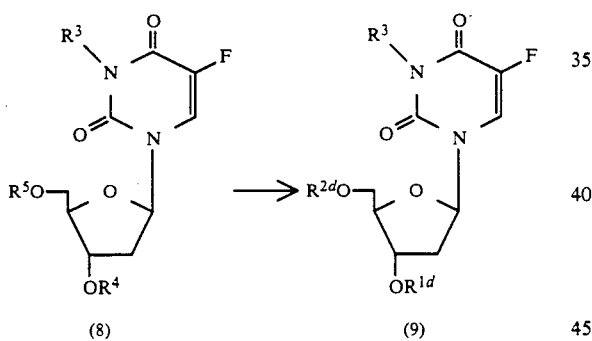

wherein $R^3$, $R^4$ and $R^5$ are as defined above, and $R^{1d}$ and $R^{2d}$ are each a hydrogen atom, acyl or phenyl-lower alkyl having a group $R^xOCO-$ (wherein $R^x$ is as defined above) on the phenyl ring. However, when $R^{1d}$ is a hydrogen atom or acyl, $R^{2d}$ is not a hydrogen atom nor acyl.

The reaction is conducted by introducing into the compound (8) phenyl-lower alkyl having carboxyl on the phenyl ring in the same manner as the reaction scheme (a), and condensation is effected between the compound obtained and $R^x$-OH using a dehydrating agent such as N,N′-dicyclohexylcarbodiimide, followed, when required, by a reaction for removing the protective group or acyl in the same manner as in the reaction scheme (a), whereby the compound (9) is produced.

The 5-fluorouracil derivatives (1α) of the invention prepared by the above processes easily isolated and purified by usual separation methods such as reprecipitation, recrystallization, silica gel chromatography, ion-exchange chromatography, gel chromatography, affinity chromatography and the like.

The starting compounds to be used in the above reaction schemes (a) to (d) are prepared by processes as described in the following reaction schemes (e) to (g).

Reaction scheme (e)

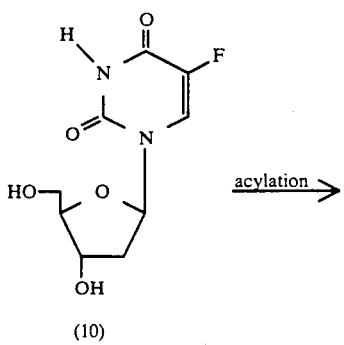

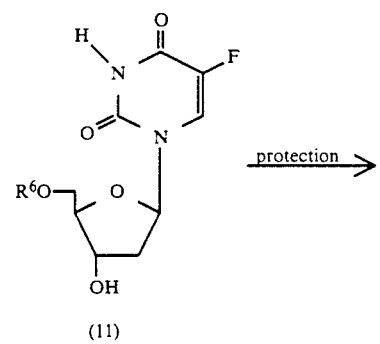

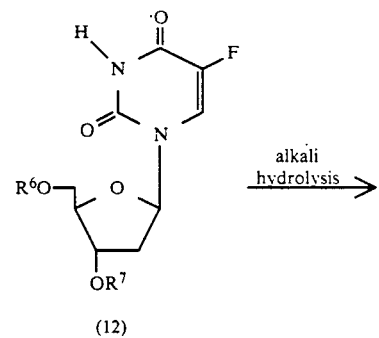

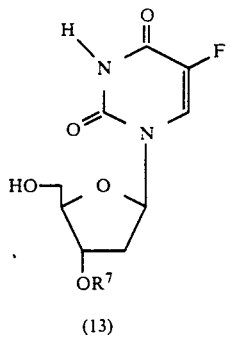

wherein $R^6$ is acyl, and $R^7$ is a protective group.

The acylation of the compound (10) is conducted in the same manner as the acylation of the compound (6) shown in the reaction scheme (c). More preferably, the acylation is conducted by reacting the compound (10) with an acid anhydride, corresponding to the acyl to be introduced into the 5′-position, in an amount of about 1 to about 1.5 moles per mole of the compound (10) at a temperature of about −30° C. to about 80° C. for about 1 to about 6 hours in the same inert solvent as used for the acid anhydride process shown by the scheme (c).

The above reaction gives as the main product a compound (11) wherein the 5'-position is acylated and also as a secondary product a compound wherein the 3'-position is acylated.

The compound (11) resulting from the reaction is then subjected to a reaction to protect the hydroxyl group at the 3'-position. By this reaction, the protective group mentioned with respect to the reaction scheme (a) is introduced into the 3'-position of the compound (11). Useful reagents for introducing the protective group are triaryl-substituted methyl halides for giving a protective group represented by the formula (A), unsaturated cyclic ethers which give a protecting group represented by the formula (B) and which are represented by the formula

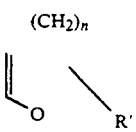

(B')

wherein R' and n are the same as those in the formula (B), lower alkoxymethyl halides, tri(lower alkyl)silyl halides, and benzyl halide for giving the protective group represented in the above item (E).

The protective group-introducing reaction wherein such a halide is used is conducted in the same manner as the dehydrohalogenation reaction shown in the reaction scheme (a). However, it is desirable that the reagent be used in an amount of 1 to 2 moles, preferably 1 to 1.5 moles, per mole of the compound (11), and that the reaction temperature be $-30°$ C. to $80°$ C.

The protective group-introducing reaction wherein an unsaturated cyclic ether of the formula (B') is used is conducted in the presence of an acid catalyst in an aprotic inert solvent such as THF, dioxane or acetonitrile. Examples of useful acid catalysts are hydrohalogenic acids such as hydrobromic acid and hydrochloric acid, and Lewis acids such as aluminum chloride, boron fluoride and zinc chloride. The reaction is conducted using 1 to 1.5 moles of the reagent per mole of the compound (11) at $-30°$ C. to $60°$ C. for about 2 to about 5 hours.

The reaction to remove the acyl group from the 5'-position of the resulting product (12) is conducted under the conditions of alkali hydrolysis, i.e. under the same conditions as the hydrolysis reaction for the reaction scheme (a) wherein a basic compound is used. Reaction scheme (f)

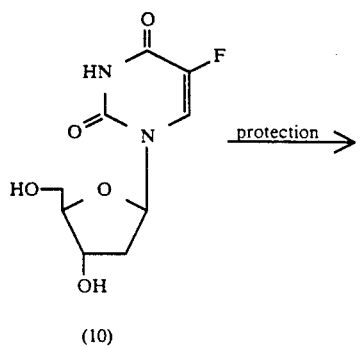

(10)

-continued

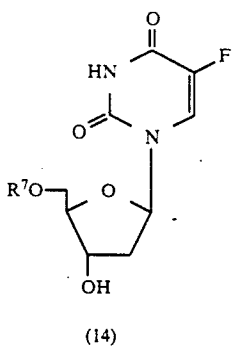

(14)

wherein $R^7$ is as defined above.

This reaction introduces a protective group directly into the compound (10), giving a compound (14) having the protective group at the 5'-position. The reaction is conducted under the same conditions as in the reactions scheme (e).

The processes of the schemes (e) and (f) afford starting compounds having an acyl group or protective group at either the 3'- or 5'-position.

Each of the compounds prepared according to the above reaction schemes can be used as the starting compound, as it is or after isolation from the reaction product by the usual method.

The compound of the invention can be also prepared according to reaction schemes (g) and (h) shown below.

Reaction scheme (g)

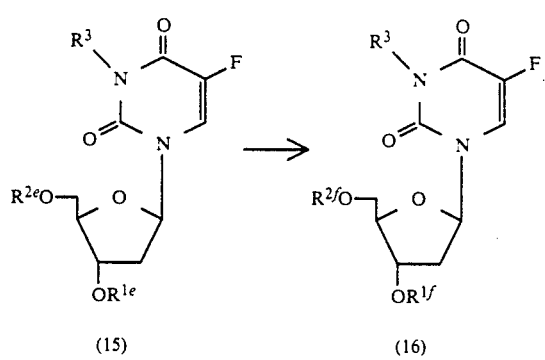

(15)          (16)

wherein $R^{1e}$ and $R^{2e}$ are each a hydrogen atom, acyl group or a group $-(A)_n-B_1$ (wherein A and n are as defined above, and $B_1$ is a 5- or 6- membered unsaturated heterocyclic group which have 1 to 4 hetero atoms selected from nitrogen, oxygen and sulfur atoms, which may have benzene, naphthalene or pyridine ring condensed therewith, and to which there are attached 1 to 3 hydroxy groups protected by the protective groups), $R^3$ is as defined above, and $R^{1f}$ and $R^{2f}$ are each a hydrogen atom, acyl group or a group $-(A)_n-B_2$ (wherein A and n are as defined above, and $B_2$ is a 5- or 6- membered unsatured heterocyclic group which have 1 to 4 hetero atoms selected from nitrogen, oxygen and sulfur atoms, which may have benzene, naphthalene or pyridine ring condensed therewith, and to which there are attached 1 to 3 hydroxy groups), with the proviso that when $R^{1e}$ or $R^{1f}$ is a hydrogen atom or acyl group, $R^{2e}$ or $R^{2f}$ is not a hydrogen atom nor acyl group.

The present reaction is conducted in the same manner as the reaction for removal of the protective group in the reaction scheme (a). Examples of hydroxy protecting groups on the heterocyclic ring are those as described in the reaction scheme (a).

Reaction scheme (h)

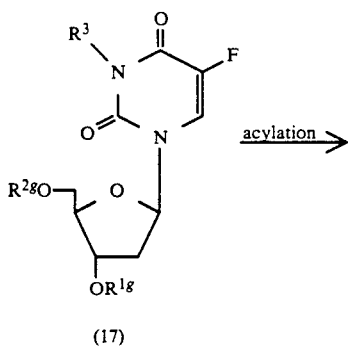

wherein $R^3$ is as defined above, $R^{1g}$ and $R^{2g}$ are each a hydrogen atom, acyl group or a group $—(A)_n\text{-}B_2$ (wherein n, A and $B_2$ are as defined above), and $R^{1h}$ and $R^{2h}$ are each a hydrogen atom, acyl or a group $—(A)_n\text{-}B_3$ (wherein n and A are as defined above, and $B_3$ is a 5- or 6- membered unsatured heterocyclic group which have 1 to 4 heteroatoms selected from nitrogen, oxygen and sulfur atoms, which may have benzene, naphthalene or pyridine ring condensed therewith, and to which 1 to 3 acyloxy groups are attached as substituents), with the proviso that when $R^{1g}$ or $R^{1h}$ is a hydrogen atom or acyl group, $R^{2g}$ or $R^{2h}$ is not a hydrogen atom nor acyl group.

The present reaction is the acylation of the hydroxyl group at the 3'- or 5'- position on the heterocyclic ring of the compound of the formula (17) in the presence of a condensation agent, and can be conducted int eh same manner as described in the reaction scheme (c). However, since the compound of the formula (17) has 1 to 3 hydroxy groups, the molar quantity of an acylating agent based on the compound of the formula (17) is about 1 to about 3 times that in the reaction scheme (c).

The 5-fluorouracil derivative of the formula (1β) can be prepared according to the following reaction scheme (i) or (j).

Reaction scheme (i)

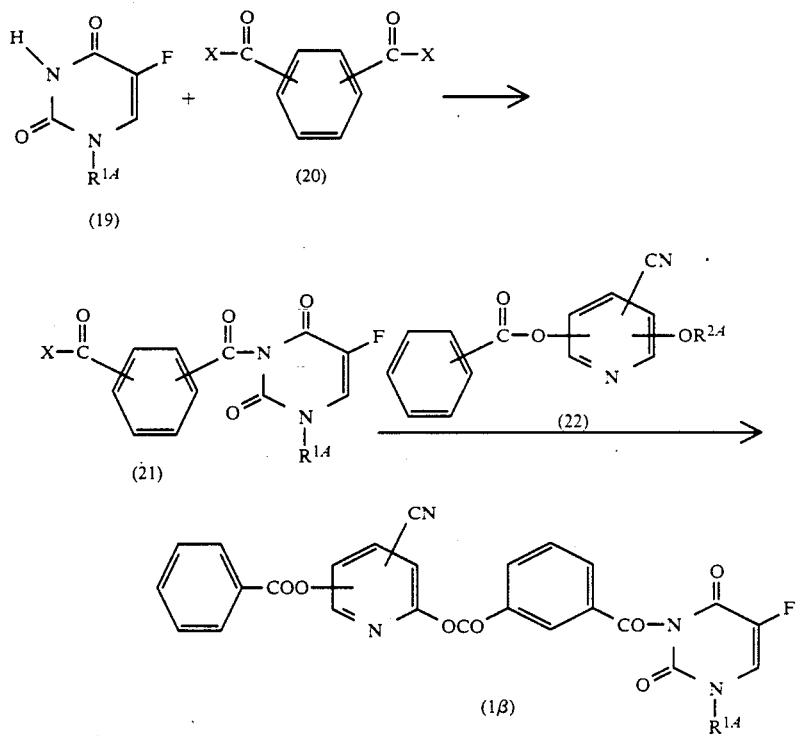

wherein $R^{1A}$ is as defined above, X is a halogen atom and $R^{2A}$ is a hydrogen atom or tri-(lower alkyl)silyl group.

According to the reactions scheme (i), the known compound (19) is allowed to react with the known compound (20) to obtain the intermediate (21).

This reaction is conducted in the presence of a suitable acid scavenger in a suitable solvent. Useful acid scavengers include those commonly used, e.g. inorganic basic compounds such as sodium hydrogen carbonate, sodium carbonate and potassium carbonate and organic basic compounds such as triethylamine, N,N-dimethylaminopyridine and pyridine. Useful solvents are those which will not adversely affect the reaction, e.g. ethers such as dioxane and tetrahydrofuran, nitriles such as acetonitriles, aromatic hydrocarbons such as benzene and toluene, halogenated hydrocarbons such as methylene chloride, chloroform and carbon tetrachloride, pyridine, and N,N-dimethylformamide.

While the ratio of the compound (20) to the compound (19) is not limited specifically, usually at least about 1 mole, preferably about 1 to about 3 moles, of the compound (20) is used per mole of the compound (19). The reaction temperature is usually about −30 to about 100° C., preferably room temperature to about 100° C. The reaction is completed in about 10 minutes to about 20 hours.

The intermediate (21) thus obtained is made to react with the known compound (22), giving the contemplated compound of the invention (1β).

This reaction can be conducted by the following process under conditions variable according to the kind of the compound (22). More specifically, when using the compound (22) wherein $R^{24}$ is a hydrogen atom, the reaction is conducted under the same conditions as described in the reaction between the compound (19) and the compound (20). When using the compound (22) wherein $R^{24}$ is tri-(lower alkyl)silyl, the reaction is conducted in a suitable solvent. Examples of useful solvents are aprotic solvents including ethers such as diethyl ether, dioxane and tetrahydrofuran, nitriles such as acetonitrile, aromatic hydrocarbons such as benzene and toluene, and halogenated hydrocarbons such as methylene chloride, chloroform and carbon tetrachloride. The solvent is used preferably in anhydrous form. The reaction temperature is usually about −30 to about 100° C., preferably room temperature to about 60° C. The reaction is completed in about 1 to about 20 hours. The reaction between the above intermediate (21) and the compound (22) wherein $R^{24}$ is tri-(lower alkyl)silyl group may employ a catalytic amount of a Lewis acid including aluminum chloride, stannic chloride, zinc chloride, etc. While the amount of the compound (22) is decided suitably and not limited specifically, usually at least about 1 mole, preferably, about 1 to about 3 moles, of the compound (22) is used per mole of the intermediate (21).

Reaction scheme (j)

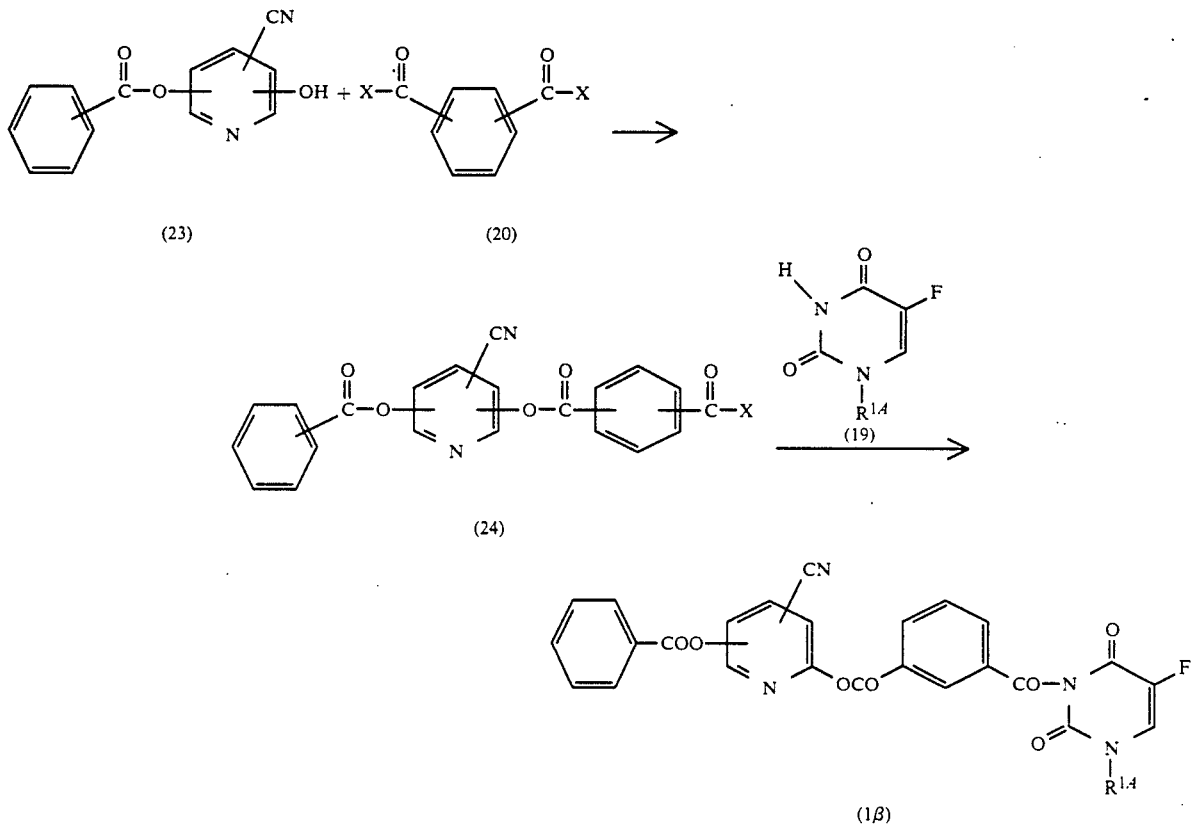

wherein $R^{14}$ and X are as defined above.

The reaction between the compound (20) and the compound (23) described in the reaction scheme (j) is conducted in the same manner as in the reaction scheme (i) for the reaction of the compound (20) and the compound (21).

The reaction between the intermediate (24) thus obtained and the compound (19) is also conducted in the same manner as in the reaction between the compound (20) and the compound (21).

Each compound having an acyloxy group on the pyridine ring, among the compounds (22) and (23) used in the above reaction schemes (i) and (j), is prepared by reacting a suitable acylating agent with a pyridine compound having a hydroxyl or tri-(lower alkyl)silyloxy group as the corresponding group. This acylation reaction is conducted in the same manner as in the reaction scheme (i) for the reaction of the compound (19) and the compound (20).

The contemplated compound obtained by each of the above processes and the compound (1β) of the invention can be purified and isolated from the reaction product by the usual separation method. The purification and isolation operations for these compounds are the same as those for the compound (1α) of the invention.

The compound of the invention represented by the above formula (1α) can be also prepared according to the following reaction schemes (k) and (l).

Reaction scheme (k)

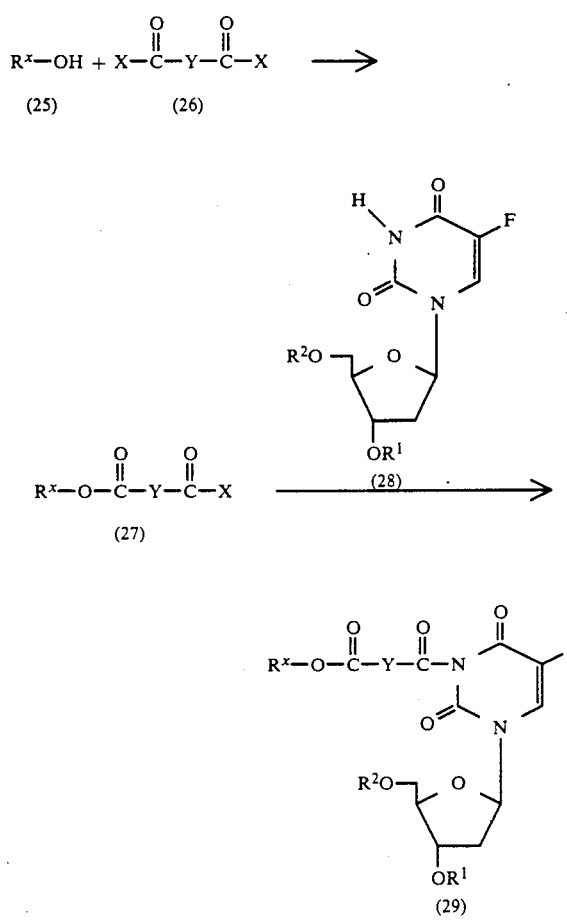

Reaction scheme (1)

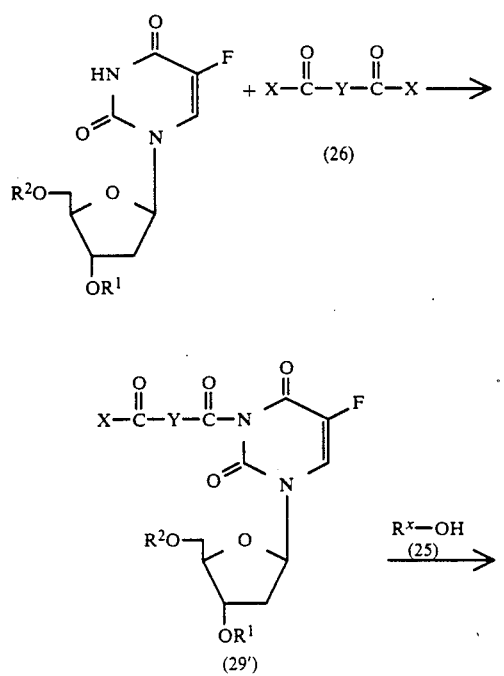

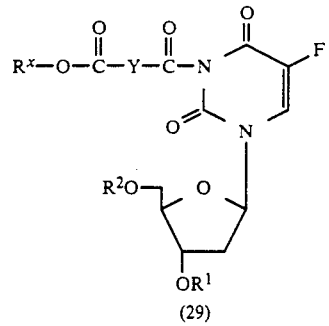

In the foregoing reaction schemes (k) and (l), $R^x$, $R^1$, $R^2$, X and Y are as defined above.

The reactions in the reaction schemes (k) and (l) are conducted in the same manner as in the reaction schemes (j) and (i), respectively. However, when $R^1$ or $R^2$ is a hydrogen atom, the reactions are conducted using the corresponding compound protected by the protective group exemplified above and then the protective group is removed.

The compound (25), which has at the 1-position of the pyridine ring a substituent selected from carbamoyl, lower alkylcarbamoyl and phenylcarbamoyl optionally substituted on the phenyl ring, is prepared by reacting the corresponding (1H)-pyridone derivative with isocyanate or isocyanate having a substituent in an amount of about 1 to about 2 moles of the latter per mole of the former in a suitable solvent, preferably in the presence of basic compound. The reaction conditions (useful basic compounds, kinds of solvents, reaction temperature, reaction time) accord to those for the reaction between the compound (19) and the compound (20) in reaction scheme (i).

Further the compound (25), which has a substituent selected from tetrahydrofuranyl, phthalidyl, lower alkoxy-lower alkyl optionally having phenyl, and lower alkyl at the 1-position of the pyridine ring, is prepared according to the following reaction. The reaction is conducted, for example, by reacting the corresponding compound having hydroxyl protected by tri(lower alkyl)silyl group as a starting compound with a compound of the formula $$R^{1i}-X \qquad (30)$$

wherein $R^{1i}$ is lower alkyl, phthalidyl or lower alkoxy-lower alkyl optionally having phenyl and X is as defined above, or a compound of the formula $$R^8-COO-R^{1j} \qquad (31)$$

wherein $R^8$ is lower alkyl, and $R^{1j}$ is a group selected from tetrahydrofuranyl, lower alkyl and lower alkoxy-lower alkyl optionally having phenyl. This reaction can be conducted in a suitable solvent and in the presence or in the absence of Lewis acid. Examples of preferable solvent are ethers such as diethyl ether, tetrahydrofuran and dioxane, aromatic hydrocarbons such as benzene and toluene, acetonitrile, acetone and ethyl acetate. Examples of preferred Lewis acids are boron trifluoride, tin tetrachloride and zinc chloride. The molar quantity of the compound (30) or the compound (31) is preferably about 1 to about 2 moles per mole of the starting compound. The reaction is generally conducted at a temperature in the range of room temperature to about 60° C., and is completed in about 1 to about 4 hours.

Among the compounds described in the above reaction schemes, the compound having tri(lower alkyl)silyloxy on the ring is prepared by reacting the corresponding compound having hydroxy as a starting compound with a silylating agent. Useful silylating agents can be any of those commonly used, e.g. tri(lower alkyl)disilazanes such as 1,1,1,3,3,3-hexamethyldisilazane, halogenated tri(lower alkyl)silanes such as trimethylchlorosilane and silylated acetamides such as N,O-bis(trimethylsilyl)acetamide. The molar quantity of the silylating agent is preferably about 1 to about 3 moles per mole of the starting compound. When the above halogenated trialkylsilane is used as the silylating agent, it is desirable to add to the reaction system about 1 to about 3 moles of amine or pyridine such as triethylamine, dimethylaniline and diethylaminopyridine per mole of the silylating agent. When the halogenated trialkylsilane or the silylated acetamide is used as the silylating agent, the reaction is preferably conducted in a suitable solvent, examples thereof being ethers such as diethyl ether, dioxane and tetrahydrofuran, nitriles such as acetonitrile, and halogenated hydrocarbons such as methylene chloride and chloroform. When tri(lower alkyl)disilazane is used as the silylating agent, another solvent is not needed since the silylating agent serves as a solvent. The silylation reaction is usually conducted at a temperature in the range of room temperature to nearly the boiling point of the solvent, and is completed in about 1 to about 15 hours.

The compound of the invention and the starting compound which have acyloxy are prepared by acylating the corresponding compound having hydroxy in the same manner as described above.

All of the compounds of the invention thus obtained have an outstanding anticancer effect and are low in toxicity. For example, such side effects as reduction in body weight are not observed in patients. The compounds of the invention are thus very useful as antitumor agents for curing cancers n man and animals. Particularly the compounds of the invention have excellent properties including (1) good absorption, (2) long-lasting effect, (3) high stability, (4) significantly low gastrointestinal toxicity, hence freedom from diarrhea, vomiting and gastrointestinal bleeding, and (5) great difference between the effective dose for producing the desired anticancer effect and the dose inducing side effects such as those due to toxicity, hence excellent in therapeutic index, safety, etc.

The desired products of the present invention are used in the form of generally acceptable pharmaceutical compositions which are prepared by using diluents or excipients such as fillers, bulking agents, binders, wetting agents, disintegrating agents, surfactants, lubricants and the like. Administration unit forms of these pharmaceutical compositions of the present invention can be varied and selected so as to meet various therapeutical purposes. Typical forms of the pharmaceutical compositions can be exemplified such as tablets, pills, powders, liquids, suspensions, emulsions, granules, capsules, suppositories, injections (liquids, suspensions and others), ointments and the like.

In shaping into the form of tablets, those known as the carriers in this field can widely be applied for example, excipients such as lactose, purified sugar, sodium chloride, glucose, urea, starch, calcium carbonate, kaolin, crystalline cellulose, silicic acid and others; binders such as water, ethanol, propanol, simple syrup, glucose solution, starch solution, gelatin solution, carboxymethyl cellulose, shellac, methyl cellulose, potassium phosphate, polyvinylpyrrolidone and others; disintegrating agents such as dried starch, sodium alginate, powdered agar, laminaran powder, sodium hydrogen carbonate, calcium carbonate, a fatty acid ester of polyoxyethylene sorbitan, sodium laurylsulfate, monoglyceride of stearic acid, starch, lactose and others; disintegration inhibitors such as purified sugar, stearin, cacao butter, hydrogenated oils and others; absorbefacients such as quaternary ammonium base, sodium laurylsulfate and others; wetting agents such as glycerin, starch and others; adsorbents such as starch, lactose, kaolin, bentonite, colloidal silicic acid and others; and lubricants such as purified talc, stearic acid salts, boric acid powder, polyethylene glycol and others can be exemplified. If necessary, the tablets can further be coated with usual coating, for example sugar-coated tablets, gelatin film-coated tablets, enteric coated tablets, film-coated tablets, or double-layered tablets, multiple-layered tablets and others. In shaping into the form of pills, those known as the carriers in this field can widely be applied for example, excipients such as glucose, lactose, starch, cacao butter, hardened vegetable oils, kaolin, talc and others; binders such as powdered gum arabic, powdered traganth, gelatin, ethanol and others; disintegrating agent such as laminaran, powder agar and others. In shaping into the form of suppositories, carriers known in this field can widely be applied for example, polyethylene glycol, cacao butter, a higher alcohol, an ester of a higher alcohol, gelatin, semi-synthesized glyceride and others. Capsules are prepared in a conventional manner by admixing the compound of the invention with the foregoing various carrier and encapsulating the mixture into hard-gelatin capsules, soft-gelatin capsules, etc. In case of preparing injections, solutions, emulsions and suspensions being prepared are sterilized, and they are preferably isotonic to the blood. In preparing into the form of solutions emulsions and suspensions, those known as the diluents in this field can widely be applied, for example water, ethanol, macrogol, propylene glycol, ethoxylated isostearyl alcohol, polyoxylated isostearyl alcohol, polyoxyethylene sorbitan fatty acid ester and others. In case of preparing isotonic solutions, sufficient amount of sodium chloride, glucose or glycerin may be added to make the solution to be isotonic to the blood. The pharmaceutical compositions for injection preparation may further contain usual solubilizers, buffer solutions, soothing agents or the like if necessary. In shaping into the form of pastes, creams and gels, diluents such as white vaseline, paraffins, glycerine, cellulose derivatives, polyethylene glycols, silicones, bentonite and the like can be used.

The pharmaceutical composition of the present invention may also contain coloring agents, preservatives, perfumes, seasoning agents, sweetening agents and others, as well as contain other medicines, if necessary.

The amount of the desired product according to the present invention to be contained as the active ingredient in the pharmaceutical composition is not specifically restricted and can be selected from a wide range, generally 1 to 70 % by weight, may be used.

Administration method of the above-mentioned pharmaceutical composition is not specifically restricted and the composition can be administered through a suitable method for the respective types of administration forms, depending upon age, sex, other conditions, and the symptoms of the patient and others. For example, tablets, pills, liquids, suspensions, emulsions, granules and capsules are administered orally; injections are administered intraveneously singly or as a mixture with usual injectable transfusions such as a glucose solution and an amino acids solutions; and if necessary the injections are administered singly intramuscularly, intracutaneously, subcutaneously or intraperitoneally; and the suppositories are administered into rectum.

The dosage of the desired products of the present invention may suitably be selected depending upon the method for administration, age, sex and other conditions, and conditions of the symptoms of the patients, and generally the pharmaceutical compositions of the invention can be administered in an amount of about 0.5 to about 20 mg/kg of the body weight/day, calculated as the compound of the invention (active ingredient), in 1 to 4 divided doses.

EXAMPLES

The present invention will be described below in more detail with reference to the following Examples.

EXAMPLE 1

Preparation of 2'-deoxy-5-fluoro-3'-O-(2-pyridyl)uridine

A 0.30 g quantity of sodium hydride (60%, dispersion in mineral oil) was added to a solution of 2.00 g of 2'-deoxy-5-fluoro-5'-O-trityluridine in 10 ml of dimethyl sulfoxide. The mixture was stirred at room temperature for 30 minutes. To the mixture was added 0.46 ml of 2-chloropyridine. Then the mixture was stirred at 80° C. for 3 hours. The solvent was distilled off and the residue was dissolved in 50 ml of ethyl acetate and 30 ml of water. The solution was made into a weak acidic solution by addition of 6N-hydrochloric acid. The ethyl acetate layer was separated, washed with water and concentrated. The residue was dissolved with heating in 20 ml of 80% acetic acid. The solution was left to stand at 80° C. for 1 hour and concentrated. The residue was dissolved in 50 ml of ethyl acetate, and the solution was washed with water, dried on anhydrous sodium sulfate and concentrated. The residue was purified by silica gel column chromatography using 1% methanol-chloroform as an eluent, giving 1.06 g of 2'-deoxy-5-fluoro-3'-O-(2-pyridyl)uridine in a yield of 80%.

M.p. 181–182° C.

NMR (DMSO-$d_6$) δ:
11.84 (1H, bs, NH),
8.29 (1H, d, J=7Hz, $C_6$-H),
8.22–8.14 (1H, m, $C_6$-H of pyridine ring),
7.85–7.65 (1H, m, $C_4$-H of pyridine ring),
7.09–6.84 (2H, m, $C_{3,5}$-H of pyridine ring),
6.26 (1H, t, J=7Hz, $C_{1'}$-H),
5.64–5.53 (1H, m, $C_{3'}$-H),
5.34 (1H, bs, $C_{5'}$-OH),
4.16–4.14 (1H, m, $C_{4'}$-H),
3.79 (2H, bs, $C_{5'}$-H),
2.47–2.34 (2H, m, $C_{2'}$-H)

EXAMPLES 2 TO 45

The general procedure of Example 1 was repeated, producing the compounds shown below in Table 1.

TABLE 1

| Example No. | $R^1$ | $R^2$ | $R^3$ | Yield (%) | m.p. (°C.) or form |
|---|---|---|---|---|---|
| 2 | 2-methyl-6-(benzyloxy)pyridine group | H | H | 78 | 169–171 |
| 3 | 4-pyridyl | H | H | 53 | 218–220 |
| 4 | 2-methyl-6-chloropyridine group | H | H | 52 | 205–207 |
| 5 | 2-quinolyl | H | H | 71 | 208–209 |
| 6 | 2-chloro-4-pyridyl | H | H | 16 | 227–229 |
| 7 | 2-methyl-6-methoxypyridine group | H | H | 39 | 218–220 |

TABLE 1-continued

| # | Structure | | | Yield | mp (°C) |
|---|---|---|---|---|---|
| 8 | 5-chloro-2-methylpyridine | H | H | 55 | 188–190 |
| 9 | 2,6-dimethylpyridine | H | H | 97 | powder |
| 10 | 5-nitro-2-methylpyridine | H | H | 62 | 174–176 |
| 11 | 5-cyano-6-benzyloxy-2-methylpyridine | H | H | 75 | powder |
| 12 | 3-cyano-2-ethoxy-6-methylpyridine | H | H | 26 | powder |
| 13 | 6-(4-methoxyphenoxy)-2-methylpyridine | H | H | 14 | 204–206 |
| 14 | 1-chloro-3-methylisoquinoline | H | H | 36 | 217–218 |
| 15 | 4-chloro-2-methylquinoline | H | H | 24 | 205–206 |
| 16 | 2-chloro-4-methylquinoline | H | H | 20 | 227–229 |
| 17 | 4-ethoxy-2-methylquinoline | H | H | 32 | 200–202 |
| 18 | 2-ethoxy-4-methylquinoline | H | H | 49 | 230–232 |

TABLE 1-continued
| | | | | | | |
|---|---|---|---|---|---|---|
| 19 | 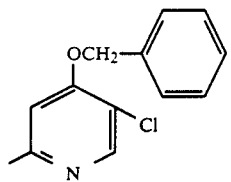 | H | H | 25 | 184–186 | |
| 20 | 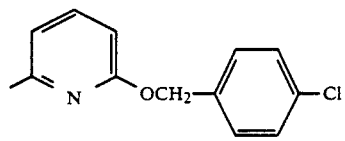 | H | H | 36 | 161–164 | |
| 21 | 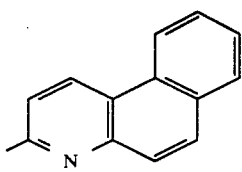 | H | H | 73 | 229–232 | |
| 22 | 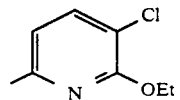 | H | H | 22 | powder | |
| 23 | 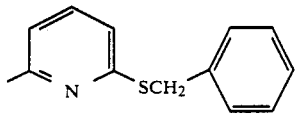 | H | H | 45 | 172–174 | |
| 24 | 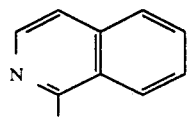 | H | H | 56 | powder | |
| 25 | 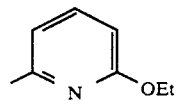 | H | H | 39 | 177–179 | |
| 26 | 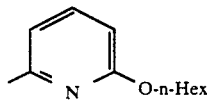 | H | H | 50 | 146–148 | |
| 27 | 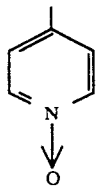 | H | H | 46 | 248–250 (decomp.) | |
| 28 | 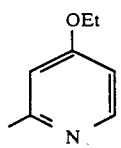 | H | H | 56 | 178–180 | |

TABLE 1-continued

| # | Structure | | | Yield | mp (°C) |
|---|---|---|---|---|---|
| 29 | 1,3-dimethyl-uracil-6-yl | H | H | 14 | 249–252 (decomp.) |
| 30 | benzothiazol-2-yl | H | H | 26 | 211–213 |
| 31 | pyrimidin-2-yl | H | H | 68 | 216–218 |
| 32 | pyrazin-2-yl | H | H | 62 | 222–223 |
| 33 | thiazol-2-yl | H | H | 33 | 163–165 |
| 34 | 6-methoxy-pyridazin-3-yl | H | H | 40 | powder |
| 35 | 6-chloro-pyridazin-3-yl | H | H | 17 | 235–236 |
| 36 | 2,4-dimethoxy-pyrimidin-6-yl | H | H | 36 | powder |
| 37 | 2,4-dimethoxy-1,3,5-triazin-6-yl | H | H | 58 | powder |
| 38 | quinoxalin-2-yl | H | H | 63 | 219–221 |
| 39 | 6-(methoxycarbonyl)-pyridin-2-yl | H | H | 10 | 217–220 |
| 40 | phthalazin-1-yl | H | H | 27 | 213–214 |

TABLE 1-continued

| | | | | | |
|---|---|---|---|---|---|
| 41 | (2-chloro-3-methylquinoxalin-2-yl structure) | H | H | 11 | powder |
| 42 | (3-methoxy-2-methylquinoxalinyl structure) | H | H | 82 | powder |
| 43 |  | H | H | 6 | powder |
| 44 | (2-methyl-1,8-naphthyridinyl structure) | H | H | 59 | 216–218 |
| 45 | (2-methyl-1,5-naphthyridinyl structure) | H | H | 36 | 242–244 |

| Example No. | NMR(DMSO-$d_6$): δ |
|---|---|
| 2 | 11.87(1H, bs, NH)8.27(1H, d, J=7Hz, $C_6$—H) 7.67(1H, t, J=8Hz, $C_4$—H of the pyridine ring), 7.40–7.32(5H, m, phenyl-H), 6.47 and 6.45(each 1H, d, J=8Hz, $C_3$ or $C_5$—H of the pyridine ring) 6.23(1H, t, J=6Hz, $C_{1'}$—H)5.53–5.40(1H, m, $C_{3'}$—H) 5.34(3H, s, —$\underline{CH_2}$—phenyl and $C_{5'}$—OH) 4.18–4.11(1H, m, $C_{4'}$—H), 3.78–3.74(2H, m, $C_{5'}$—H),2.43–2.31(2H, m, $C_{2'}$—H) |
| 3 | 11.80(1H, bs, NH)8.41(2H, d, J=6Hz, $C_2$—H and $C_6$—H of the pyridine ring)8.22(1H, d, J=7Hz, $C_6$—H) 7.03(2H, d, J=6Hz, $C_3$—H and $C_5$—H of the pyridine ring) 6.21(1H, t, =6Hz, $C_{1'}$—H) 5.49–5.13(2H, m, $C_{3'}$—H and $C_{5'}$—OH) 4.23–4.07(1H, m, $C_{4'}$—H)3.74–3.70(2H, m, $C_{5'}$—H) 2.54–2.37(m, $C_{2'}$—H, overlapped with DMSO) |
| 4 | 11.85(1H, bs, NH)8.26(1H, d, J=7Hz, $C_6$—H) 7.81(1H, t, J=8Hz, $C_4$—H of the pyridine ring), 7.13 and 6.92 (each 1H, d, J=8Hz, $C_3$—H or $C_5$—H of the pyridine ring), 6.24 (1H, t, J=7Hz, $C_{1'}$—H), 5.48–5.29(2H, m, $C_{3'}$—H and $C_{5'}$—OH) 4.15–4.13(1H, m, $C_{4'}$—H)3.77(2H, bs, $C_{5'}$—H) 2.55–2.34(m, $C_{2'}$—H, overlapped with DMSO) |
| 5 | 11.85(1H, bs, NH)8.31(1H, d, J=7Hz, $C_6$—H) 8.28(1H, d, J=9Hz, $C_4$—H of the quinoline ring), 7.95–7.36(4H, m, $C_{5,6,7,8}$—H of the quinoline ring), 7.08(1H, d, J=9Hz, $C_3$—H of the quinoline ring), 6.30(1H, t, J=7Hz, $C_{1'}$—H), 5.79–5.72(1H, m, $C_{3'}$—H), 5.39(1H, t, J=5Hz, $C_{5'}$—OH), 4.23–4.19(1H, m, $C_{4'}$—H), 3.95–3.80(2H, m, $C_{5'}$—H) 2.53–2.38(m, $C_{2'}$—H, overlapped with DMSO) |
| 6 | 11.85(1H, d, NH)8.24(1H, d, J=6Hz, $C_6$—H of the pyridine ring), 8.20(1H, d, J=6Hz, $C_6$—H), 7.19(1H, d, J=2Hz, $C_3$—H of the pyridine ring), 7.07(1H, dd, J=2Hz, J=6Hz, $C_5$—H of the pyridine ring), 6.21(1H, t, J=7Hz, $C_{1'}$—H) 5.38–5.15(2H, m, $C_{3'}$—H and $C_{5'}$—OH), 4.20–4.09(1H, m, $C_{4'}$—H), 3.71(2H, bs, $C_{5'}$—H) 2.55–2.38(m, $C_{2'}$—H, overlapped with DMSO) |
| 7 | 11.84(1H, d, NH)8.27(1H, d, J=7Hz, $C_6$—H) 7.65(1H, t, J=8Hz, $C_4$—H of the pyridine ring), 6.43 and 6.40(each 1H, d, J=8Hz, $C_3$ or $C_5$—H of the pyridine ring), 6.24(1H, t, J=7Hz, $C_{1'}$—H), 5.54–5.28(2H, m, $C_{3'}$—H and $C_{5'}$—OH), 4.16–4.11 (1H, m, $C_{4'}$—H), 3.84(3H, s, —$OCH_3$), 3.79–3.70(2H, m, $C_{5'}$—H), 2.55–2.35(m, $C_{2'}$—H, overlapped with DMSO) |
| 8 | 11.86(1H, d, NH)8.27(1H, d, J=7Hz, $C_6$—H) 8.21(1H, d, J=3Hz, $C_6$—H of the pyridine ring), 7.84(1H, dd, J=3Hz, J=9Hz, $C_4$—H of the pyridine ring)6.95(1H, d, J=9Hz, $C_3$—H of the pyridine ring), 6.23(1H, t, J=7Hz, $C_{1'}$—H), 5.56–5.48(1H, m, $C_{3'}$ |

TABLE 1-continued

|   |   |
|---|---|
|   | —H), 5.32(1H, t, J=5Hz, $C_{5'}$—OH), 4.14–4.12(1H, m, $C_{4'}$—H), 3.79-3.71(2H, m, $C_{5'}$—H), 2.55-2.33(m, $C_{2'}$—H, overlapped with DMSO) |
| 9 | 12.32(1H, bs, NH)8.26(1H, d, J=6Hz, $C_6$—H) 7.62(1H, t, J=8Hz, $C_4$—H of the pyridine ring), 6.86(1H, d, J=8Hz, $C_3$—H of the pyridine ring), 6.66(1H, d, J=8Hz, $C_5$—H of the pyridine ring) 6.32-6.15(1H, m, $C_{1'}$—H)5.56-5.46(1H, m, $C_{3'}$—H) 5.32(1H, bs, $C_{5'}$—OH), 4.16-4.08(1H, m, $C_{4'}$—H), 3.95–3.61(2H, m, $C_{5'}$—H), 2.43-2.33(5H, m, $C_{2'}$—H and —$CH_3$) |
| 10 | 11.85(1H, bs, NH)9.09(1H, d, J=3Hz, $C_6$—H of the pyridine ring), 8.52(1H, dd, J=3Hz, J=9Hz, $C_4$—H of the pyridine ring) 8.26(1H, d, J=7Hz, $C_6$—H)7.13(1H, d, J=9Hz, $C_3$—H of the pyridine ring), 6.25(1H, t, J=7Hz, $C_{1'}$—H), 5.73-5.64(1H, m, $C_{3'}$—H), 5.36(1H, t, J=5Hz, $C_{5'}$—OH), 4.23-4.15(1H, m, $C_{4'}$—H), 3.81-3.77(2H, m, $C_{5'}$—H), 2.57-2.39(m, $C_{2'}$—H, overlapped with DMSO) |
| 11 | 11.75(1H, bs, NH)8.29(1H, d, J=7Hz, $C_6$—H) 7.89(1H, d, J=8Hz, $C_4$—H of the pyridine ring), 7.54-7.25(5H, m, phenyl-H), 6.51(1H, d, J=8Hz, $C_5$—H of the pyridine ring), 6.36(1H, t, J=6Hz, $C_{1'}$—H), 5.68-5.64(1H, m, $C_{3'}$—H), 5.47(2H, s, —$CH_2$—) 5.30(1H, bs, $C_{5'}$—OH)4.29-4.24(1H, m, $C_{4'}$—H) 3.89-3.84(2H, m, $C_{5'}$—H)2.51-2.34(2H, m, $C_{2'}$—H) |
| 12 | 11.85(1H, bs, NH), 8.25(1H, d, 7=7Hz, $C_6$—H), 8.10(1H, d, J=8 Hz, $C_4$—H of the pyridine ring), 6.56)(1H, d, J=8Hz, $C_5$—H of the pyridine ring), 6.24-6.10(1H, m, $C_{1'}$—H)5.59-5.45(1H, m, $C_{3'}$—H) 5.32(1H, bs, $C_{5'}$—OH)4.42(2H, q, J=7Hz, —$CH_2CH_3$) 4.20-4.08(1H, m, $C_{4'}$—H)3.77-3.63(2H, m, $C_{5'}$—H) 2.50-2.30(2H, m, $C_{2'}$—H)1.34(3H, t, J=7Hz, —$CH_2\underline{CH_3}$) |
| 13 | 11.82(1H, bs, NH), 8.17(1H, d, J=7Hz, $C_6$—H), 7.74(1H, t, J=8 Hz, $C_4$—H of the pyridine ring), 7.08 and 6.92 (each 2H, d, J=9Hz, $C_{2,6}$—H or $C_{3,5}$—H of the benzene ring), 6.55-6.49(each 1H, d, J=8Hz, $C_3$—H or $C_5$—H of the pyridine ring)6.18(1H, t, J=6Hz, $C_{1'}$—H), 5.21-5.07(2H, m, $C_{3'}$—H and $C_{5'}$—OH), 4.02-3.99(1H, m, $C_{4'}$—H), 3.75(3H, s, $C_4$—$OCH_3$ of the benzene ring), 3.49-3.34(2H, m, $C_{5'}$—H) 2.28-2.14(2H, m, $C_{2'}$—H) |
| 14 | 11.87(1H, bs, NH)8.37-8.18 and 7.87-7.56(6H, m, H of the isoquinoline ring and $C_6$—H)6.37(1H, t, J=6Hz, $C_{1'}$—H) 5.74-5.69(1H, m, $C_{3'}$—H)5.44(1H, bs, $C_{5'}$—OH) 4.35-4.29(1H, m, $C_{4'}$—H)3.90-3.68(2H, m, $C_{5'}$—H)2.55-2.49(2H, m, $C_{2'}$—H) |
| 15 | 11.85(1H, d, NH)8.30(1H, d, J=7Hz, $C_6$—H) 8.15(1H, dd, J=1Hz, J=8Hz, $C_8$—H of the quinoline ring), 7.86-7.50 (3H, m, $C_{5,6,7}$—H of the quinoline ring), 7.40(1H, s, $C_3$—H of the quinoline ring), 6.29(1H, t, J=6Hz, $C_{1'}$—H), 5.77-5.69(1H, m, $C_{3'}$—H), 5.39(1H, t, J=5Hz, $C_{5'}$—OH), 4.24-4.23(1H, m, $C_{4'}$—H), 3.93-3.79(2H, m, $C_{5'}$—H), 2.55-2.38(m, $C_{2'}$—H, overlapped with DMSO) |
| 16 | 11.86(1H, bs, NH)8.29-8.14(2H, m, $C_8$—H of the quinoline ring and $C_6$—H), 7.89-7.53(3H, m, $C_{5,6,7}$—H of the quinoline ring), 7.21(1H, s, $C_3$—H of the quinoline ring), 6.31(1H, t, J=7Hz, $C_{1'}$—H), 5.49-5.31(2H, m, $C_{3'}$—H and $C_{5'}$—OH), 4.41-4.30 (1H, m, $C_{4'}$—H), 3.82-3.72(2H, m, $C_{5'}$H), 2.70-2.46 (m, $C_{2'}$—H, overlapped with DMSO) |
| 17 | 11.87(1H, d, NH), 8.30(1H, d, J=7Hz, $C_6$—H), 8.02(1H, d, J=8 Hz, $C_8$—H of the quinoline ring), 7.70-7.36(3H, m, $C_{5,6,7}$—H of the quinoline ring), 6.53(1H, s, $C_3$—H of the quinoline ring), 6.30(1H, t, J=7Hz, $C_{1'}$—H), 5.74-5.70(1H, m, $C_{3'}$—H), 5.37(1H, t, J=5Hz, $C_{5'}$—OH), 4.33-4.18(3H, m, $C_{4'}$—H and —$CH_2CH_3$), 3.90–3.82(2H, m, $C_{5'}$—H), 2.54-2.37(m, $C_{2'}$—H, overlapped with DMSO) 1.46(3H, t, J=7Hz, —$CH_2\underline{CH_3}$) |
| 18 | 11.86(1H, d, NH)8.43(1H, d, J=8Hz, $C_8$—H of the quinoline ring), 8.27(1H, d, J=7Hz, $C_6$—H), 7.71-7.31(3H, m, $C_{5,6,7}$—H of the quinoline ring) 6.56(1H, s, $C_3$—H of the quinoline ring) 6.30(1H, t, J=7Hz, $C_{1'}$—H) 5.42-5.31(2H, m, $C_{3'}$—H and $C_5'$—OH), 4.58-4.27(3H, m, $C_{4'}$—H and —$CH_2CH_3$) 3.82-3.73(2H, m, $C_5'$—H)2.68-2.51(2H, m, $C_{2'}$—H) 1.38(3H, t, J=7Hz, —$CH_2\underline{CH_3}$) |
| 19 | 11.85(1H, bs, NH) 8.28(1H, d, J=7Hz, $C_6$—H) 8.10(1H, s, $C_6$—H of the pyridine ring) 7.43 (5H, s, phenyl-H) 6.77(1H, s, $C_3$—H of the pyridine ring) 6.26(1H, t, J=7Hz, $C_{1'}$—H)  5.57-5.29(4H, m, $C_{3'}$—H, $C_{5'}$—OH and —$C\underline{H_2}$—⟨phenyl⟩) 4.14(1H, bs, $C_{4'}$—H)3.77(1H, bs, $C_{5'}$—H)2.44-2.37(2H, m, $C_{2'}$—H) |
| 20 | 11.85(1H, bs, NH) 8.27(1H, d, J=7Hz, $C_6$—H) 7.66(1H, t, J=8Hz, $C_4$—H of the pyridine ring), 7.43(4H, s, phenyl-H) 6.46 and 6.45 (each 1H, d, J=8Hz, $C_3$ or $C_5$—H of the pyridine ring) 6.23(1H, t, J=6Hz, $C_{1'}$—H) 5.48-5.33(4H, m, $C_{3'}$—H, $C_{5'}$— |

TABLE 1-continued

| | |
|---|---|
| | OH and —CH$_2$—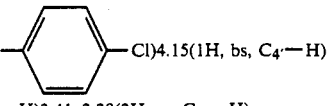—Cl)4.15(1H, bs, C$_{4'}$—H) |
| | 3.75(2H, bs, C$_{5'}$—H)2.41–2.29(2H, m, C$_{2'}$—H) |
| 21 | 11.64(1H, bs, NH), 9.22–7.19(9H, m, C$_{1,2,5,6,7,9,10}$—H of the benzo [f] quinoline ring and C$_6$—H)6.36–6.20(1H, m, C$_{1'}$—H) 5.80–5.68(1H, m, C$_{3'}$—H)4.29–4.19(1H, m, C$_{4'}$—H) 4.06–3.72(2H, m, C$_{5'}$—H)3.28(1H, bs, C$_{5'}$—OH)2.54–2.46(2H, m, C$_{2'}$—H) |
| 22 | 11.18(1H, bs, NH)8.27(1H, d, J=7Hz, C$_6$—H) 7.77 (1H, d, J=8Hz, C$_4$—H of the pyridine ring),6.47(1H, d, J=8Hz, C$_5$—H of the pyridine ring)6.25(1H, t, J=6Hz, C$_{1'}$—H) 5.59–5.43(1H, m, C$_{3'}$—H)4.50–4.18(3H, m, C$_{4'}$—H and —CH$_2$CH$_3$), 3.90–3.61(2H, m, C$_{5'}$—H), 3.29(1H, bs, C$_{5'}$—OH) 2.68–2.24(2H, m, C$_{2'}$—H)1.35(3H, t, J=7Hz, —CH$_2$CH$_3$) |
| 23 | 11.85(1H, d, NH)8.26(1H, d, J=7Hz, C$_6$—H) 7.60(1H, t, J=8Hz, C$_4$—H of the pyridine ring),7.41–7.23(5H, m, phenyl—H), 6.93 and 6.60 (each 1H, d,J=8Hz,C$_3$ or C$_5$—H of the pyridine ring) 6.22(1H, t, J=7Hz, C$_{1'}$—H)5.62–5.53(1H, m, C$_{3'}$—H) |
| | 5.35(1H, t, J=5Hz, C$_{5'}$—OH)4.41(2H, s, —CH$_2$—) |
| | 4.19–4.14(1H, m, C$_{4'}$—H)3.78–3.70(2H, m, C$_{5'}$—H)2.43–2.31(2H, m, C$_{2'}$—H) |
| 24 | 11.87(1H, bs, NH)8.45–7.40(7H, m, C$_{3,4,5,6,7,8}$—H of the isoquinoline ring and C$_6$—H), 6.42–6.27(1H, m, C$_{1'}$—H), 5.93–5.69(1H, m, C$_{3'}$—H), 5.41(1H, t, J=4Hz, C$_{5'}$—OH), 4.36–4.24(1H, m, C$_{4'}$—H)4.11–3.65(2H, m, C$_{5'}$—H) 2.60–2.44(2H, m, C$_{2'}$—H) |
| 25 | 11.85(1H, d, NH)8.26(1H, d, J=7Hz, C$_6$—H) 7.63(1H, t, J=8Hz, C$_4$—H of the pyridine ring) 6.41 and 6.39(each 1H, d, J=8Hz, C$_3$ or C$_5$—H of the pyridine ring) 6.24(1H, t, J=7Hz, C$_{1'}$—H)5.48–5.33(2H, m, C$_{3'}$—H and C$_{5'}$OH)4.40–4.16(3H, m, C$_{4'}$—H and —CH$_2$CH$_3$)3.76(2H, bs, C$_{5'}$—H) 2.49–2.35(2H, m, C$_{2'}$—H)1.32(3H, t, J=7Hz, —CH$_2$CH$_3$) |
| 26 | 11.85(1H, d, NH)8.28(1H, d, J=7Hz, C$_6$—H) 7.63(1H, t, J=8Hz, C$_4$—H of the pyridine ring), 6.41 and 6.37(each 1H, d, J=8Hz, C$_3$ or C$_5$—H of the pyridine ring), 6.24(1H, t, J=7Hz, C$_{1'}$—H) 5.46(2H, bs, C$_{3'}$—H and C$_{5'}$—OH)4.29–4.06(3H, m, C$_{4'}$—H and —OCH$_2$CH$_2$—)3.79–3.72(2H, m, C$_{5'}$—H)2.49–2.35(2H, m, C$_{2'}$—H) 1.76–1.20(8H, m, —OCH$_2$(CH$_2$)$_4$CH$_3$)0.87(3H, t, J=6Hz, —CH$_3$) |
| 27 | 11.90(1H, bs, NH), 8.20(1H, d, J=7Hz, C$_6$—H), 8.12(2H, d, J=8 Hz, C$_{2,6}$—H of the pyridine ring)7.09(2H, d, J=8Hz, C$_{3,5}$—H of the pyridine ring), 6.20(1H, t, J=7Hz, C$_{1'}$—H), 5.37(1H, t, J=5Hz, C$_{5'}$—OH), 5.15–5.03(1H, m, C$_{3'}$—H), 4.19–4.08(1H, m, C$_{4'}$—H), 3.74–3.71(2H, m, C$_{5'}$—H), 2.54–2.37(m, C$_{2'}$—H, overlapped with DMSO |
| 28 | 11.83(1H, bs, NH),8.28(1H, d, J=7Hz, C$_6$—H), 7.95(1H, d, J=6 Hz, C$_6$—H of the pyridine ring), 6.60(1H, dd, J=6Hz, 2Hz, C$_5$—H of the pyridine ring), 6.40(1H, d, J=2Hz,C$_3$—H of the pyridine ring) 6.23(1H, t, J=7Hz, C$_{1'}$—H)5.57–5.49(1H, m, C$_{3'}$—H) 5.30(1H, t, J=5Hz, C$_{5'}$—OH)4.22–3.98(3H, m, C$_{4'}$—H and —CH$_2$CH$_3$), 3.74(2H, bs, C$_{5'}$—H)2.42–2.30(2H, m, C$_{2'}$—H) 1.33(3H, t, J=7Hz, —CH$_3$) |
| 29 | 11.84(1H, d, NH)8.17(1H, d, J=7Hz, C$_6$—H) 6.21(1H, t, J=6Hz, C$_{1'}$—H)5.40–5.24(2H, m, C$_{5'}$—OH and C$_5$—H of the pyrimidine ring)5.14–5.02(1H, m, C$_{3'}$—H) 4.28–4.16(1H, m, C$_{4'}$—H)3.75–3.64(2H, m, C$_{5'}$—H) 3.25 and 3.13 (each 3H, s, N—CH$_3$ of the pyrimidine ring), 2.65–2.46 (m, C$_{2'}$—H, overlapped with DMSO) |
| 30 | 11.86(1H, d, NH)8.25(1H, d, J=7Hz, C$_6$—H) 7.96–7.64 and 7.51–7.19(4H, m, C$_{4,5,6,7}$—H of the benzothiazole ring), 6.33(1H, t, J=6Hz, C$_{1'}$—H), 5.74–5.68(1H, m, C$_{3'}$—H) 4.89–4.13(2H, m, C$_{4'}$—H and C$_{5'}$—OH) 3.95–3.65(2H, m, C$_{5'}$—H)2.78–2.30(m, C$_{2'}$—H, overlapped with DMSO) |
| 31 | 11.75 (1H, bs, NH)8.63(2H, d, J=5Hz, C$_{4,6}$—H of the pyrimidine ring)8.26(1H, d, J=7Hz, C$_6$—H) 7.18(1H, t, J=5Hz, C$_5$—H of the pyrimidine ring) 6.24(1H, t, J=6Hz, C$_{1'}$—H)5.59–5.51(1H, m, C$_{3'}$—H) 5.32(1H, bs, C$_{5'}$—OH)4.23–4.13(1H, m, C$_{4'}$—H) 3.84–3.74(2H, m, C$_{5'}$—H)2.60–2.30(2H, m, C$_{2'}$—H) |
| 32 | 11.82(1H, bs, NH)8.38–8.24(4H, m, C$_6$—H and C$_{3,5,6}$—H of the pyrazine ring)6.28–6.08(1H, m, C$_{1'}$—H) 5.54–5.43(1H, m, C$_{3'}$—H)5.28(1H, bs, C$_{5'}$—OH) 4.19–4.10(1H, m, C$_{4'}$—H)4.07–3.97(2H, m, C$_{5'}$—H) |

TABLE 1-continued

| | |
|---|---|
| | 2.51–2.33(2H, m, $C_{2'}$—H) |
| 33 | 11.85(1H, d, NH)8.23(1H, d, J=7Hz, $C_6$—H)<br>7.21 and 7.09(each 1H, d, J=4Hz, $C_4$ or $C_5$—H of the thiazole ring), 6.21<br>1H, t, J=6Hz, $C_{1'}$—H)5.51–5.29(2H, m, $C_{3'}$—H and<br>$C_{5'}$—OH)4.21–4.18(1H, m, $C_{4'}$—H)<br>3.77–3.70(2H, m, $C_{5'}$—H)2.49–2.37(2H, m, $C_{2'}$—H) |
| 34 | 11.84(1H, d, NH)8.26(1H, d, J=7Hz, $C_6$—H)<br>7.24(2H, s, $C_{4,5}$—H of the pyridazine ring), 6.29–6.12(1H, m,<br>$C_{1'}$—H), 5.60–5.51 (1H, m, $C_{3'}$—H), 5.32(1H, t, J=4Hz,<br>$C_{5'}$—OH), 4.21–4.13(1H, m, $C_{4'}$—H), 3.95(3H, s, —$CH_3$)<br>3.82–3.67(2H, m, $C_{5'}$—H)2.54–2.35(2H, m, $C_{2'}$—H) |
| 35 | 11.87(1H, d, NH)8.26(1H, d, J=7Hz, $C_6$—H)<br>7.84 and 7.42(each 1H, d, J=9Hz,$C_4$ or $C_5$—H of the pyridazine ring)<br>6.26(1H, t, J=7Hz, $C_{1'}$—H)5.73–5.64(1H, m, $C_{3'}$—H)<br>5.35(1H, t, J=5Hz, $C_{5'}$—OH)4.23–4.17(1H, m, $C_{4'}$—H)<br>3.80–3.76(2H, m, $C_{5'}$—H)2.54–2.39(m, $C_{2'}$—H, overlapped with DMSO) |
| 36 | 11.83(1H, bs, NH)8.25(1H, d, J=7Hz, $C_6$—H)<br>6.23(1H, t, J=6Hz, $C_{1'}$—H)5.93(1H, s, $C_5$—H of the pyrimidine<br>ring), 5.53–5.52(1H, m, $C_{3'}$—H)5.34(1H, t, J=5Hz, $C_{5'}$—OH)<br>4.15–4.14(1H, m, $C_{4'}$—H)3.89 and 3.87 (each 3H, s, $C_2$ or $C_4$<br>—$OCH_3$ of the pyrimidine ring)3.80–3.74(2H, m, $C_{5'}$—H)<br>2.54–2.36(m, $C_{2'}$—H, overlapped with DMSO) |
| 37 | 11.84(1H, d, NH)8.24(1H, d, J=7Hz, $C_6$—H)<br>6.29–6.14(1H, m, $C_{1'}$—H)5.59–5.46(1H, m, $C_{3'}$—H)<br>5.33(1H, bs, $C_{5'}$—OH)4.24–4.16(1H, m, $C_{4'}$—H)<br>3.94(6H, s, —$CH_3 \times 2$)3.80–3.65(2H, m, $C_{5'}$—H)2.57–2.25(2H, m, $C_{2'}$—H) |
| 38 | 11.86(1H, bs, NH)8.65(1H, s, $C_3$—H of the quinoxaline<br>ring), 8.35–7.53(5H, m, $C_6$—H and $C_{5,6,7,8}$—H of the quinoxaline ring)<br>6.40–6.24(1H, m, $C_{1'}$—H)5.77–5.64(1H, m, $C_{3'}$—H)<br>5.40(1H, bs, $C_{5'}$—OH)4.33–4.24(1H, m, $C_{4'}$—H)<br>4.03–3.69(2H, m, $C_{5'}$—H)2.57–2.44(2H, m, $C_{2'}$—H) |
| 39 | 11.84(1H, bs, NH)8.29(1H, d, J=7Hz, $C_6$—H)<br>7.94(1H, t, J=7Hz, $C_4$—H of the pyridine ring), 7.71(1H, dd, J=1Hz,<br>J=7Hz, $C_5$—H of the pyridine ring)7.17(1H, dd, J=1Hz, J=7Hz, $C_3$—<br>H of the pyridine ring)6.25(1H, t, J=6Hz, $C_{1'}$—H)<br>5.56–5.49(1H, m, $C_{3'}$—H)5.31(1H, t, J=5Hz, $C_{5'}$—OH)<br>4.19–4.11(1H, m, $C_{4'}$—H)3.99–3.80(5H, m, $C_{5'}$—H and<br>—$COOCH_3$), 2.55–2.33(m, $C_{2'}$—H, overlapped with DMSO) |
| 40 | 11.86(1H, d, NH)9.38(1H, s, $C_4$—H of the phthalazine<br>ring), 8.38–7.96(5H, m, $C_6$—H and $C_{5,6,7,8}$—H of the<br>phthalazine ring), 6.38(1H, t, J=7Hz, $C_{1'}$—H), 5.93–5.85(1H, m,<br>$C_{3'}$—H), 4.41–4.33(1H, m,$C_{4'}$—H), 3.42–3.39(2H, m,<br>$C_{5'}$—H), 2.64–2.47(m, $C_{2'}$—H, overlapped with DMSO) |
| 41 | 11.86(1H, bs, NH)8.31(1H, d, J=7Hz, $C_6$—H)<br>8.00–7.26(4H, m, $C_{5,6,7,8}$—H of the quinoxaline ring)<br>6.37–6.23(1H, m, $C_{1'}$—H)5.72(1H, bs, $C_{3'}$—H)<br>5.43(1H, bs, $C_{5'}$—OH)4.49–4.28(1H, m, $C_{4'}$—H)<br>4.07–3.60(2H, m, $C_{5'}$—H)2.60–2.41(m, $C_{2'}$—H, overlapped with DMSO) |
| 42 | 11.86(1H, bs, NH)8.30(1H, d, J=7Hz, $C_6$—H)<br>7.81–7.48(4H, m, $C_{5,6,7,8}$—H of the quinoxaline ring)<br>6.34–6.19(1H, m, $C_{1'}$—H)5.76–5.72(1H, m, $C_{3'}$—H)<br>5.41(1H, bs, $C_{5'}$—OH)4.33–4.23(1H, m, $C_{4'}$—H)<br>4.09(3H, s, —$CH_3$)3.94–3.88(2H, m, $C_{5'}$—H)<br>2.62–2.41(m, $C_{2'}$—H, overlapped with DMSO) |
| 43 | solvent: $CDCl_3$ 9.80(1H, bs, NH)<br>8.01(1H, dd, J=1Hz, J=6Hz, $C_6$—H), 7.50–7.18(10H, m,<br>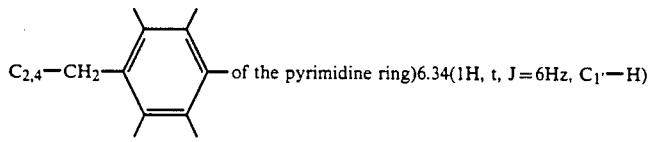of the pyrimidine ring)6.34(1H, t, J=6Hz, $C_{1'}$—H)<br>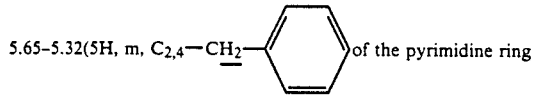of the pyrimidine ring<br>and $C_{3'}$—H)4.28–4.23(1H, m, $C_{4'}$—H)<br>3.92(2H, bs, $C_{5'}$—H)2.57–2.35(2H, m, $C_{2'}$—H) |
| 44 | 11.86(1H, d, NH), 8.83(1H, dd, J=3Hz, J=4Hz, $C_6$—H of the<br>1,5-naphthyridine ring), 8.37–8.12 (3H, m, $C_{4,8}$—H of the 1,5-naphthyridine<br>ring and $C_6$—H)7.70(1H, dd, J=4Hz, J=9Hz, $C_7$—H of the 1,5-naphthyridine<br>ring), 7.34(1H, d, J=9Hz, $C_3$—H of the 1,5-naphthyridine ring), 6.30(1H,<br>t, J=6Hz, $C_{1'}$—H), 5.79–5.69(1H, m, $C_{3'}$—H), 5.40(1H, bs,<br>$C_{5'}$—OH), 4.29–4.20(1H, m, $C_{4'}$—H), 3.94–3.71(2H, m,<br>$C_{5'}$—H), 2.66–2.36(m, $C_{2'}$—H, overlapped with DMSO) |
| 45 | 11.87(1H, d, NH), 8.95–8.92(1H, m, $C_7$—H of the naphthyridine ring)<br>8.43–8.29(3H, m, $C_{4,5}$—H of the naphthyridine ring and $C_6$—H), 7.51<br>(1H, dd, J=8Hz, J=4Hz, $C_6$—H of the naphthyridine ring), 7.21(1H, d, J=<br>9Hz, $C_3$—H of the naphthyridine ring) 6.31(1H, t, J=7Hz, $C_{1'}$—H)<br>5.81(1H, bs, $C_{3'}$—H), 5.42(1H, bs, $C_{5'}$—OH), 4.26(1H, bs, $C_{4'}$—H) |

TABLE 1-continued 4.10–3.85(2H, m, $C_{5'}$—H), 2.67–2.33(m, $C_{2'}$—H, overlapped with DMSO)

EXAMPLES 46 TO 48

Preparation of 2'-deoxy-3',5'-di-O-(2-pyridyl)-5-fluorouridine, 2'-deoxy-5-fluoro-3'-O-(2-pyridyl)uridine and 2'-deoxy-5-fluoro-5'-O-(2-pyridyl)uridine.

A 0.70 g quantity of sodium hydride (60%, dispersion in mineral oil) was added to a solution of 2.00 g of 2'-deoxy-5-fluorouridine in 10 ml of dimethyl sulfoxide. The mixture was stirred at room temperature for 30 minutes. To the mixture was added 0.91 ml of 2-chloropyridine. Then the mixture was stirred at 80° C. for 3 hours. The solvent was distilled off and the residue was dissolved in 50 ml of ethyl acetate and 30 ml of water. The solution was made into a weak acidic solution by addition of 6N-hydrochloric acid. The ethyl acetate layer was separated, washed with water, dried over anhydrous magnesium sulfate and concentrated.

The residue was purified by silica gel column chromatography using 1–2% methanol-chloroform as an eluent, giving 2'-deoxy3',5'-0-di-(2-pyridyl)-5-fluorouridine (Example 46), 2'-deoxy-5-fluoro-3'-O-(2-pyridyl)uridine (Example 47) and 2'-deoxy-5-fluoro-5'-O-(2-pyridyl)uridine (Example 48).

Compound obtained in Example 46
Yield: 0.62 g (19%)
M.p. 152–155° C.
NMR (DMSO-$d_6$) δ:
11.90 (1H, bs, NH),
8.20–8.14 (2H, m, $C_6$-H of pyridine ring),
8.02 (1H, d, J=7Hz, $C_6$-H),
7.86–7.66 (2H, m, $C_4$-H of pyridine ring),
7.09–6.87 (4H, m, $C_{3,5}$-H of pyridine ring),
6.30 (1H, t, J=7Hz, $C_{1'}$-H),
5.66–5.61 (1H, m, $C_{3'}$-H),
4.67–4.63 (2H, m, $C_{5'}$-H),
4.57–4.43 (1H, m, $C_{4'}$-H),
2.57–2.47 (2H, m, $C_{2'}$-H)

Compound obtained in Example 47
Yield: 0.20 g (7.6%)
The Rf value in silica gel thin-layer chromatography using chloroform-methanol (=39:2) as an eluent, melting point and analysis result of NMR spectrum revealed that the compound prepared was identical with the compound obtained in Example 1.

Compound obtained in Example 48
Yield: 0.60 g (23%)
M.p.: 177–179° C.
NMR (DMSO-$d_6$) δ:
11.70 (1H, bs, NH),
8.19 (1H, dd, J=1Hz, J=5Hz, $C_6$-H of pyridine ring),
7.98 (1H, d, J=7Hz, $C_6$-H),
7.85–7.65 (1H, m, $C_4$-H of pyridine ring),
7.09–6.82 (2H, m, $C_{3,5}$-H of pyridine ring),
6.22 (1H, t, J=7Hz, $C_{1'}$-H),
4.53–4.31 (3H, m, $C_{3',5'}$-H),
4.21–4.09 (1H, m, $C_{4'}$-H),
2.36–2.21 (2H, m, $C_{2'}$-H)

EXAMPLES 49 AND 50

The compounds as listed below in Table 2 were prepared in the same manner as in Examples 46 to 48.

TABLE 2

| Example No. | $R^1$ | $R^2$ | $R^3$ | Yield (%) | m.p. (°C.) or form | NMR: δ |
|---|---|---|---|---|---|---|
| 49 | 6-t-Bu-2-pyridyl-O– | 6-t-Bu-2-pyridyl-O– | H | 7 | powder | solvent: CDCl$_3$ 10.15(1H, bs, NH)7.99(1H, d, J=6Hz, $C_6$—H) 7.49 and 7.46(each 1H, t, J=8Hz, $C_4$—H of the pyridine ring)6.47(1H, t, J=7Hz, $C_{1'}$—H) 6.39–6.25(4H, m, $C_{3,5}$—H of the pyridine ring × 2) 5.73–5.61(1H, m, $C_{3'}$—H)4.63–4.57(3H, m, $C_{4',5'}$—H)2.67–2.28(2H, m, $C_{2'}$—H)1.57 and 1.48 (each 9H, s, CH$_3$ × 3) |
| 50 | H | 6-t-Bu-2-pyridyl-O– | H | 15 | 78–81 | solvent: DMSO-$d_6$ 11.83(1H, d, NH)7.93(1H, d, J=7Hz, $C_6$—H) 7.59(1H, t, J=8Hz, $C_4$—H of the pyridine ring), 6.37 and 6.29 (each 1H, d, J=8Hz, $C_3$ or $C_5$—H of the pyridine ring), 6.20(1H, t, J=7Hz, $C_{1'}$—H), 5.43(1H, d, J=4Hz, $C_{3'}$—OH), 4.44–4.27(3H, m, $C_{3',5'}$—H), 4.17–4.06(1H, m, $C_{4'}$—H), 2.34–2.20 (2H, m, $C_{2'}$—H), 1.55(9H, s, CH$_3$×3) |

(t-Bu is tert-butyl group.)

EXAMPLE 51

Preparation of 5'-O-acetyl-3'-O-(6-benzyloxy-2-pyridyl)-2'-deoxy-5-fluorouridine A 1.00 ml quantity of acetic anhydride was added to a solution of 1.50 g of 3'-0-(6-benzyloxy-2-pyridyl)-2'-deoxy-5-fluorouridine in 10 ml of pyridine. The mixture was stirred at room temperature for 1.5 hours. Water (1 ml) was added thereto and the mixture was stirred at room temperature for 30 minutes. The solvent was distilled off, and 10 ml of ethanol was added to the residue. The insolubles were filtered and dried, giving 1.07 g (65%) of 5'-O-acetyl-3'-O-(6-benzyloxy-2-pyridyl)-2'-deoxy-5-fluorouridine.

M p. 185–186° C.
NMR (DMSO-$d_6$) δ:
11.91 (1H, s, NH),
7.99 (1H, d, J=7Hz, $C_6$-H),
7.68 (1H, t, J=8Hz, $C_4$-H of pyridine ring),
7.39–7.29 (5H, m, phenyl-H),
6.50 and 6.46 (each 1H, d, J=8Hz, $C_{3,5}$-H of pyridine ring),
6.22 (1H, t, J=7Hz, $C_{1'}$-H),
5.49–5.35 (3H, m, $C_{3'}$-H and —CH$_2$—),
4.43–4.23 (3H, m, $C_{4',5''}$-H), 2.55–2.40 (2H, m, $C_{2'}$-H), 2.05 (3H, s, COCH$_3$)

EXAMPLES 52 TO 59

The compounds shown below in Table 3 were prepared in the same manner as in Example 51.

TABLE 3

| Example No. | R$^1$ | R$^2$ | R$^3$ | Yield (%) | m.p. (°C.) or form | NMR (DMSO-d$_6$): δ |
|---|---|---|---|---|---|---|
| 52 | 6-methylpyridin-2-yl-OAc | Ac | H | 88 | 177~180 | 11.89(1H, bs, NH) 7.99(1H, d, J=7Hz, C$_6$—H) 7.89(1H, t, J=8Hz, C$_4$—H of the pyridine ring), 6.84 and 6.82(each 1H, d, J=8Hz, C$_3$ or C$_5$—H of the pyridine ring), 6.23(1H, t, J=6Hz, C$_{1'}$—H), 5.44-5.32(1H, m, C$_{3'}$—H), 4.38-4.24(3H, m, C$_{4'}$, C$_{5'}$—H), 2.58-2.44(2H, m, C$_{2'}$—H), 2.29 (3H, s, —OCOCH$_3$ of the pyridine ring) 2.07(3H, s, C$_{5'}$—OCOCH$_3$) |
| 53 | 6-methylpyridin-2-yl-OCOEt | COEt | H | 98 | 161~162 | 11.89(1H, bs, NH)7.97(1H, d, J=7Hz, C$_6$—H) 7.89(1H, t, J=8Hz, C$_4$—H of the pyridine ring), 6.85 and 6.81(each 1H, d, J=8Hz, C$_3$ or C$_5$—H of the pyridine ring), 6.24(1H, t, J=6Hz, C$_{1'}$—H), 5.40-5.36(1H, m, C$_{3'}$—H), 4.40-4.25(3H, m, C$_{4',5'}$—H), 2.74-2.25(6H, m, C$_{2'}$—H and —COCH$_2$CH$_3$×2)1.15 and 1.05(each 3H, t, J=7Hz, —COCH$_2$CH$_3$) |
| 54 | —CH$_2$-furyl | COEt | H | 68 | 79~81 | 11.86(1H, bs. NH)7.90(1H, d, J=7Hz, C$_6$—H) 7.64(1H, t, C$_5$—H of the furan ring)6.44(2H, d, C$_{3,4}$—H of the furan ring), 6.08(1H, t, J=7Hz, C$_{1'}$—H), 4.50(2H, s, —OCH$_2$—)4.22-4.07(4H, m, C$_{3',4',5'}$—H), 2.48-2.20(4H, m, C$_{2'}$—H and —COCH$_2$CH$_3$)1.04(3H, t, J=7Hz, —CH$_2$CH$_3$) |
| 55 | 5-cyano-6-methylpyridin-2-yl-OH | COEt | H | 61 | powder | 11.96(1H, bs, OH) 11.91(1H, d, NH) 8.06-7.91 (2H, m, C$_6$—H and C$_4$—H of the pyridine ring) 6.40 (1H, d, J=8Hz, C$_5$—H of the pyridine ring) 6.30-6.13(1H, m, C$_{1'}$—H) 5.51-5.46(1H, m, C$_{3'}$—H) 4.48-4.30(3H, m, C$_{4',5'}$—H) 2.65-2.27(m, C$_{2'}$—H. —CH$_2$—, overlapped with DMSO) 1.04(3H, t, J=7Hz,—CH$_3$) |
| 56 | —CH$_2$-thienyl | Ac | H | 95 | 81~82 | 11.85(1H, bs, NH)7.92(1H, d, J=7Hz, C$_6$—H) 7.52(1H, dd, J=5Hz, J=1Hz, C$_5$—H of the thiophene ring), 7.12-6.96(2H, m, C$_{3,4}$—H of the thiophene ring)6.11(1H, td, J=7Hz, J=2Hz, C$_{1'}$—H)4.72(2H, s, —CH$_2$—)4.20-4.04(4H, m, C$_{3',4',5'}$—H)2.36-2.23(2H, m, C$_{2'}$—H) 2.04(3H, s, —COCH$_3$) |
| 57 | —CH$_2$-thienyl | COEt | H | 86 | 100~101 | 11.85(1H, bs, NH) 7.90(1H, d, J=7Hz, C$_6$—H) 7.52(1H, dd, J=5Hz, J=1Hz, C$_{5'}$—H of the thiophene ring) 7.12-6.96(2H, m, C$_{3,4}$—H of the thiophene ring) 6.10(1H. td, J=7Hz, J=2Hz, C$_{1'}$—H) 4.72 (2H, s,—CH$_2$—) 4.19-4.06(4H, m, C$_{3',4',5'}$—H), 2.38-2.22(4H, m, C$_{2'}$—H and —COCH$_2$—) 1.03(3H, t, J=8Hz,—CH$_3$) |
| 58 | —CH$_2$-thienyl | CO-n-Pen | H | 75 | 76~77 | 11.86(1H, bs, NH)7.90(1H, d, J=7Hz, C$_6$—H) 7.51(1H, dd, J=5Hz, J=1Hz, C$_5$—H of the thiophene ring), 7.21-6.95(2H, m, C$_{3,4}$—H of the thiophene ring)6.11(1H, td, J=7Hz, J=2Hz, C$_{1'}$—H), 4.72(2H, s, —CH$_2$—)4.19-4.05(4H, m, C$_{3',4',5'}$—H), 2.38-2.24(4H, m, C$_{2'}$—H and —COCH$_2$—), 1.60-1.15(6H, m, —COCH$_2$(CH$_2$)$_3$CH$_3$)0.85(3H, t, J=6Hz, CH$_3$) |
| 59 | —CH$_2$-(5-chlorothienyl) | COEt | H | 77 | 124~125 | solvent: CDCl$_3$ 7.64(1H, d, J=6Hz, C$_6$—H)6.78(2H, s, C$_{3,4}$—H of the thiophene ring), 6.29-6.12(1H, m, C$_{1'}$—H) 4.61 and 4.59(each 1H, s, C$_{3'}$—O—CH$_2$), 4.42-4.09 (4H, m, C$_{3',4',5'}$—H)2.68-1.89(4H, m, C$_{2'}$—H and —CH$_2$CH$_3$)1.17(3H, t, J=7Hz, —CH$_3$) |

EXAMPLE 60

Preparation of
2'-deoxy-5-fluoro-3'-O-(6-hydroxy-2-pyridyl)uridine

In 80 ml of methanol was dissolved 2.10 g of 3'-O-(6-benzyloxy-2-pyridyl)-2'-deoxy-5-fluorouridine. The solution was subjected to catalytic reduction in the presence of 200 mg of 5% palladium charcoal at room temperature for 3 hours. The catalyst was filtered and the filtrate was concentrated. The residue was treated with ethyl acetate. The insolubles were filtered and dried, giving 1.02 g of 2'-deoxy-5-fluoro-3'-O-(6-hydroxy-2-pyridyl)uridine in a yield of 61%.

M.p.: 218-220° C.
NMR (DMSO-d$_6$) δ:
11.84 (1H, d, NH),
10.57 (1H, s, C$_6$-OH of pyridine ring),
8.30 (1H, d, J=7Hz, C$_6$-H),
7.55 (1H, t, J=8Hz, C$_4$-H of pyridine ring),
6.33-6.19 (3H, m, C$_{3,5}$-H of pyridine ring, C$_1'$-H),
5.44-5.31 (2H, m, C$_3'$-H and —C$_5'$—OH),
4.15-4.08 (1H, m, C$_4'$-H),
3.85-3.77 (2H, m, C$_5'$-H),
2.44-2.32 (2H, m, C$_2'$-H)

EXAMPLES 61 TO 63

The compounds shown below in Table 4 were prepared by following the general procedure of Example 60.

solution of 1.00 g of 2'-deoxy-5-fluoro-5'-O-trityluridine in 30 ml of dioxane. The mixture was stirred at 80° C. for 2 hours. The solvent was distilled off and the residue was dissolved in 30 ml of ethyl acetate. The solution was washed with water and dried. The residue was dissolved in 15 ml of 80% acetic acid and the solution was left to stand at 80° C. for 2 hours. The solvent was distilled off and the residue was dissolved in ml of ethyl acetate. The solution was washed with water and dried. The residue was treated with chloroform, the insolubles were filtered and recrystallized from ethanol, giving 0.37 g of 2'-deoxy-5-fluoro-3'-O-(2-furanylmethyl)uridine in a yield of 55%.

M.p.: 186-188° C.
NMR (DMSO-d$_6$) δ:
11.82 (1H, bs, NH),
8.19 (1H, d, J=6Hz, C$_6$-H),
7.65-7.63 (1H, m, C$_5$-H of furan ring),
6.45 and 6.44 (2H, C$_{3,5}$-H of furan ring),
6.09 (1H, t, J=7Hz, C$_1'$-H),
5.22 (1H, bs, C$_5'$-H),
4.49 (2H, s,

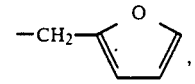

4.21-4.12 (1H, m, C$_3'$-H),
4.01-3.92 (1H, m, C$_4'$-H),
3.64-3.55 (2H, m, C$_5'$-H),

TABLE 4

| Example No. | R$^1$ | R$^2$ | R$^3$ | Yield (%) | m.p. (°C.) or form | NMR (DMSO-d$_6$): δ |
|---|---|---|---|---|---|---|
| 61 | NC—[pyridine]—OH | H | H | 80 | 211~213 (decomp.) | 11.79(1H, bs, NH) 8.27(1H, d, J=7Hz, C$_6$—H) 8.00(1H, d, J=8Hz, C$_4$—H of the pyridine ring) 6.38(1H, d, J=8Hz, C$_5$—H of the pyridine ring) 6.24(1H, t, J=6Hz, C$_1'$—H) 5.60-5.50 (1H, m, C$_3'$—H) 4.19-4.13(1H, m, C$_4'$—H) 3.97-3.42(3H, m, C$_5'$—H and C$_5'$—OH) 2.56-2.38(2H, m, C$_2'$—H) |
| 62 | [pyridine with CN]—OH | H | H | 8 | powder | 11.80(1H, bs, NH) 8.26(1H, d, J=7Hz, C$_6$—H) 7.99(1H, d, J=8Hz, C$_4$—H of the pyridine ring) 6.41(1H, d, J=8Hz, C$_5$—H of the pyridine ring) 6.22(1H, t, J=6Hz, C$_1'$—H) 5.53-5.43(1H, m, C$_3'$—H) 4.13-4.12(1H, m, C$_4'$—H) 3.98-3.65(2H, m, C$_5'$—H) 3.38(1H, bs, C$_5'$—OH) 2.57-2.38(2H, m, C$_2'$—H) |
| 63 | [pyridine]—OH | Ac | CO-[phenyl]-Cl | 76 | powder | solvent: CDCl$_3$ 8.33(1H, bs, OH), 7.86(1H, d, J=Hz, C$_6$—H), 7.85 and 7.43(each 2H, d, J=9Hz, phenyl-H), 7.46(1H, t, J=8Hz, C$_4$—H of the pyridine ring) 6.35-6.06(3H, m, C$_1'$—H and C$_{3,5}$—H of the pyridine ring) 5.26-5.20(1H, m, C$_3'$—H) 4.67-4.27 (3H, m, C$_{4',5'}$—H) 2.80-2.28(2H, m, C$_2'$—H) 2.13 (3H, s, COCH$_3$) |

EXAMPLE 64

Preparation of
2'-deoxy-5-fluoro-3'-O-(2-furanylmethyl)uridine

A 0.35 g quantity of particulate potassium hydroxide and 0.29 g of 2-chloromethylfuran were added to a 2.25-2.11 (2H, m, C$_2'$-H)

EXAMPLES 65 TO 77

The compounds as listed below in Table 5 were prepared in the same manner as in Example 64.

TABLE 5

| Example No. | R¹ | R² | R³ | Yield (%) | m.p. (°C.) or form | NMR (DMSO-d₆): δ |
|---|---|---|---|---|---|---|
| 65 | 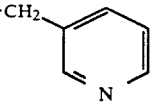 | H | H | 42 | 195~197 | 11.84(1H, bs, NH)8.71-8.50(2H, m, C₂,₆—H of the pyridine ring), 8.20(1H, d, J=7Hz, C₆—H), 7.77(1H, dd, J=2Hz, J=8Hz, C₄—H of the pyridine ring), 7.39(1H, dd, J=5Hz, J=8Hz, C₅—H of the pyridine ring), 6.13(1H, t, J=6Hz, C₁'—H), 5.26-5.17(1H, bs, C₅'—OH), 4.59(2H, s, —CH₂—) 4.26-4.17(1H, m, C₃'—H)4.11-4.04(1H, m, C₄'—H)3.63(2H, bs, C₅'—H)2.52-2.26(m, C₂'—H, overlapped with DMSO) |
| 66 | 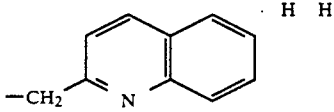 | H | H | 78 | 206~208 | 11.85(1H, d, NH), 8.39(1H, d, J=9Hz, C₄—H of the quinoline ring)8.24(1H, d, J=7Hz, C₆—H)8.05-7.50(5H, m, C₃,₅,₆,₇,₈—H of the quinoline ring), 6.21(1H, t, J=7Hz, C₁'—H), 5.24(1H, bs, C₅'—OH), 4.83(2H, s, —CH₂—)4.37-4.32(1H, m, C₃'—H)4.20-4.11(1H, m, C₄'—H)3.69(2H, bs, C₅'—H)2.48-2.00(2H, m, C₂'—H) |
| 67 | 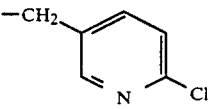 | H | H | 12 | powder | 11.82(1H, bs, NH), 8.41(1H, d, J=2Hz, C₂—H of the pyridine ring)8.21(1H, d, J=7Hz, C₆—H)7.85(1H, dd, J=2Hz, J=8Hz, C₄—H of the pyridine ring), 7.51(1H, d, J=8Hz, C₅—H of the pyridine ring), 6.15(1H, t, J=7Hz, C₁'—H)5.22(1H, bs, C₅'—OH), 4.60(2H, s, —CH₂—), 4.27-4.18(1H, m. C₃'—H), 4.15-4.06(1H, m, C₄'—H), 3.67-3.64(2H, m, C₅'—H)2.45-2.27(2H, m, C₂'—H) |
| 68 | 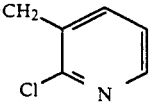 | H | H | 9 | powder | 11.82(1H, bs, NH), 8.37(1H, dd, J=2Hz, J=5Hz, C₆—H of the pyridine ring), 8.22(1H, d, J=7Hz, C₆—H)7.96(1H, dd, J=2Hz, J=7Hz, C₄—H of the pyridine ring), 7.46(1H, dd, J=5Hz, J=7Hz, C₅—H of the pyridine ring), 6.17(1H, t, J=7Hz, C₁'—H)5.23(1H, t, J=5Hz, C₅'—OH)4.62(2H, s, —CH₂—), 4.33-4.27(1H, m, C₃'—H), 4.11-4.08(1H, m, C₄'—H), 3.71-3.62(2H, m, C₅'—H), 2.54-2.22(m, C₂'—H, overlapped with DMSO) |
| 69 | 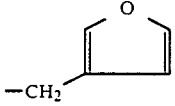 | H | H | 37 | 167~168 | 11.80(1H, bs, NH)8.18(1H, d, J=7Hz, C₆—H)7.64-7.60(2H, m, C₂,₅—H of the furan ring), 6.50-6.47(1H, m, C₄—H of the furan ring)6.09(1H, t, J=7Hz, C₁'—H)5.17(1H, t, J=5Hz, C₅'—OH)4.40(2H, s, —CH₂—)4.22-4.10(1H, m, C₃'—H) 4.04-3.94(1H, m, C₄'—H)3.64-3.57(2H, m, C₅'—H)2.29-2.12 (2H, m, C₂'—H) |
| 70 | 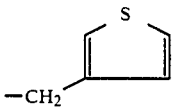 | H | H | 54 | powder | 11.79(1H, bs, NH)8.18(1H, d, J=7Hz, C₆—H)7.56-7.43(2H, m, C₂,₅—H of the thiophene ring), 7.09(1H, dd, J=1Hz, J=5Hz, C₄—H of the thiophene ring)6.19-6.02(1H, m, C₁'—H)5.17(1H, t, J=4Hz, C₅'—OH)4.53(2H, s, —CH₂—) 4.20-4.14(1H, m, C₃'—H)4.02-3.99(1H, m, C₄'—H)3.64-3.60 (2H, m, C₅'—H)2.29-2.12(2H, m, C₂'—H) |
| 71 | 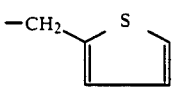 | H | H | 40 | 183~184 | 11.80(1H, d, NH)8.18(1H, d, J=7Hz, C₆—H)7.50(1H, dd, J=1Hz, J=5Hz, C₅—H of the thiophene ring), 7.17-6.95(2H, m, C₃,₄—H of the thiophene ring)6.19-6.05(1H, m, C₁'—H) 5.18(1H, t, J=5Hz, C₅'—OH)4.71(2H, s, —CH₂—)4.26-4.14 (1H, m, C₃'—H)4.05-3.95(1H, m, C₄'—H)3.63-3.56(2H, m, C₅'—H)2.34-1.96(2H, m, C₂'—H) |
| 72 | 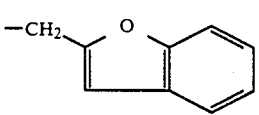 | H | H | 61 | 153~154 | 11.82(1H, d, NH)8.20(1H, d, J=7Hz, C₆—H)7.68-7.53 and 7.33-7.15(4H, m, C₄,₅,₆,₇—H of the benzofuran ring)6.92(1H, s, C₃—H of the benzofuran ring), 6.14(1H, t, J=6Hz, C₁'—H)5.21(1H, t, J=5Hz, C₅'—OH)4.69(2H, s, —CH₂—) 4.31-4.25(1H, m, C₃'—H)4.05-4.03(1H, m, C₄'—H)3.67-3.58 (2H, m, C₅'—H)2.34-2.16(2H, m, C₂'—H) |
| 73 | 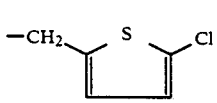 | H | H | 62 | 133~134 | solvent: CDCl₃ 9.64(1H, bs, NH)7.95(1H, d, J=6Hz, C₆—H) 6.76(2H, s, C₃,₄—H of the thiophene ring), 6.20(1H, t, J=6Hz, C₁'—H), 4.59(2H, s, —CH₂—)4.32-4.19(1H, m, C₃'—H)4.14-4.05(1H, m, C₄'—H)4.00-3.66(2H, m, C₅'—H) 2.98(1H, bs, C₅'—OH)2.59-1.99(2H, m, C₂'—H) |
| 74 | 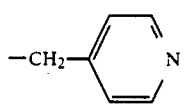 | H | H | 9 | powder | 11.82(1H, bs, NH)8.54(2H, d, J=6Hz, C₂,₆—H of the pyridine ring)8.20(1H, d, J=7Hz, C₆—H)7.34(2H, d, J=6Hz, C₃,₅—H of the pyridine ring)6.12(1H, t, J=6Hz, C₁'—H)5.22(1H, bs, C₅'—OH)4.61(2H, s, —CH₂—)4.25-4.07(2H, m, C₃',₄'—H) 3.64(2H, bs, C₅'—H)2.53-2.18(m, C₂'—H, overlapped with DMSO) |

TABLE 5-continued

| Example No. | R¹ | R² | R³ | Yield (%) | m.p. (°C.) or form | NMR (DMSO-$d_6$): δ |
|---|---|---|---|---|---|---|
| 75 | —$CH_2$—[thiophene]—Br | H | H | 35 | powder | 11.80(1H, bs, NH)8.19(1H, d, J=7Hz, $C_6$—H)7.10 and 6.93 (each 1H, d, J=4Hz, $C_3$—H or $C_4$—H of the thiophene ring) 6.11(1H, t, J=6Hz, $C_1'$—H)5.20(1H, bs, $C_5'$—OH)4.67(2H, s, —$CH_2$—)4.24–4.16(1H, m, $C_3'$—H)4.06–3.99(1H, m, $C_4'$—H) 3.77–3.47(2H, m, $C_5'$—H)2.40–2.07(2H, m, $C_2'$—H) |
| 76 | —$CH_2$—[furan]—CH($CH_3$)$_2$ | H | H | 40 | powder | 11.81(1H, d, NH)8.19(1H, d, J=7Hz, $C_6$—H)7.36(1H, s, $C_5$—H of the furan ring)6.40(1H, s, $C_3$—H of the furan ring) 6.09(1H, t, J=6Hz, $C_1'$—H)5.19(1H, t, J=5Hz, $C_5'$—OH)4.43 (2H, s, —$CH_2$—)4.20–4.12(1H, m, $C_3'$—H)3.97–3.94(1H, m, $C_4'$—H)3.64–3.60(2H, m, $C_5'$—H)2.80–2.53(1H, m, —C$\underline{H}$($CH_3$)$_2$)2.26–2.10(2H, m, $C_2'$—H)1.14(6H, d, J=7Hz, —CH(C$\underline{H_3}$)$_2$) |
| 77 | —$CH_2$—[thiophene]—$CH_3$ | H | H | 34 | powder | 11.80(1H, bs, NH)8.18(1H, d, J=7Hz, $C_6$—H)6.85 and 6.67 (each 1H, d, J=4Hz, $C_3$—H or $C_4$—H of the thiophene ring) 6.17–6.01(1H, m, $C_1'$—H)5.17(1H, t, J=5Hz, $C_5'$—OH)4.61 (2H, s, —$CH_2$—)4.21–4.11(1H, m, $C_3'$—H)4.00–3.93(1H, m, $C_4'$—H)3.71–3.43(2H, m, $C_5'$—H)2.42(3H, s, —$CH_3$)2.29–2.11 (2H, m, $C_2'$—H) |

EXAMPLE 78

Preparation of 3'-O-[4-(6-benzoyloxy-3-cyano-2-pyridyloxycarbonyl)-benzyl] -2'-deoxy-5-fluorouridine To a solution of 1.00 g of 3'-O-(4-carboxybenzyl)-2'-deoxy-5-fluorouridine in 60 ml of dioxane were added 1.82 ml of triethylamine and 0.43 ml of trimethylsilyl chloride. The mixture was stirred at 70° C. for 1 hour. The reaction mixture was filtered and the filtrate was concentrated under reduced pressure. Added thereto were 60 ml of dimethylformamide, 0.76 g of 6-benzoyloxy-3-cyano-2-hydroxypyridine and 0.65 g of N, N'-dicyclohexylcarbodiimide. The mixture was stirred at room temperature for a day. The reaction mixture was concentrated and ethyl acetate and water were added to the residue. The mixture was extracted. The organic layer was dried over magnesium sulfate and concentrated. The residue was purified by silica gel column chromatography using 10% acetone-ethylene chloride as an eluent, giving 0.30 g of 3'-O-[4-(6-benzoyloxy-3-cyano-2-pyridyloxy-carbonyl)benzyl]-2'-deoxy-5-fluo rouridine in a yield of 19%.

NMR (DMSO-$d_6$) δ:
11.83 (1H, d, J=5Hz, N-H),
8.79 (1H, d, J=8Hz,

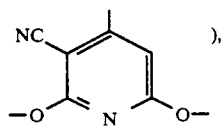

), 8.25–8.13 (5H, m, $H_2$

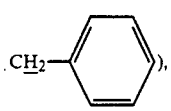

and and $C_6$-H),
7.78–7.59 (6H, m,

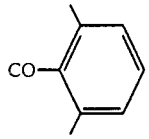

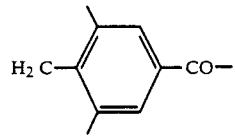

and

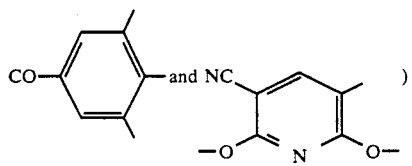

)

6.30–6.15 (1H, m, $C_1'$-H),
5.23 (1H, bs, $C_5'$-OH),
4.72 (2H, s,

.$CH_2$—[phenyl]), 4.29–4.21 (1H, m, $C_3'$-H),
4.13–4.06 (1H, m, $C_4'$-H),
3.71–3.61 (2H, m, $C_5'$-H),
2.42–2.20 (2H, m, $C_2'$-H),

EXAMPLE 79

Preparation of
5'-O-acetyl-2'-deoxy-5-fluoro-3-(4-methoxybenzoyl)-3'-O-(2-thienyl)methyl luridine To a solution of 0.30 g of 5'-O-acetyl-2'-deoxy-5-fluoro-3'-O-(2-thienyl)methyluridine in 10 ml of dioxane were added 0.55 ml of triethylamine and 0.16 g of 4-methoxy-benzoyl chloride. The mixture was stirred at 80° C. for 2 hours. The solvent was distilled off and the residue was dissolved in 30 ml of ethyl acetate. The solution was washed with water. The ethyl acetate layer was dried over sodium anhydrous sulfate and concentrated. The residue was subjected to silica gel chromatography and purified by elution with chloroform, giving 0.37 g of 5'-O-acetyl-2'-deoxy-5-fluoro-3-(4-methoxybenzoyl)-3'-O-(2-thienyl)me thyluridine in a yield of 91%.

NMR (CDCl$_3$) δ:

7.86 (2H, d, J=9Hz,

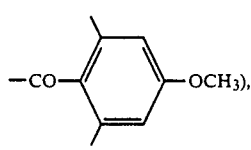

7.76 (1H, d, J=6Hz, C$_6$-H),
7.31–7.24 (1H, m, C$_5$-H of thiophene ring),
7.00–6.84 (4H,m,

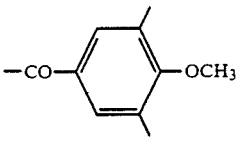

and C$_{3,4}$-H of thiophene ring),
6.19 (1H, t, J=6Hz, C$_{1'}$-H),
4.64 (2H, s, —CH$_2$—),
4.23–4.11 (4H, m, C$_{3',4',5'}$-H),
3.82 (3H, s, —OCH$_3$),
2.62–2.35 and 2.24–2.08 (5H, m, C$_{2'}$-H and —COCH$_3$)

EXAMPLE 80 TO 82

The compounds as listed below in Table 6 were prepared in the same manner as in Example 79.

TABLE 6

| Example No. | R$^1$ | R$^2$ | R$^3$ | Yield (%) | m.p. (°C.) or form | NMR (CDCl$_3$): δ |
|---|---|---|---|---|---|---|
| 80 | —CH$_2$-(2-thienyl) | Ac | —CO-(3-methylphenyl) | 76 | powder | 7.76 (1H, d, J=6Hz, C$_6$—H) 7.44–7.18 (5H, m, phenyl-H and C$_5$—H of the thiophene ring), 7.00–6.95 (2H, m, C$_{3,4}$—H of the thiophene ring) 6.21 (1H, t, J=6Hz, C$_{1'}$—H) 4.69 (2H, s, —CH$_2$—) 4.28–4.15 (4H, m, C$_{3',4',5'}$—H) 2.68–2.11 (8H, m, C$_{2'}$—H and CH$_3$ and COCH$_3$) |
| 81 | —CH$_2$-(2-thienyl) | Ac | —CO-(2-chlorophenyl) | 74 | powder | 7.76 (1H, d, J=6Hz, C$_6$—H) 7.47–7.24 (5H, m, phenyl-H and C$_5$—H of the thiophene ring), 6.99–6.94 (2H, m, C$_{3,4}$—H of the thiophene ring) 6.16 (1H, t, J=6Hz, C$_{1'}$—H) 4.67 (2H, s, —CH$_2$—) 4.26–4.14 (4H, m, C$_{3',4',5'}$—H) 2.68–2.40 and 2.22–1.96 (5H, m, C$_{2'}$—H and COCH$_3$) |
| 82 | —CH$_2$-(5-chloro-2-thienyl) | —CO—O—phenyl | H | 47 | powder | 11.88 (1H, bs, NH) 7.94 (1H, d, J=7Hz, C$_6$—H) 7.53–7.16 (5H, m, phenyl-H) 7.00 (2H, s, C$_{3,4}$—H of the thiophene ring), 6.31–6.02 (1H, m, C$_{1'}$—H) 4.68 (2H, s, —CH$_2$—) 4.45–4.21 (4H, m, C$_{3',4',5'}$—H) 2.36–2.24 (2H, m, C$_{2'}$—H) |

EXAMPLE 83

Preparation of
3'-O-(6-benzoyloxy-3-cyano-2-pyridyl)-2'-deoxy-5-fluorouridine

To a solution of 0.50 g of 3'-O-(3'-cyano-6-hydroxy-2-pyridyl) -2'-deoxy-5-fluorouridine in 30 ml of dioxane were added 0.95 ml of triethylamine and 0.21 ml of trimethylchlorosilane. The mixture was stirred at 70° C. for 5 hours. The insolubles were filtered and the filtrate was concentrated. To the residue were added 50 ml of dioxane, 0.16 g of benzoic acid, and 0.28 g of dicyclohexylcarbodiimide. The mixture was stirred at room temperature overnight. The reaction mixture was filtered and concentrated and the residue was purified by silica gel column chromatography using 3% methanol-chloroform as an eluent, giving 0.10 g of 3'-O-(6-benzoyloxy-3-cyano-2-pyridyl)-2'-deoxy-5-fluorouridine in a yield of 16%.

NMR (CDCl₃) δ:
8.20–7.96 (4H, m, C₆-H and

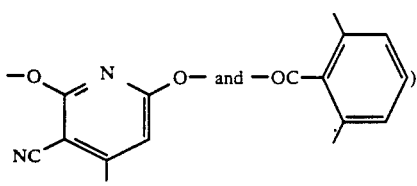

7.74–7.41 (3H, m,

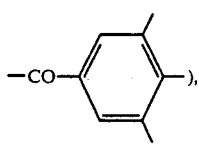

6.95 (1H, d, J=8Hz

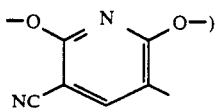

6.32 (1H, t, J=6Hz, C₁'-H),
5.68–5.59 (1H, m, C₃'-H),
4 38–4.32 (1H, m, C₄'-H),
4.01–3.98 (2H, m, C₅'-H),
m, C₅'-OH and C₂'''-H)

EXAMPLE 84

Preparation of
3'-O-(2-thienyl)methyl-3-[3-(4-benzoyloxy-5-chloro-2-pyridyloxycarbonyl) benzoyl]-2'-deoxy-5fluorouridine Trimethylchlorosilane (1.48 ml) and triethylamine (4.04 ml) were added to a solution of 1.00 g of 3'-O-(2-thienyl)methyl-2'-deoxy-5-fluorouridine in 30 ml of dried dioxane. The mixture was stirred at room temperature for 20 minutes. The precipitate formed was filtered and the filtrate was concentrated. The residue was dissolved in 30 ml of dried dioxane. To the solution were added 0.71 g of isophthaloyl chloride and 2.43 ml of triethylamine. The mixture was stirred at 100° C. for 1 hour. The reaction mixture was cooled to room temperature and 1.09 g of 4-benzoyloxy-5-chloro-2(1H)-pyridone was added thereto. The mixture was stirred at room temperature for 2 hours. The precipitate thus formed was filtered and the filtrate was concentrated. The residue was dissolved in 50 ml of ethyl acetate. The solution was washed with 30 ml portions of a saturated aqueous solution of sodium chloride three times. The ethyl acetate layer was dried over sodium anhydrous sulfate and concentrated. To the residue were added 50 ml of acetone and 10 ml of water. The mixture was heated at 40° C. for 3 hours. The solvent was distilled off and the residue was subjected to silica gel column chromatography and eluted with 4% acetone-1,2-dichloroethane, giving 0.40 g of 3'-O(2-thienyl) methyl-3-[3-[4-benzoyloxy-5-chloro-2-pyridyloxycarbonyl) benzoyl]-2'-deoxy-5-fluorouridine as powder in a yield of 19%.

NMR (CDCl₃) δ:
8.89–8.09 (7H, m,

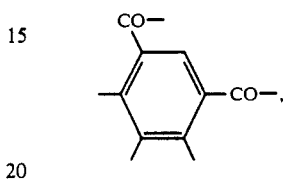

C₆-H of pyridine ring

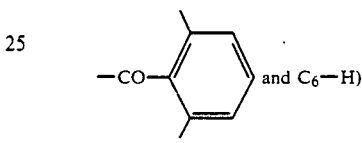

7.76–7.42 (4H,

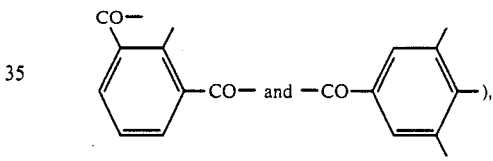

7.39 (1H, s, C₃-H of pyridine ring),
7.31–7.24 (1H, m, C₅-H of thiophene ring),
6.99–6.93 (2H, m, C₃,₄-H of thiophene ring),
6.22 (1H, t, J=6Hz, C₁'-H),
4.67 (2H, s, —CH₂—),
4.34–4.07 (2H, m, C₃'-H and C₄'-H),
4.00–3.63 (2H, m, C₅'-H),
2.80–2.08 (3H, m, C₂'-H and C₅'-OH)

EXAMPLES 85 AND 86

The compound of Example 85 as listed below in Table 7 was prepared in the same manner as in Example 1, and the compound of Example 86 as shown below in Table 7 was prepared in the same manner as in Example 64.

TABLE 7

| Example No. | R¹ | R² | R³ | Yield (%) | m.p. (°C.) or form | NMR (DMSO-d₆): δ |
|---|---|---|---|---|---|---|
| 85 | (N—N / N—N-phenyl triazole group) | H | H | 79 | 214–216 | 11.85 (1H, bs, NH) 8.26 (1H, d, J=7Hz, C₆—H) 7.84–7.52 (5H, m, phenyl-H) 6.33–6.16 (1H, m, C₁'—H) 5.57 (1H, d, J=5Hz, C₃'—H) 5.40 (1H, bs, C₅'—OH), 4.39–4.38 (1H, m, C₄'—H), 3.91–3.63 (2H, m C₅'—H), 2.85–2.31 (m, C₂'—H, overlapped with DMSO) |

TABLE 7-continued

| Example No. | R¹ | R² | R³ | Yield (%) | m.p. (°C.) or form | NMR (DMSO-$d_6$): δ |
|---|---|---|---|---|---|---|
| 86 | -CH$_2$-(thiazole: N,S) | H | H | 41 | powder | 11.82 (1H, bs, NH)<br>8.19 (1H, d, J=7Hz, C$_6$—H)<br>7.80 and 7.72 (each 1H, d, J=3Hz, C$_4$—H and C$_5$—H of the thiazole ring)<br>6.23-6.06 (1H, m, C$_{1'}$—H)<br>5.21 (1H, t, J=5Hz, C$_{5'}$—OH)<br>4.86 (2H, s, CH$_2$)<br>4.37-4.26 (1H, m, C$_{3'}$—H)<br>4.10-4.01 (1H, m, C$_{4'}$—H)<br>3.68-3.52 (2H, m, C$_{5'}$—H)<br>2.42-2.05 (2H, m, C$_{2'}$—H) |

EXAMPLES 87 AND 90

The compounds as indicated below in Table 8 were prepared in the same manner as in Example 64.

EXAMPLE 91

Preparation of 3-[3-(6-benzoyloxy-3-cyano-2pyridyloxycarbonyl)benzoyl]-1-benzyloxymethyl-5fluorouracil A 2.00 g quantity of isophthal chloride was added to a solution of 2.00 g of 1-benzyloxy-5fluorouracil in 70

TABLE 8

| Example No. | R¹ | R² | R³ | Yield (%) | m.p. (°C.) or form | NMR (DMSO-$d_6$): δ |
|---|---|---|---|---|---|---|
| 87 | -CH$_2$-(thiophene with Br, Br) | H | H | 39 | 110-112 | 11.81 (1H, bs, NH)<br>8.19 (1H, d, J=7Hz, C$_6$—H)<br>7.28 (1H, s, H of the thiophene ring)<br>6.11 (1H, t, J=6Hz, C$_{1'}$—H)<br>5.21 (1H, t, J=5Hz, C$_{5'}$—OH)<br>4.63 (2H, s, —CH$_2$—)<br>4.24-4.19 (1H, m, C$_{3'}$—H)<br>4.09-3.98 (1H, m, C$_{4'}$—H)<br>3.67-3.58 (2H, m, C$_{5'}$—H)<br>2.33-2.16 (2H, m, C$_{2'}$—H) |
| 88 | -CH$_2$-(thiophene with Cl, Cl) | H | H | 74 | 147-149 | 11.81 (1H, bs, NH)<br>8.17 (1H, d, J=7Hz, C$_6$—H)<br>7.12 (1H, s, H of the thiophene ring)<br>6.09 (1H, t, J=6Hz, C$_{1'}$—H)<br>5.19 (1H, t, J=5Hz, C$_{5'}$—OH)<br>4.66 (2H, s, —CH$_2$—)<br>4.25-4.16 (1H, m, C$_{3'}$—H)<br>4.05-3.95 (1H, m, C$_{4'}$—H)<br>3.65-3.56 (2H, m, C$_{5'}$—H)<br>2.37-2.44 (2H, m, C$_{2'}$—H) |
| 89 | -CH$_2$-(thiophene with Cl) | H | H | 40 | powder | 11.81 (1H, bs, NH)<br>8.17 (1H, d, J=6Hz, C$_6$—H)<br>7.66 (1H, d, J=5Hz, C$_5$—H of the thiophene ring)<br>7.06 (1H, d, J=5Hz, C$_4$—H of the thiophene ring)<br>6.12 (1H, t, J=6Hz, C$_{1'}$—H)<br>5.21 (1H, t, J=5Hz, C$_{5'}$—OH)<br>4.68 (2H, s, —CH$_2$—)<br>4.30-4.17 (1H, m, C$_{3'}$—H)<br>4.05-3.96 (1H, m, C$_{4'}$—H)<br>3.67-3.58 (2H, m, C$_{5'}$—H)<br>2.38-2.16 (2H, m, C$_{2'}$—H) |
| 90 | -CH$_2$-(thiophene with Br) | H | H | 55 | powder | 11.81 (1H, bs, NH)<br>8.20 (1H, d, J=7Hz, C$_6$—H)<br>7.65 (1H, d, J=5Hz, C$_5$—H of the thiophene ring)<br>7.09 (1H, d, J=5Hz, C$_4$—H of the thiophene ring)<br>6.13 (1H, t, J=7Hz, C$_{1'}$—H)<br>5.21 (1H, bs, C$_{5'}$—OH)<br>4.67 (2H, s, —CH$_2$—)<br>4.28-4.20 (1H, m, C$_{3'}$—H)<br>4.08-4.00 (1H, m, C$_{4'}$—H)<br>3.64 (2H, bs, C$_{5'}$—H)<br>2.40-2.17 (2H, m, C$_{2'}$—H) | ml of dioxane. To the mixture was added dropwise 2.40 ml of triethylamine with stirring at room temperature. After addition, the mixture was stirred at room temperature for 30 minutes and then at 60° C. for 30 minutes. The insolubles were removed by filtration and the filtrate was concentrated. The residue was purified by silica gel column chromatography using as an eluent 1-3% ethyl acetate-dichloromethane, giving 1.30 g of 3-[3-(6-benzoyloxy-3-cyano-2-pyridyloxycarbonyl)benzoyl]-1-benzyloxymethyl-5-fluorouracil.

NMR (CDCl₃) δ:
8.66-8.14 (6H, m,

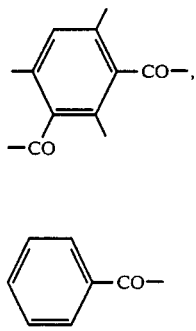

and C₄-H of pyridine ring),
7.79-7.25 (11H, m,

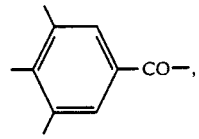

C₆-H,

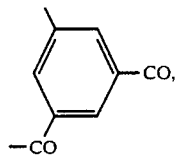

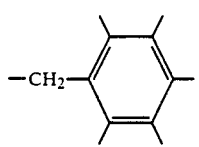

and C₅-H of pyridine ring),
5.21 (2H, s, N—CH₂—),
4.63 (2H, s, O—CH₂—)

EXAMPLES 92 AND 93

The compounds as listed below in Table 9 were prepared in the same manner as in Example 91.

TABLE 9

| Example No. | R¹·⁴ | form |
|---|---|---|
| 92 | —CH₂-(thienyl) | powder |
| 93 | —CH₂-(chlorothienyl) | powder |

| Example No. | NMR (CDCl₃): δ |
|---|---|
| 92 | 8.66-8.15(6H, m, 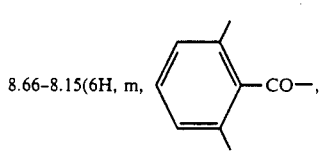 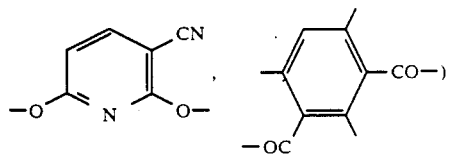 |

TABLE 9-continued
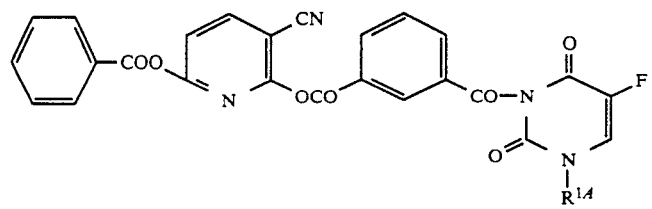
| | |
|---|---|
| 93 | 7.79–7.34(7H, m, —⟨Ar⟩—CO—), 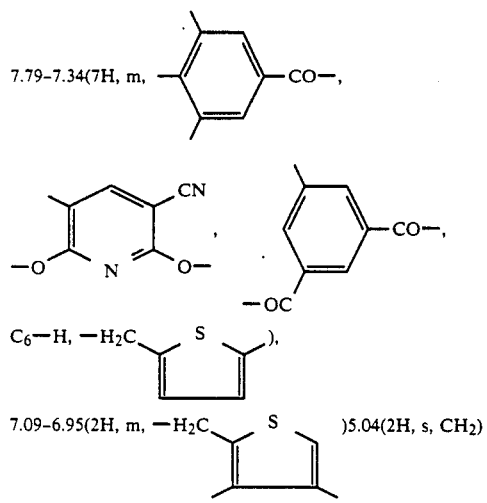 7.09–6.95(2H, m, —H₂C⟨thiophene⟩) 5.04(2H, s, CH₂) |
| | 8.66–8.15(6H, m, —⟨Ar⟩—CO—), 7.82–7.32(6H, m, —⟨Ar⟩—CO—, 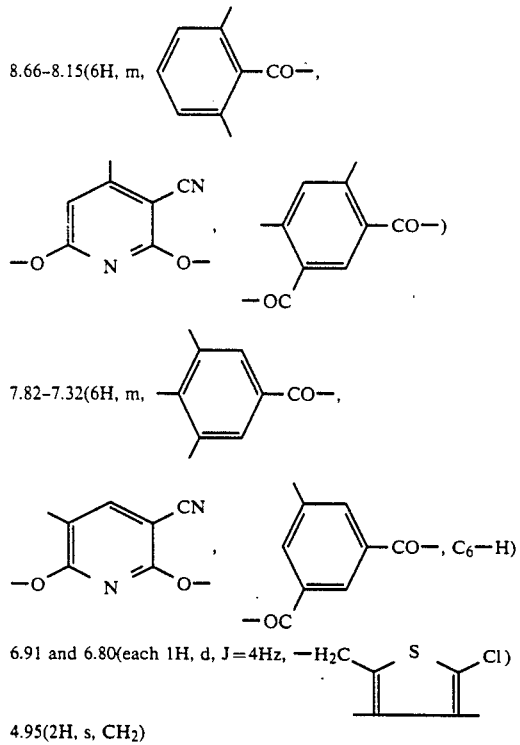 6.91 and 6.80(each 1H, d, J=4Hz, —H₂C⟨thiophene⟩—Cl) 4.95(2H, s, CH₂) |
EXAMPLES 94 AND 95
The compounds as listed below in Table 10 were prepared in the same manner as in Example 84.
TABLE 10
| Example No. | $R^1$ | $R^2$ | $R^3$ |
|---|---|---|---|

TABLE 10-continued
| 94 | -CH₂-[thiophene] | H | 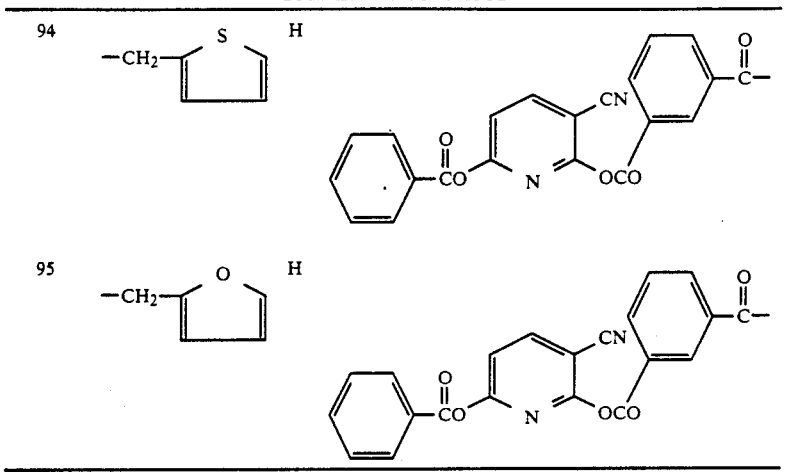 |
|---|---|---|---|
| 95 | -CH₂-[furan] | H | |
| Ex. No. | Yield (%) | m.p. (°C.) or form | NMR (CDCl₃): δ |
|---|---|---|---|
| 94 | 44 | powder | 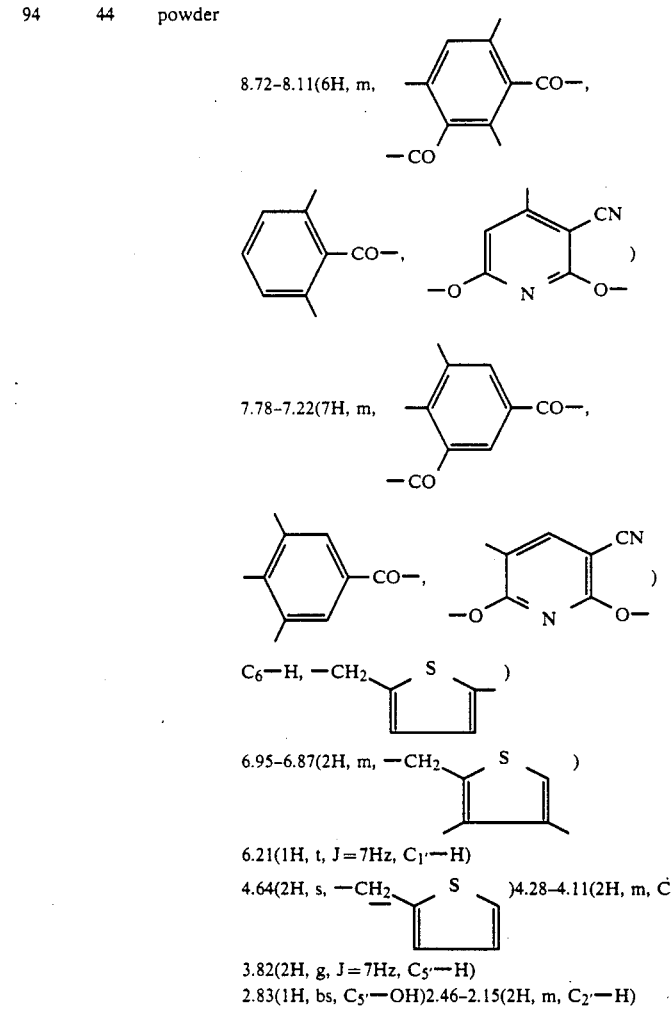 |
| 95 | 38 | powder | 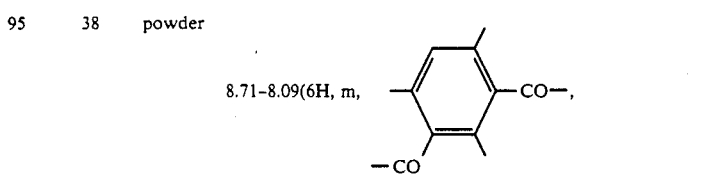 |

TABLE 10-continued

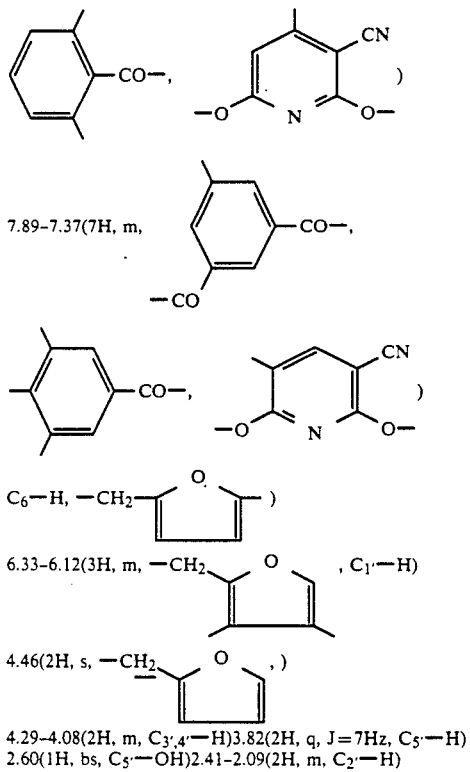

7.89–7.37(7H, m, $C_6$—H, —CH$_2$— (furan) )

6.33–6.12(3H, m, —CH$_2$— (furan), $C_{1'}$—H)

4.46(2H, s, —CH$_2$— (furan), )

4.29–4.08(2H, m, $C_{3',4'}$—H)3.82(2H, q, J=7Hz, $C_{5'}$—H)
2.60(1H, bs, $C_{5'}$—OH)2.41–2.09(2H, m, $C_{2'}$—H)

EXAMPLE 96

The compound as listed below in Table 11 was prepared in the same manner as in Example 64.

TABLE 11

| Example No. | R$^1$ | R$^2$ | R$^3$ | Yield (%) | m.p. (°C.) or form |
|---|---|---|---|---|---|
| 96 | H | —CH$_2$-(thiophene) | H | 57 | powder |

| Ex. No. | NMR(CDCl$_3$): δ |
|---|---|
| 96 | 11.78(1H, bs, NH)<br>7.92(1H, d, J=7Hz, $C_6$—H)<br>7.52(1H, dd, J=1Hz, J=5Hz,<br>$C_5$—H of the thiophene ring)<br>7.07–6.95(2H, m, $C_{3,4}$—H of the thiophene ring)<br>6.13(1H, td, J=6Hz, J=2Hz, $C_{1'}$—H)<br>5.31(1H, d, J=5Hz, $C_{3'}$—OH)<br>4.72(2H, s, —CH$_2$—)<br>4.28–4.13(1H, m, $C_{3'}$—H)<br>3.97–3.80(1H, m, $C_{4'}$—H)<br>3.70–3.61(2H, m, $C_{5'}$—H)<br>2.17–2.05(2H, m, $C_{2'}$—H) |

Pharmacological Test I

Sarcoma-180 subcultured in an ascites of ICR mice was diluted with a physiological saline solution and subcutaneously transplanted into the backs of ICR mice in an amount of $2 \times 10^7$ cells each. Twenty-four hours after the transplantation, a test compound suspended in a 5% solution of gum arabic was orally administered to each of mice once a day for 7 consecutive days.

The solid tumor was isolated from under the dorsal skin of mice on the 10th day after the transplantation to measure the weight of the tumor. There was determined the ratio (T/C) of the weight of tumor (T) cut out from the group of mice treated with the test compound to the weight of tumor (C) from the group of mice not treated therewith. The 50% tumor inhibition dose (ED$_{50}$ value) in which T/C is 0.5 was determined from the dose-response curve of dosage and the ratio (T/C). Table 12 shows the results.

TABLE 12

| No. | R$_1$ | R$_2$ | R$_3$ | ED$_{50}$ (mg/kg) |
|---|---|---|---|---|
| 1 | —CH$_2$-(thiophene, S) | COEt | H | 2 |
| 2 | —CH$_2$-(thiophene, S, Cl) | H | H | 4 |
| 3 | —CH$_2$-(thiophene, S, Br) | H | H | 4 |
| 4 | —CH$_2$-(furan, O) | COEt | H | 2 |
| 5 | —CH$_2$-(furan, O) | H | H | 6 |
| 6 | —CH$_2$-(furan, O) | H | H | 6 |

TABLE 12-continued

| No. | test compound (formula(1)) R₁ | R₂ | R₃ | ED₅₀ (mg/kg) |
|---|---|---|---|---|
| 7 | —CH₂—[thiophene] | H | H | 6 |
| 8 | —CH₂—[thiophene] | H | H | 6 |
| 9 | [methylpyridine] | H | H | 7 |
| 10 | —CH₂—[dichlorothiophene] | H | H | 4 |
| 11 | —CH₂—[chlorothiophene] | H | H | 4 |

Preparation examples are given below.

PREPARATION EXAMPLE 1

Compound of Example 54: 50 mg
Lactose: 97 mg
Crystalline cellulose: 50 mg
Magnesium stearate: 3 mg Capsules (200 mg each) were prepared which each had the foregoing composition.

PREPARATION EXAMPLE 2

Compound of Example 54: 10 mg
Lactose: 184 mg
Crystalline cellulose: 100 mg
Magnesium stearate: 6 mg Capsules (300 mg each) were prepared which each had the foregoing composition.

PREPARATION EXAMPLE 3

Compound of Example 57: 10 mg
Lactose: 240 mg
Corn starch: 340 mg
Hydroxypropyl cellulose: 10 mg Granules (600 mg each wrapper) were prepared which each had the foregoing composition.

PREPARATION EXAMPLE 4

Compound of Example 73: 10 mg
Macrogol 300: 500 mg
Distilled water for injection (appropriately)

An injection solution (5 ml per ampul) was prepared which had the foregoing composition.

PREPARATION EXAMPLE 5

A thousand tablets for oral administration were prepared which had the following composition and which each contained 10 mg of the compound obtained in Example 75.

Compound of Example 75: 10 g
Lactose (Japanese Pharmacopeia): 45 g
Corn starch (Japanese Pharmacopeia): 25 g
Crystalline cellulose (Japanese Pharmacopeia): 25 g
Methyl cellulose (Japanese Pharmacopeia): 1.5 g
Magnesium stearate (Japanese Pharmacopeia): 1 g The compound of Example 75, lactose, corn starch and crystalline cellulose were thoroughly mixed and the mixture was granulated with a 5% aqueous solution of methyl cellulose. The granules thus obtained were passed through a 200-mesh sieve and carefully dried. The dry granules were passed through a 200-mesh sieve and mixed with magnesium stearate. The mixture was pressed into tablets.

PREPARATION EXAMPLE 6

Compound of Example 61: 10 mg
Macrogol 300: 500 mg
Distilled water for injection: (appropriately)

An injection solution (5 ml per ampul) was prepared which had the foregoing composition.

What is claimed is:

1. A compound the formula

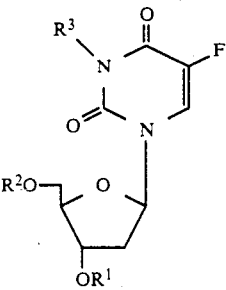

wherein $R^1$ and $R^2$ are each a hydrogen atom, acyl group, phenyl-$C_1$-$C_6$ alkyl group having a group $R^xOCO$—on the phenyl ring, or a group —$(A)_nB$, and wherein at least one of $R^1$ and $R^2$ is a group —$(A)_nB$ wherein n is 1, $R^3$ is a hydrogen atom or an acyl group, with the proviso that when $R^1$ is a hydrogen atom or acyl group, $R^2$ is not a hydrogen atom or acyl group, the acyl group represented by $R^1$, $R^2$ and $R^3$ being one selected from the class consisting of:

(a) $C_1$-$C_6$ alkanoyl groups,
(b) benzoyl groups optionally having 1 to 3 substituents selected from the class consisting of $C_1$-$C_6$ alkyl group, $C_1$-$C_6$ alkoxy group and halogen atom,
(c) phenoxycarbonyl group, and
(d) pyridyloxycarbonyl arylenecarbonyl groups represented by the formula

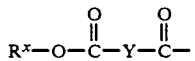

wherein $R^x$ is a pyridyl group optionally having 1 to 4 substituents selected from the class consisting of hydroxyl group, oxo group, halogen atom, amino group, carboxyl group, cyano group, nitro group, carbamoyl group, ($C_1$-$C_6$ alkyl)carbamoyl group, carboxy-($C_1$-$C_6$ alkyl)-carbamoyl group, ($C_1$-$C_6$ alkoxy)carbonyl-($C_1C_6$ alkyl)carbamoyl group, phenylcarbamoyl group optionally having on the phenyl ring 1 to 3 substituents selected from halogen atom, $C_1$-$C_6$ alkyl group and $C_1$-$C_6$ alkoxy group, $C_1$-$C_6$ alkyl group, $C_2$-$C_6$ alkenyl group, ($C_1$-$C_6$ alkoxy)-carbonyl group, tetrahydrofuranyl group, tetrahydropyranyl group, $C_1$-$C_6$ alkoxy-$C_1$-$C_6$ alkyl group, phenyl-$C_1$-$C_6$ alkoxy-$C_1$-$C_6$ alkyl group, $C_1$-$C_6$ alkylthio-$C_1$-$C_6$ alkyl group, $C_1$-$C_6$ alkanoyloxy group, benzoyloxy group optionally having 1 to 3 substituents selected from halogen atom, $C_1$-$C_6$ alkyl group and $C_1$-$C_6$ alkoxy group, and phenoxycarbonyloxy group, Y being a phenylene group, naphthalene group, pyridinediyl group, pyrazinediyl group, furandiyl group or 4-pyridon-1-$C_1$-$C_6$ alkyl-diyl group, the pyridyl group represented by $R^x$ in the phenyl $C_1$-$C_6$ alkyl group with a group $R^x$OCO— on the phenyl ring being the same as the group $R^x$ described above under the item (d), A in the group —$(A)_n$B being a $C_1$-$C_6$ alkylene group, and B in said group being a heterocyclic group such that 1 to 3 substituents may be attached to the heterocyclic ring, the substituents being selected from the class consisting of hydroxyl group, cyano group, halogen atom, $C_1$-$C_6$ alky group, $C_1$-$C_6$ alkoxy group, phenyl group, $C_1$-$C_6$ alkoxy group having 1 or 2 phenyl groups optionally substituted with $C_1$-$C_6$ alkoxy group or halogen atom on the phenyl ring, phenoxy group optionally substituted with halogen atom or $C_1$-$C_6$ alkoxy group on the phenyl ring, nitro group, oxo group, benzoyloxy group, ($C_1$-$C_6$ alkoxy)carbonyl group, $C_1$-$C_6$ alkanoyloxy group, phenyl-$C_1$-$C_6$ alkylthio group and a group of $R^x$OCO— wherein $R^x$ is as defined above, the heterocyclic ring being selected from the class consisting of pyridine, pyrimidine, pyrazine, pyridazine, 1,3,5-triazine, tetrazole, 1,2,4-thiadiazole, 1,2,4-thiadiazole, 1,2,3-thiadiazole, thiazole, isothiazole, pyrrole, 1,4-dioxine, 1,3-dioxine, 1,2-dioxine, quinoline, isoquinoline, 1,5-naphthyridine, 1,6-naphthyridine, 1,7-naphthyridine, 1,8-naphthyridine, benzofuran, benzothiazole, quinoxaline, quinazoline, cinnoline, phthalazine, β-naphthoquinone and benzo-(f)-quinoline, and n being 0 or 1.

2. A compound according to claim 1 which is represented by the formula

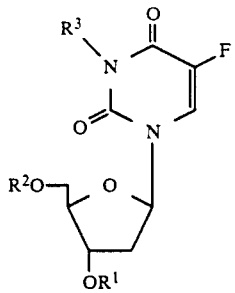

wherein $R^1$ and $R^2$ are each a hydrogen atom, acyl group, phenyl-$C_1$-$C_6$ alkyl group having a group $R^x$OCO— on the phenyl ring, or a group —$(A)_n$B, and wherein at least one of $R^1$ and $R^2$ is a group —$(A)_n$B wherein n is 0, $R^3$ is a hydrogen atom or an acyl group, with the proviso that when $R^1$ is a hydrogen atom or acyl group, $R^2$ is not a hydrogen atom or acyl group, the acyl group represented by $R^1$, $R^2$ and $R^3$ being one selected from the class consisting of:
(a) $C_1$-$C_6$ alkanoyl groups,
(b) benzoyl groups optionally having 1 to 3 substituents selected from the class consisting of $C_1$-$C_6$ alkyl group, $C_1$-$C_6$ alkoxy group and halogen atom,
(c) phenoxycarbonyl group, and
(d) pyridyloxycarbonyl arylenecarbonyl groups represented by the formula

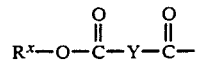

wherein $R^x$ is a pyridyl group optionally having 1 to 4 substituents selected from the class consisting of hydroxyl group, oxo group, halogen atom, amino group, carboxyl group, cyano group, nitro group, carbamoyl group, ($C_1$-$C_6$ alkyl)carbamoyl group, carboxy-($C_1$-$C_6$ alkyl)-carbamoyl group, ($C_1$-$C_6$ alkoxy)carbonyl-($C_1$-$C_6$ alkyl)carbamoyl group, phenylcarbamoyl group optionally having on the phenyl ring 1 to 3 substituents selected from halogen atom, $C_1$-$C_6$ alkyl group and $C_1$-$C_6$ alkoxy group, $C_1$-$C_6$ alkyl group, $C_2$-$C_6$ alkenyl group, ($C_1$-$C_6$ alkoxy)-carbonyl group, tetrahydrofuranyl group, tetrahydropyranyl group, $C_1$-$C_6$ alkoxy-$C_1$-$C_6$ alkyl group, phenyl-$C_1$-$C_6$ alkoxy-$C_1$-$C_6$ alkyl group, $C_1$-$C_6$ alkylathio-$C_1$-$C_6$ alkyl group, $C_1$-$C_6$ alkanoyloxy group, benzoyloxy group optionally having 1 to 3 substituents selected from halogen atom, $C_1$-$C_6$ alkyl group and $C_1$-$C_6$ alkoxy group, and phenoxycarbonyloxy group, Y being a phenylene group, naphthalene group, pyridinediyl group, pyrazinediyl group, furandiyl group or 4-pyridon-1-$C_1$-$C_6$ alkyl-diyl group, the pyridyl group represented by $R^x$ in the phenyl $C_1$-$C_6$ alkyl group with a group $R^x$OCO— on the phenyl ring being the same as the group $R^x$ described above under the item (d), A in the group —$(A)_n$B being a $C_1$-$C_6$ alkylene group, and B in said group being a heterocyclic group such that 1 to 3 substituents may be attached to the heterocyclic ring, the substituents being selected from the class consisting of hydroxyl group, cyano group, halogen atom, $C_1$-$C_6$ alkly group, $C_1$-$C_6$ alkoxy group, phenyl group $C_1$-$C_6$ alkoxy group having 1 or 2 phenyl groups optionally substituted with $C_1$-$C_6$ alkoxy group or halogen atom on the phenyl ring, phenoxy group optionally substituted with halogen atom or $C_1$-$C_6$ alkoxy group on the phenyl ring, nitro group, oxo group, benzoyloxy group, ($C_1$-$C_6$ alkoxy)carbonyl group, $C_1$-$C_6$ alkanoyloxy group, phenyl-$C_1$-$C_6$ alkylthio group and a group a $R^x$OCO— wherein $R^x$ is as defined above, the heterocyclic ring being selected from the class consisting of pyridine, pyrimidine, pyrazine, pyridazine, 1,3,5-triazine, tetrazole, 1,2,4-thiadiazole, 1,2,4-thiadiazole, 1,2,3-thiadiazole, thiazole, isothiazole, pyrrole, b 1,4-dioxine, 1,3-dioxine, 1,2-dioxine, quinoline, isoquinoline, 1,5-naphthyridine, 1,6-naphthyridine, 1,7-naphthyridine, 1,8-naphthyridine, benzofuran, benzothiazole, quinoxaline, quinazoline, cinnoline, phthalazine, β-naphthoquinone and benzo-(f)-quinoline, and n being 0 or 1.

3. A compound according to claim 1 wherein $R^1$ is a group —$(A)_n$B and $R^2$ is a hydrogen atom.
4. A compound according to claim 1 wherein $R^1$ is a group —$(A)_n$B and $R^2$ is an acyl group.
5. A compound according to claim 1 wherein $R^1$ is a hydrogen atom and $R^2$ is a group —$(A)_n$B.

6. A compound according to claim 3 wherein the heterocyclic ring in the heterocyclic group represented by B is furan or thiophen, each being substituted or unsubstituted and $R^3$ is a hydrogen atom.

7. A compound according to claim 3 wherein the heterocyclic ring in the heterocyclic group represented by B is pyridine, quinoline, benzofuran or thiazole, each being substituted or unsubstituted and $R^3$ is a hydrogen atom.

8. A compound according to claim 3 wherein the heterocyclic ring in the heterocyclic group represented by B is furan or thiophene, each being substituted or unsubstituted and $R^3$ is an acyl group.

9. A compound according to claim 6 wherein the heterocyclic ring in the heterocyclic group represented by B is furan or thiophene, each optionally having 1 or 2 substituents selected from the class consisting of halogen atom, $C_1$-$C_6$ alkyl group and $C_1$-$C_6$ alkoxy group, and A is methylene.

10. A compound according to claim 7 wherein the heterocyclic ring in the heterocyclic group represented by B is pyridine, quinoline, benzofuran or thiazole, each optionally having 1 to 2 substituents selected from the class consisting of halogen atom, $C_1$-$C_6$ alkyl group and $C_1$-$C_6$ alkoxy group, and A is methylene.

11. A compound according to claim 8 wherein $R^3$ is benzoyl optionally having 1 to 3 substituents selected from the class consisting of $C_1$-$C_6$ alkyl group, $C_1$-$C_6$ alkoxy group and halogen atom, $C_1$-$C_6$ alkanoyl group, or a group represented by the formula

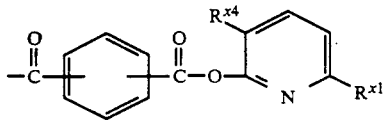

wherein $R^{x4}$ is a cyano group, $R^{x1}$ is benzoyloxy optionally having 1 to 3 substituents selected from the class consisting of $C_1$-$C_6$ alkyl group, $C_1$-$C_6$ alkoxy group and halogen atom, or hydroxyl group, the heterocyclic ring in the heterocyclic group represented by B is furan or thiophene, each optionally having 1 or 2 substituents selected from the class consisting of halogen atom, $C_1$-$C_6$ alkyl group and $C_1$-$C_6$ alkoxy group, and A is methylene.

12. A compound according to claim 4 wherein $R^2$ is $C_1$-$C_6$ alkanoyl group or benzoyl optionally having 1 to 3 substituents selected from the class consisting of halogen atom, $C_1$-$C_6$ alkyl group and $C_1$-$C_6$ alkoxy group, the heterocyclic ring in the heterocyclic group represented by B is furan or thiophene, each being substituted or unsubstituted, and $R^3$ is a hydrogen atom.

13. A compound according to claim 4 wherein $R^2$ is $C_1$-$C_6$ alkanoyl group or benzoyl optionally having 1 to 3 substituents selected from the class consisting of halogen atom, $C_1$-$C_6$ alkyl group and $C_1$-$C_6$ alkoxy group, the heterocyclic ring in the heterocyclic group represented by B is pyridine, quinoline, benzofuran or thiazole, each being substituted or unsubstituted, and $R^3$ is hydrogen atom.

14. A compound according to claim 4 wherein $R^2$ is $C_1$-$C_6$ alkanoyl group or benzoyl optionally having 1 to 3 substituents selected from the class consisting of halogen atom, $C_1$-$C_6$ alkyl group and $C_1$-$C_6$ alkoxy group, the heterocyclic ring in the heterocyclic group represented by B is furan or thiophene, each being substituted or unsubstituted, and $R^3$ is an acyl group.

15. A compound according to claim 12 wherein the heterocyclic ring in the heterocyclic group represented by B is furan or thiophene, each optionally having 1 or 2 substituents selected from the class consisting of halogen atom, $C_1$-$C_6$ alkyl group and $C_1$-$C_6$ alkoxy group, and A is methylene.

16. A compound according to claim 13 wherein the heterocyclic ring in the heterocyclic group represented by B is pyridine, quinoline, benzofuran or thiazole, each optionally having 1 or 2 substituents selected from the class consisting of halogen atom, $C_1$-$C_6$ alkyl group and $C_1$-$C_6$ alkoxy group, and A is methylene.

17. A compound according to claim 14 wherein $R^3$ is benzoyl optionally having 1 to 3 substituents selected from the class consisting of $C_1$-$C_6$ alkyl group, $C_1$-$C_6$ alkoxy group and halogen atom, $C_1$-$C_6$ alkanoyl group, or a group represented by the formula

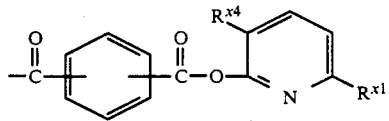

wherein $R^{x4}$ is a cyano group, $R^{x1}$ is benzoyloxy optionally having 1 to 3 substituents selected from the class consisting of $C_1$-$C_6$ alkyl group, $C_1$-$C_6$ alkoxy group and halogen atom, or hydroxyl group, the heterocyclic ring of the heterocyclic group represented by B is furan or thiophene, each optionally having 1 or 2 substituents selected from the class consisting of halogen atom, $C_1$-$C_6$ alkyl group and $C_1$-$C_6$ alkoxy group, and A is methylene.

18. A compound according to claim 2 wherein the heterocyclic ring in the heterocyclic group represented by B is one selected from the class consisting of pyridine, pyrimidine, pyrazine, pyridazine, 1,3,5-triazine, tetrazole, thiazole, quinoline, isoquinoline, 1,5-naphthyridine, 1,8-naphthyridine, benzothiazole, quinoxaline, phthalazine and benzo-[f]-quinoline, each being substituted or unsubstituted.

19. A compound according to claim 18 wherein $R^1$ is a group $-(A)_nB$ and $R^2$ and $R^3$ are each a hydrogen atom.

20. A compound according to claim 19 wherein the heterocyclic ring is substituted or unsubstituted pyridine.

21. A compound according to claim 5 wherein the heterocyclic ring in the heterocyclic group represented by B is thienyl or furanyl, each being substituted or unsubstituted and $R^3$ is a hydrogen atom.

22. A compound according to claim 21 wherein the heterocyclic ring is thienyl or furanyl, each optionally having 1 or 2 substitutents selected from the class consisting of $C_1$-$C_6$ alkyl group, halogen atom and $C_1$-$C_6$ alkoxy group, and A is methylene.

23. A compound according to claim 1 which is selected from the class consisting of 2'-deoxy-5-fluoro-3'-O-(2-furanylmethyl) -5'-O-propanoyluridine, 2'-deoxy-5-fluoro-3'-O-(2-furanylmethyl)uridine, 2'-deoxy-5-fluoro-3'-O-(3-furanylmethyl)uridine, and 2'-deoxy-5-fluoro-3'-O-(2-furanylmethyl) -3-[3-(6-benzoyloxy-3-cyano-2pyridyloxycarbonyl)benzoyl] uridine.

24. A compound according to claim 1 which is selected from the class consisting of 2'-deoxy-5-fluoro3'-

O-(3-thienylmethyl)uridine, 2'-deoxy-5-fluoro-3'-O-(2-thienylmethyl)uridine, 2'-deoxy-5-fluoro-3'-O-(5-chloro-2-thienylmethyl)uridine, 2'-deoxy-5-fluoro-3'-O-(5-bromo-2-thienylmethyl uridine, 2'-deoxy-5-fluoro-3'-O-(4,5-dichloro-2-thienylmethyl) uridine, 2'-deoxy-5-fluoro-3'-O-(3-chloro-2-thienylmethyl) uridine, 2'-deoxy-5-fluoro-3'-O-(3-bromo-2-thienylmethyl) uridine, 2'-deoxy-5-fluoro-3'-O-(2-thienylmethyl) -3-[(3-(6-benzoyloxy-3-cyano-2pyridyloxycarbonyl)benzoyl] uridine and 2'-deoxy-5-fluoro5'-O-(2-thienylmethyl uridine.

25. A compound according to claim 1 which is 2'-deoxy-5-fluoro-3'-O-(5-chloro-2-thienylmethyl)uridine.

26. A compound according to claim 2 which is 2'-deoxy-5-fluoro-3'-O-(6-hydroxy-2-pyridyl)uridine.

* * * * *